United States Patent
Tabor et al.

(10) Patent No.: US 10,793,840 B2
(45) Date of Patent: Oct. 6, 2020

(54) IDENTIFYING LIGANDS FOR BACTERIAL SENSORS

(71) Applicant: William Marsh Rice University, Houston, TX (US)

(72) Inventors: Jeffrey J. Tabor, Houston, TX (US); Sebastian Schmidl, Houston, TX (US); Ravi Sheth, Houston, TX (US); Felix Ekness, Houston, TX (US); Brian Landry, Houston, TX (US); Nikola Dyuglyarov, Houston, TX (US)

(73) Assignee: William Marsh Rice University, Houston, TX (US)

( * ) Notice: Subject to any disclaimer, the term of this patent is extended or adjusted under 35 U.S.C. 154(b) by 0 days.

(21) Appl. No.: 15/571,744

(22) PCT Filed: May 4, 2016

(86) PCT No.: PCT/US2016/030831
§ 371 (c)(1),
(2) Date: Nov. 3, 2017

(87) PCT Pub. No.: WO2016/182819
PCT Pub. Date: Nov. 17, 2016

(65) Prior Publication Data
US 2019/0127711 A1    May 2, 2019

Related U.S. Application Data

(60) Provisional application No. 62/157,293, filed on May 5, 2015.

(51) Int. Cl.
*C12N 9/12* (2006.01)
*C12Q 1/48* (2006.01)

(52) U.S. Cl.
CPC ............. *C12N 9/12* (2013.01); *C12N 9/1229* (2013.01); *C12Q 1/485* (2013.01); *C12Y 207/13003* (2013.01)

(58) Field of Classification Search
CPC ........ C12N 9/1229; C12N 9/12; C12Q 1/485; C12Y 207/13003
See application file for complete search history.

(56) References Cited

U.S. PATENT DOCUMENTS

| 8,652,804 B2* | 2/2014 | Dietrich ......... C12Y 207/13003 435/41 |
| 9,062,320 B2 | 6/2015 | Medford et al. |
| 2003/0049799 A1 | 3/2003 | Schwartz et al. |

FOREIGN PATENT DOCUMENTS

WO    WO2016182819    11/2016

OTHER PUBLICATIONS

Walthers et al., (Interdomain linkers of homologous response regulators determine their mechanism of (Year: 2003).*
West et al., (Trends in Biochemical Sciences. vol. 26, Issue 6, Jun. 2001. pp. 369-376) (Year: 2001).*
Raghaven et al., (Curr Opin Microbiol. Apr. 2010: 13(2)226-231). (Year: 2010).*

(Continued)

*Primary Examiner* — Jana A Hines
(74) *Attorney, Agent, or Firm* — Boulware & Valoir

(57) ABSTRACT

Methods to create two component signal transduction systems by replace the DNA binding domains and output promoters in bacteria are described.

13 Claims, 34 Drawing Sheets

Specification includes a Sequence Listing.

(56) References Cited

OTHER PUBLICATIONS

Walthers et al., Journal of Bacteriology, Jan. 31, 2003 (Jan. 31, 2003), vol. 185, No. 1, pp. 317-324). (Year: 2003).*
Allen, et al. Genetic Evidence that the α5 Helix of the Receiver Domain of PhoB Is Involved in Interdomain Interactions, J. Bacteriology 183(72001): 2204-2211 (2001).
Castillo-Hair, S.M., et al., How to train your microbe: methods for dynamically characterizing gene networks, Current opinion in microbiology 24, 113-123 (2015).
da Silva D.P. et al., Studies on synthetic LuxR solo hybrids, Front. Cell. Infect. Microbiol., Vl. 5, Art. 52 (2015).
Howell, et al, Genes controlled by the essential YycG/YycF two component system of Bacillus subtilis revealed through a novel hybrid regulator approach, Molecular Microbiology, 49(6) 1639-1655 (2003).
Kohanski, M.A., & Collins J.J., Rewiring Bacteria, Two Components at a Time, Cell 133: 947-948 (2008).
Levskaya, A., et al., Synthetic biology: engineering *Escherichia coli* to see light, Nature 438 (7067), 441-442 (2005).
Ryan, R. et al., Toward rationally redesigning bacterial two-component signaling systems using coevolutionary information, PNAS 111(5): E563-E571 (2014).
Schmidl, S.R., et al., Refactoring and optimization of light-switchable *Escherichia coli* two-component systems, ACS synthetic biology 3 (11), 820-831 (2014).
Skerker, J.M., et al., Rewiring the Specificity of Two-Component Signal Transduction Systems, Cell. 133(6): 1043-1054 (2008).
Tabor, J.J., et al., A synthetic genetic edge detection program, Cell 137 (7), 1272-1281 (2009).
Tabor, J.J., et al., Performance characteristics for sensors and circuits used to program *E. coli*, Systems Biology and Biotechnology of *Escherichia coli*, 401-439 7 (2009).
Tabor JJ, et al., Multichromatic Control of Gene Expression in *Escherichia coli*. J Mol Biol 405:315-324 (2010).
Tapparel et al. The DNA-binding domain of the *Escherichia coli* CpxR two-component response regulator is constitutively active and cannot be fully attenuated by fused adjacent heterologous regulatory domains, Microbiology 152: 431-441 (2006).
Walthers et al. Interdomain Linkers of Homologous Response Regulators Determine Their Mechanism of Action, J. Bacteriology Jan. 185(1): 317-324 (2003).
Wang, B., et al., Rewiring cell signalling through chimaeric regulatory protein engineering, Biochem. Soc. Trans. (2013) 41, 1195-1200 (2013).
Van Rensburg et al. "Development and validation of a high-throughput cell-based screen to identify activators of a bacterial two-component signal transduction system," Antimicrobial Agents and Chemotherapy, published online Apr. 13, 2015 (Apr. 13, 2015), vol. 59, No. 7, pp. 3790-3799.
Blanco et al. "Tandem DNA recognition by PhoB, a two-component signal transduction transcriptional activator," Structure, May 31, 2002 (May 31, 2002), vol. 10, No. 5, pp. 701-713.

* cited by examiner

VALIDATION OF PATHWAY ACTIVITY. MUTATION OF CATALYTIC HISTIDINE TO NON-CATALYTIC ASPARAGINE (N) RESIDUE

EnvZ: CONSERVED HISTIDINE AT POSITION 243 WITHIN THE HisKA REGION
  HisKA REGION: ~234-289 (55aa):
...RTLLMAGVSHDLRTPLTRIRLATEMMSEQDGYLAESINKDIEECNAIIEQFIDYLR...

MRRLRFSPRSSFARTLLLIVTLLFASLVTTYLVVLNFAILPSLQQFNKVLAYEVRMLMTDKLQLEDGTQLVVPPAFRREI
YRELGISLYSNEAAEEAGLRWAQHYEFLSHQMAQQLGGPTEVRVEVNKSSPVVWLKTWLSPNIWRVPLTEIHQGDFSPL
FRYTLAIMLLAIGGAWLFIRIQNRPLVDLEHAALQVGKGIIPPPLREYGASEVRSVTRAFNHMAAGVKQLADDRTLLMAG
VSHDLRTPLTRIRLATEMMSEQDGYLAESINKDIEECNAIIEQFIDYLRTGQEMPMEMADLNAVLGEVIAAESGYEREIE
TALYPGSIEVKMHPLSIKRAVANMVVNAARYGNGWIKVSSGTEPNRAWFQVEDDGPGIAPEQRKHLFQPFVRGDSARTIS
GTGLGLAIVQRIVDNHNGMLELGTSERGGLSIRAWLPVPVTRAQGTTKEG*

BAD_0569: CONSERVED HISTIDINE IN THE HisKA REGION
  HisKA REGION: 287-353 (66aa):
...EKMKRFVSDASHELRTPLAAIHGYAELYKMQRDMPGALERADESIEHIEASSARMTVLVEDLLSLAR....

MQPPRSLPKQNKVWSRFTRRIQAIPLSTKLVTCIIVLLTIGTIGISFSIRTLVGNYLLQKTDTQLINQAQLIFNSMDSLS
SDTGDDGRSLMNTYYVEVRDSEYKSTGAGSVPMLRDGVVSEPSLPADGSIDGVTLGQPFTTRAVVHITTSRTPDHSIMQA
AQSPWRVVALPWNEKTRTGQVKDSGVVFIGLSLSDQIDTANTLTRFCAMVGIAVVLIGAILGTILVQSTLAPLKRIEKTA
AKIAAGDLSQRVPDLPESTEVGSLSMSLNTMLTRIEESFHAQEETTEKMKRFVSDASHELRTPLAAIHGYAELYKMQRDM
PGALERADESIEHIEASSARMTVLVEDLLSLARLDEGRGIDITQQVKLTSVVRDAADLHALDPDRGISCGQVVLQPGTD
MDHPAQFAFQNGQMPQIELKGDASRLRQVVTNIVGNIHRYTPADSPVEISMGVLPASISPESLSRMPSNEQSLRHLVEAI
EVGQSMQVGMNYAIVRFSDHGPGVPPEARSKIFERFYTADPSRARQKGGTGLGMAIAQSVVKAHHGFICASGSEGTGLIL
TVVLPIAPVEPKPQPITASENRKNEKKNRKSKK*

FIG. 6

| FIGURE 9: Amino acid sequences of wild-type (native) and chimeric RRs used herein |
|---|
| Native full length wHTH Response Regulators used:<br>Key No Style = REC Domain, Bold = Linker, <u>Underline</u> = DBD. Wild-type RRs contain linkers between the two domains, but these are native sequences, not exogenous linkers. |
| OmpR (E. coli) ACCN: NP_417864 SEQ ID NO: 1 |
| MQENYKILVVDDDMRLRALLERYLTEQGFQVRSVANAEQMDRLLTRESFHLMVLDLMLPGEDGLSICRRL<br>RSQSNPMPIIMVTAKGEEVDRIVGLEIGADDYIPKFNPRELLARIRAVLRRQANELPGAPSQEEA<u>VIAFGK</u><br><u>FKLNLGTREMFREDEPMPLTSGEFAVLKALVSHPREPLSRDKLMNLARGREYSAMERSIDVQISRLRRMV</u><br><u>EEDPAHPRYIQTVWGLGYVFVPDGSKA</u> |
| CcaR (Synechocystis PCC6803) ACCN: WP_010874216 SEQ ID NO: 2 |
| MRILLVEDDLPLAETLAEALSDQLYTVDIATDASLAWDYASRLEYDLVILDVMLPELDGITLCQKWRSHSYL<br>MPILMMTARDTINDKITGLDAGADDYVVKPVDLGELFARVRALLRRGCATCQP<u>VLEWGPIRLDPSTYEVSY</u><br><u>DNEVLSLTRKEYSILELLLRNGRRVLSRSMIIDSIWKLESPPEEDTVKVHVRSLRQKLKSAGLSADAIETVHG</u><br><u>IGYRLANLTEKSLCQGKN</u> |
| CopR (Synechocystis PCC 6803) ACCN: WP_010873936 SEQ ID NO: 3 |
| MRLLLVEDEPDLGMALEKALRRENYVVDWVQDGNLAWSYLDQGWVNYTLAIFDWMVPGLSGLELCQKL<br>RGQRSSLPILMLTAKDQIADRVEGLDAGADDYLIKPFGMAELLARLRSLQRRSPELQPQ<u>QLQVGQWWLD</u><br><u>YGTFAVVTPEQARITLTAKEFQLLEYFMKHPQQILSSEQIKNQLWALSAESTSNVVAAQVRLLRRKLEEYS</u><br><u>HGNLIETVYGLGYRFQPHPTHAEQ</u> |
| ManR (Synechocystis PCC6803) ACCN: WP_010872074 SEQ ID NO: 4 |
| MANILLVDDENALTEPLSKALGHQGHTIDVADQGKTGLAMAIAGQYDLLILDWMLPQVSGLEICRQIRILGH<br>STPVLFLTAKDTLDDRVAGLDAGGDDYLIKPFELRELLARVRALLRRQSHGETITETLGAVKNN<u>LLSVNNV</u><br><u>SLDVANQVAYCQGQRIALSEKEVALLTLFLQAPGQILSHEEIYSHLWPGESPPSSNVLAALVRLLRRKIEQP</u><br><u>NAPRLINSVYGKGYCFEAN</u> |
| BceR (B. subtilis) ACCN: WP_004399109 SEQ ID NO: 5 |
| MFKLLLIEDDESLFHEIKDRLTGWSYDVYGIQDFSQVLQEFAAVNPDCVIIDVQLPKFDGFHWCRLIRSRSN<br>VPILFLSSRDHPADMVMSMQLGADDFIQKPFHFDVLIAKIQAMFRRVHHYNTEPST<u>IKTWCGAAVDAEQNL</u><br><u>VSNDKGSVELTKNEMFILKQLIEQKNKIVSREELIRSLWNDERFVSDNTLTVNVNRLRKKLDALQLGAYIET</u><br><u>KVGQGYIAKEEDKFYD</u> |
| PsdR (B. subtilis) ACCN: WP_003244535 SEQ ID NO: 6 |
| MYRILLVEDDERIASLLGGHLQKYGYEVKIAEQLNDIKLEFAEMKPDLVLLDINLPFFDGFYWCRQIRTISNA<br>PIIFISARTDELNQVMAIENGGDDYITKPFHLEVVMAKIKSVLRRTYGEYSPSLPQESR<u>IVELGGLTIYPDQN</u><br><u>EAEWNSVRILFSQKEFQLLSIFVREHKKIVSRDELLEALWDDVDFVDDNTLTVNVNRLRRKLENAGLTDCIS</u><br><u>TIRGQGYQFQVNRKDEAEC</u> |
| YxdJ (B. subtilis) ACCN: WP_003243527 SEQ ID NO: 7 |
| MNKIMIVEDSEDIRGLLQNYLEKYGYQTVVAADFTAVLDVFLREKPDVVLLDINLPAYDGYYWCRQIRQHS<br>TSPIIFISARSGEMDQVMAIENGGDDYIEKPFSYDIVLAKIKSQIRRAYGEYAAKQGEK<u>VVEYAGVQLFVER</u><br><u>FELRFQDEKSELSKKFSKLLEVLLERGEKVTSRDRLMEKTWDTDIFIDDNTLNVYITRLRKKLRELNAPVSIE</u><br><u>AVRGEGYQLRAQS</u> |
| BAD_0569 (B. adolescentis) ACCN: WP_003808701 SEQ ID NO: 8 |
| MSKPIEASIVVVDDEPSIRELLVASLHFAGFEVNTAASGSEAIEVIERLQPDLIVLDVMLPDIDGFTVTRRIRQ<br>EGITTPVLYLTARDDTQDKVMGLTVGGDDYVTKPFSLEEVVARIRAILRRTQQQVEDDP<u>IIRVGDLEINEDS</u><br><u>HDVSRAGQPIDLSPTEYKLLRYLMDNEGRVLSKAQILDHVWQYDWGGDAAIVESYISYLRKKVDGIVIEDE</u><br><u>NGDKHKVTPLIETKRGIGYMIRAPK</u> |
| Rewired wHTH Response Regulators demonstrated:<br>Key No Style = N-Terminal RR (REC Domain Donor), <u>Underline</u> = C-Terminal RR (DBD Donor) |
| OmpR-CcaR (122aa) SEQ ID NO: 9 |
| MQENYKILVVDDDMRLRALLERYLTEQGFQVRSVANAEQMDRLLTRESFHLMVLDLMLPGEDGLSICRRL<br>RSQSNPMPIIMVTAKGEEVDRIVGLEIGADDYIPKFNPRELLARIRAVLRR<u>GCATCQPVLEWGPIRLDPST</u><br><u>YEVSYDNEVLSLTRKEYSILELLLRNGRRVLSRSMIIDSIWKLESPPEEDTVKVHVRSLRQKLKSAGLSADAI</u><br><u>ETVHGIGYRLANLTEKSLCQGKN</u> |
| OmpR-CcaR (137aa): SEQ ID NO: 10 |
| MQENYKILVVDDDMRLRALLERYLTEQGFQVRSVANAEQMDRLLTRESFHLMVLDLMLPGEDGLSICRRL<br>RSQSNPMPIIMVTAKGEEVDRIVGLEIGADDYIPKFNPRELLARIRAVLRRQANELPGAPSQEEAV<u>LEWG</u><br><u>PIRLDPSTYEVSYDNEVLSLTRKEYSILELLLRNGRRVLSRSMIIDSIWKLESPPEEDTVKVHVRSLRQKLKS</u><br><u>AGLSADAIETVHGIGYRLANLTEKSLCQGKN</u> |

FIGURE 9 Continuation A

OmpR-CcaR (138aa) SEQ ID NO: 11
MQENYKILVVDDDMRLRALLERYLTEQGFQVRSVANAEQMDRLLTRESFHLMVLDLMLPGEDGLSICRRL
RSQSNPMPIIMVTAKGEEVDRIVGLEIGADDYIPKPFNPRELLARIRAVLRRQANELPGAPSQEEAVIEWGP
IRLDPSTYEVSYDNEVLSLTRKEYSILELLLRNGRRVLSRSMIIDSIWKLESPPEEDTVKVHVRSLRQKLKSA
GLSADAIETVHGIGYRLANLTEKSLCQGKN

OmpR-CcaR (139aa) SEQ ID NO: 12
MQENYKILVVDDDMRLRALLERYLTEQGFQVRSVANAEQMDRLLTRESFHLMVLDLMLPGEDGLSICRRL
RSQSNPMPIIMVTAKGEEVDRIVGLEIGADDYIPKPFNPRELLARIRAVLRRQANELPGAPSQEEAVIAWGP
IRLDPSTYEVSYDNEVLSLTRKEYSILELLLRNGRRVLSRSMIIDSIWKLESPPEEDTVKVHVRSLRQKLKSA
GLSADAIETVHGIGYRLANLTEKSLCQGKN

OmpR-CcaR (140aa) SEQ ID NO: 13
MQENYKILVVDDDMRLRALLERYLTEQGFQVRSVANAEQMDRLLTRESFHLMVLDLMLPGEDGLSICRRL
RSQSNPMPIIMVTAKGEEVDRIVGLEIGADDYIPKPFNPRELLARIRAVLRRQANELPGAPSQEEAVIAFGPI
RLDPSTYEVSYDNEVLSLTRKEYSILELLLRNGRRVLSRSMIIDSIWKLESPPEEDTVKVHVRSLRQKLKSA
GLSADAIETVHGIGYRLANLTEKSLCQGKN

OmpR-CcaR (142aa) SEQ ID NO: 14
MQENYKILVVDDDMRLRALLERYLTEQGFQVRSVANAEQMDRLLTRESFHLMVLDLMLPGEDGLSICRRL
RSQSNPMPIIMVTAKGEEVDRIVGLEIGADDYIPKPFNPRELLARIRAVLRRQANELPGAPSQEEAVIAFGKI
RLDPSTYEVSYDNEVLSLTRKEYSILELLLRNGRRVLSRSMIIDSIWKLESPPEEDTVKVHVRSLRQKLKSA
GLSADAIETVHGIGYRLANLTEKSLCQGKN

OmpR-CcaR (150aa) SEQ ID NO: 15
MQENYKILVVDDDMRLRALLERYLTEQGFQVRSVANAEQMDRLLTRESFHLMVLDLMLPGEDGLSICRRL
RSQSNPMPIIMVTAKGEEVDRIVGLEIGADDYIPKPFNPRELLARIRAVLRRQANELPGAPSQEEAVIAFGK
FKLNLGTREVSYDNEVLSLTRKEYSILELLLRNGRRVLSRSMIIDSIWKLESPPEEDTVKVHVRSLRQKLKS
AGLSADAIETVHGIGYRLANLTEKSLCQGKN

OmpR-ManR (137aa) SEQ ID NO: 16
MQENYKILVVDDDMRLRALLERYLTEQGFQVRSVANAEQMDRLLTRESFHLMVLDLMLPGEDGLSICRRL
RSQSNPMPIIMVTAKGEEVDRIVGLEIGADDYIPKPFNPRELLARIRAVLRRQANELPGAPSQEEAVLSVNN
VSLDVANQVAYCQGQRIALSEKEVALLTLFLQAPGQILSHEEIYSHLWPGESPPSSNVLAALVRLLRRKIEQ
PNAPRLINSVYGKGYCFEAN

OmpR-PsdR (137aa) SEQ ID NO: 17
MQENYKILVVDDDMRLRALLERYLTEQGFQVRSVANAEQMDRLLTRESFHLMVLDLMLPGEDGLSICRRL
RSQSNPMPIIMVTAKGEEVDRIVGLEIGADDYIPKPFNPRELLARIRAVLRRQANELPGAPSQEEAVVELGG
LTIYPDQNEAEWNSVRILFSQKEFQLLSIFVREHKKIVSRDELLEALWDDVDFVDDNTLTVNVNRLRRKLEN
AGLTDCISTIRGQGYQFQVNRKDEAEC

OmpR-YxdJ (137aa) SEQ ID NO: 18
MQENYKILVVDDDMRLRALLERYLTEQGFQVRSVANAEQMDRLLTRESFHLMVLDLMLPGEDGLSICRRL
RSQSNPMPIIMVTAKGEEVDRIVGLEIGADDYIPKPFNPRELLARIRAVLRRQANELPGAPSQEEAVVEYAG
VQLEVERFELRFQDEKSELSKKESKLLEVLLERGEKVTSRDRLMEKTWDTDJFIDDNTLNVYITRLRKKLRE
LNAPVSIEAVRGEGYQLRAQS

CcaR-CopR (137aa) SEQ ID NO: 19
MRILLVEDDLPLAETLAEALSDQLYTVDIATDASLAWDYASRLEYDLVILDVMLPELDGITLCQKWRSHSYL
MPILMMTARDTINDKITGLDAGADDYVVKPVDLGELFARVRALLRRGCATCQPVLQVGQWWLDYGTFAV
VTPEQARITLTAKEFQLLEYFMKHPQQILSSEQIKNQLWALSAESTSNVVAAQVRLLRRKLEEYSHGNLIET
VYGLGYRFQPHPTHAEQ

CcaR-ManR (137aa) SEQ ID NO: 20
MRILLVEDDLPLAETLAEALSDQLYTVDIATDASLAWDYASRLEYDLVILDVMLPELDGITLCQKWRSHSYL
MPILMMTARDTINDKITGLDAGADDYVVKPVDLGELFARVRALLRRGCATCQPVLSVNNVSLDVANQVAY
CQGQRIALSEKEVALLTLFLQAPGQILSHEEIYSHLWPGESPPSSNVLAALVRLLRRKIEQPNAPRLINSVY
GKGYCFEAN

CcaR-BceR (137aa) SEQ ID NO: 21
MRILLVEDDLPLAETLAEALSDQLYTVDIATDASLAWDYASRLEYDLVILDVMLPELDGITLCQKWRSHSYL
MPILMMTARDTINDKITGLDAGADDYVVKPVDLGELFARVRALLRRGCATCQPVKTWCGAAVDAEQNLVS
NDKGSVELTKNEMFILKQLIEQKNKIVSREELIRSLWNDERFVSDNTLTVNVNRLRKKLDALQLGAYIETKV
GQGYIAKEEDKFYD

FIGURE 9 Continuation B

CcaR-PsdR (137aa) SEQ ID NO: 22
MRILLVEDDLPLAETLAEALSDQLYTVDIATDASLAWDYASRLEYDLVILDVMLPELDGITLCQKWRSHSYL
MPILMMTARDTINDKITGLDAGADDYVVKPVDLGELFARVRALLRRGCATCQPVVELGGLTIYPDQNEAE
WNSVRILFSQKEFQLLSIFVREHKKIVSRDELLEALWDDVDFVDDNTLTVNVNRLRRKLENAGLTDCISTIR
GQGYQFQVNRKDEAEC

CcaR-YxdJ (137aa): SEQ ID NO: 23
MRILLVEDDLPLAETLAEALSDQLYTVDIATDASLAWDYASRLEYDLVILDVMLPELDGITLCQKWRSHSYL
MPILMMTARDTINDKITGLDAGADDYVVKPVDLGELFARVRALLRRGCATCQPVVEYAGVQLFVERFELR
FQDEKSELSKKESKLLEVLLERGEKVTSRDRLMEKTWDTDIFIDDNTLNVYITRLRKKLRELNAPVSIEAVR
GEGYQLRAQS

BAD_0569-CcaR (137aa): SEQ ID NO: 24
MSKPIEASIVVVDDEPSIRELLVASLHFAGFEVNTAASGSEAIEVIERLQPDLIVLDVMLPDIDGFTVTRRIR
QEGITTPVLYLTARDDTQDKVMGLTVGGDDYVTKPFSLEEVVARIRAILRRTQQQVEDDPVLEWGPIRLD
PSTYEVSYDNEVLSLTRKEYSILELLLRNGRRVLSRSMIIDSIWKLESPPEEDTVKVHVRSLRQKLKSAGLS
ADAIETVHGIGYRLANLTEKSLCQGKN

NarL (E. coli) ACCN: NP_415739 SEQ ID NO: 25
MSNQEPATILLIDDHPMLRTGVKQLISMAPDITVVGEASNGEQGIELAESLDPDLILLDLNMPGMNGLETL
DKLREKSLSGRIVVFSVSNHEEDVVTALKRGADGYLLKDMEPEDLLKALHQAAAGEMVLSEALTPVLAA
SLRANRATTERDVNQLTPRERDILKLIAQGLPNKMIARRLDITESTVKVHVKHMLKKMKLKSRVEAAVWV
HQERIF

UhpA (E. coli) ACCN: NP_418125 SEQ ID NO: 26
MITVALIDDHLIVRSGFAQLLGLEPDLQVVAEFGSGREALAGLPGRGVQVCICDISMPDISGLELLSQLPKG
MATIMLSVHDSPALVEQALNAGARGFLSKRCSPDELIAAVHTVATGGCYLTPDIAIKLASGRQDPLTKRE
RQVAEKLAQGMAVKEIAAELGLSPKTVHVHRANLMEKLGVSNDVELARRMFDGW

YdfI (B. subtilis) ACCN: WP_003244318 SEQ ID NO: 27
MNKVLIVDDHLVVREGLKLLIETNDQYTIIGEAENGKVAVRLADELEPDIILMDLYMPEMSGLEAIKQIKEKH
DTPIIILTTYNEDHLMIEGIELGAKGYLLKDTSSETLFHTMDAAIRGNVLLQPDILKRLQEIQFERMKKQRNE
TQLTEKEVIVLKAIAKGLKSKAIAFDLGVSERTVKSRLTSIYNKLGANSRTEAVTIAMQKGILTIDN

LiaR (B. subtilis) ACCN: WP_003243201 SEQ ID NO: 28
MIRVLLIDDHEMVRMGLAAFLEAQPDIEVIGEASDGSEGVRLAVELSPDVILMDLVMEGMDGIEATKQICR
ELSDPKIIVLTSFIDDDKVYPVIEAGALSYLLKTSKAAEIADAIRAASKGEPKLESKVAGKVLSRLRHSGENA
LPHESLTKRELEILCLIAEGKTNKEIGEEELFITIKTVKTHITNILSKLDVSDRTQAAVYAHRNHLVN

FusR (E. coli) ACCN: AAG54714 SEQ ID NO: 29
MIRVVLVDDHVVVRSGFAQLLSLEDDLEVIGQYSSAAQAWSALIRDDVNVAVIDIAMPDENGLSLLKRLRA
QKPQFRAILSIYDAPTFVQSALDAGASGYLTKRCGPEELVQAVRSVGLGGHYLCADAIRALRGGGQPA
QALEILTPREREVFEELVKGDSVKEIAFKLELSHKTVHVHRANVLGKLNCHSTIELVHFALDHHLLAGH

Rewired HTH Response Regulators:
No Style = N-Terminal RR (REC Domain Donor), Underline = C-Terminal RR (DBD Donor)

NarL-YdfI (131aa) SEQ ID NO: 30
MSNQEPATILLIDDHPMLRTGVKQLISMAPDITVVGEASNGEQGIELAESLDPDLILLDLNMPGMNGLETL
DKLREKSLSGRIVVFSVSNHEEDVVTALKRGADGYLLKDMEPEDLLKALHQAAAGEMVLSPDILKRLQEI
QFERMKKQRNETQLTEKEVIVLKAIAKGLKSKAIAFDLGVSERTVKSRLTSIYNKLGANSRTEAVTIAMQK
GILTIDN

UhpA-YdfI (131aa) SEQ ID NO: 31
MITVALIDDHLIVRSGFAQLLGLEPDLQVVAEFGSGREALAGLPGRGVQVCICDISMPDISGLELLSQLPKG
MATIMLSVHDSPALVEQALNAGARGFLSKRCSPDELIAAVHTVATGGCYLTPDILKRLQEIQFERMKKQR
NETQLTEKEVIVLKAIAKGLKSKAIAFDLGVSERTVKSRLTSIYNKLGANSRTEAVTIAMQKGILTIDN

UhpA-LiaR (131aa) SEQ ID NO: 32
MITVALIDDHLIVRSGFAQLLGLEPDLQVVAEFGSGREALAGLPGRGVQVCICDISMPDISGLELLSQLPKG
MATIMLSVHDSPALVEQALNAGARGFLSKRCSPDELIAAVHTVATGGCYLTSKVAGKVLSRLRHSGENAL
PHESLTKRELEILCLIAEGKTNKEIGEEELFITIKTVKTHITNILSKLDVSDRTQAAVYAHRNHLVN

FusR-YdfI (129aa) SEQ ID NO: 33
MIRVVLVDDHVVVRSGFAQLLSLEDDLEVIGQYSSAAQAWSALIRDDVNVAVIDIAMPDENGLSLLKRLRA
QKPQFRAILSIYDAPTFVQSALDAGASGYLTKRCGPEELVQAVRSVGLGGHYLQPDILKRLQEIQFERMK
KQRNETQLTEKEVIVLKAIAKGLKSKAIAFDLGVSERTVKSRLTSIYNKLGANSRTEAVTIAMQKGILTIDN

FIGURE 9: Amino acid sequences of wild-type (native) and chimeric RRs used herein

BAD_0569-CcaR (137aa): SEQ ID NO: 24
MSKPIEASIVVVDDEPSIRELLVASLHFAGFEVNTAASGSEAIEVIERLQPDLIVLDVMLPDIDGFTVTRRI
RQEGITTPVLYLTARDDTQDKVMGLTVGGDDYVTKPFSLEEVVARIRAILRRTQQQVEDDP<u>VLEWGPI</u>
<u>RLDPSTYEVSYDNEVLSLTRKEYSILELLLRNGRRVLSRSMIIDSIWKLESPPEEDTVKVHVRSLRQKLK
SAGLSADAIETVHGIGYRLANLTEKSLCQGKN</u>

Native HTH Response Regulators:
  i) Key No Style = REC Domain, Bold = Linker, <u>Bold Underline</u> = Flexible alpha 6, <u>Underline</u> = DBD

NarL (E. coli) ACCN: NP_415739 SEQ ID NO: 25
MSNQEPATILLIDDHPMLRTGVKQLISMAPDITVVGEASNGEQGIELAESLDPDLILLDLNMPGMNGLE
TLDKLREKSLSGRIVVFSVSNHEEDVVTALKRGADGYLLKDMEPEDLLKALHQAAAGEMVLS<u>EALTPV</u>
<u>LAASLRANRATTERDVN**QLTPRERDILKLIAQGLPNKMIARRLDITESTVKVHVKHMLKKMKLKSRVEA
AVWVHQERIF**</u>

UhpA (E. coli) ACCN: NP_418125 SEQ ID NO: 26
MITVALIDDHLIVRSGFAQLLGLEPDLQVVAEFGSGREALAGLPGRGVQVCICDISMPDISGLELLSQLP
KGMATIMLSVHDSPALVEQALNAGARGFLSKRCSPDELIAAVHTVATGGCYLT<u>PDIAIKLASGRQDPLT
KRERQVAEKLAQGMAVKEIAAELGLSPKTVHVHRANLMEKLGVSNDVELARRMFDGW</u>

YdfI (B. subtilis) ACCN: WP_003244318 SEQ ID NO: 27
MNKVLIVDDHLVVREGLKLLIETNDQYTIIGEAENGKVAVRLADELEPDIILMDLYMPEMSGLEAIKQIKE
KHDTPIILTTYNEDHLMIEGIELGAKGYLLKDTSSETLFHTMDAAIRGNVLLQ<u>PDILKRLQEIQFERMKK
QRNETQLTEKEVIVLKAIAKGLKSKAIAFDLGVSERTVKSRLTSIYNKLGANSRTEAVTIAMQKGILTIDN</u>

LiaR (B. subtilis) ACCN: WP_003243201 SEQ ID NO: 28
MIRVLLIDDHEMVRMGLAAFLEAQPDIEVIGEASDGSEGVRLAVELSPDVILMDLVMEGMDGIEATKQI
CRELSDPKIIVLTSFIDDDKVYPVIEAGALSYLLKTSKAAEIADAIRAASKGEPKLE<u>SKVAGKVLSRLRHS
GENALPHESLTKRELEILCLIAEGKTNKEIGEELFITIKTVKTHITNILSKLDVSDRTQAAVYAHRNHLVN</u>

FusR (E. coli) ACCN: AAG54714 SEQ ID NO: 29
MIRVVLVDDHVVVRSGFAQLLSLEDDLEVIGQYSSAAQAWSALIRDDVNVAVIDIAMPDENGLSLLKRL
RAQKPQFRAIILSIYDAPTFVQSALDAGASGYLTKRCGPEELVQAVRSVGLGGHYLC<u>ADAIRALRGGG
QPAQALE**ILTPREREVFELLVKGDSVKEIAFKLELSHKTVHVHRANVLGKLNCHSTIELVHFALDHHLLA
GH**</u>

Rewired HTH Response Regulators:
No Style = N-Terminal RR (REC Domain Donor), <u>Underline</u> = C-Terminal RR (DBD Donor)

NarL-YdfI (131aa) SEQ ID NO: 30
MSNQEPATILLIDDHPMLRTGVKQLISMAPDITVVGEASNGEQGIELAESLDPDLILLDLNMPGMNGLE
TLDKLREKSLSGRIVVFSVSNHEEDVVTALKRGADGYLLKDMEPEDLLKALHQAAAGEMVLS<u>PDILKRL
QEIQFERMKKQRNETQLTEKEVIVLKAIAKGLKSKAIAFDLGVSERTVKSRLTSIYNKLGANSRTEAVTIA
MQKGILTIDN</u>

UhpA-YdfI (131aa) SEQ ID NO: 31
MITVALIDDHLIVRSGFAQLLGLEPDLQVVAEFGSGREALAGLPGRGVQVCICDISMPDISGLELLSQLP
KGMATIMLSVHDSPALVEQALNAGARGFLSKRCSPDELIAAVHTVATGGCYLT<u>PDILKRLQEIQFERMK
KQRNETQLTEKEVIVLKAIAKGLKSKAIAFDLGVSERTVKSRLTSIYNKLGANSRTEAVTIAMQKGILTID
N</u>

UhpA-LiaR (131aa) SEQ ID NO: 32
MITVALIDDHLIVRSGFAQLLGLEPDLQVVAEFGSGREALAGLPGRGVQVCICDISMPDISGLELLSQLP
KGMATIMLSVHDSPALVEQALNAGARGFLSKRCSPDELIAAVHTVATGGCYLT<u>SKVAGKVLSRLRHSG
ENALPHESLTKRELEILCLIAEGKTNKEIGEELFITIKTVKTHITNILSKLDVSDRTQAAVYAHRNHLVN</u>

FusR-YdfI (129aa) SEQ ID NO: 33
MIRVVLVDDHVVVRSGFAQLLSLEDDLEVIGQYSSAAQAWSALIRDDVNVAVIDIAMPDENGLSLLKRL
RAQKPQFRAIILSIYDAPTFVQSALDAGASGYLTKRCGPEELVQAVRSVGLGGHYL<u>QPDILKRLQEIQF
ERMKKQRNETQLTEKEVIVLKAIAKGLKSKAIAFDLGVSERTVKSRLTSIYNKLGANSRTEAVTIAMQKG
ILTIDN</u>

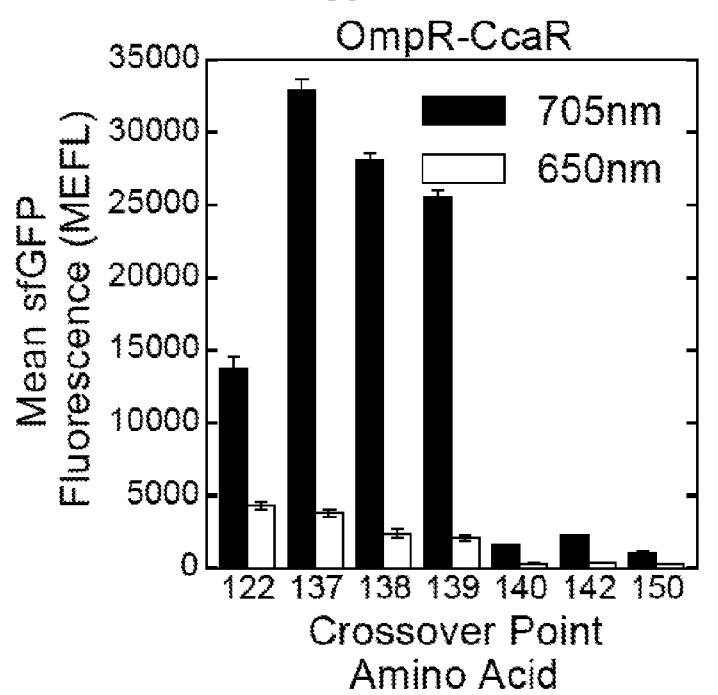
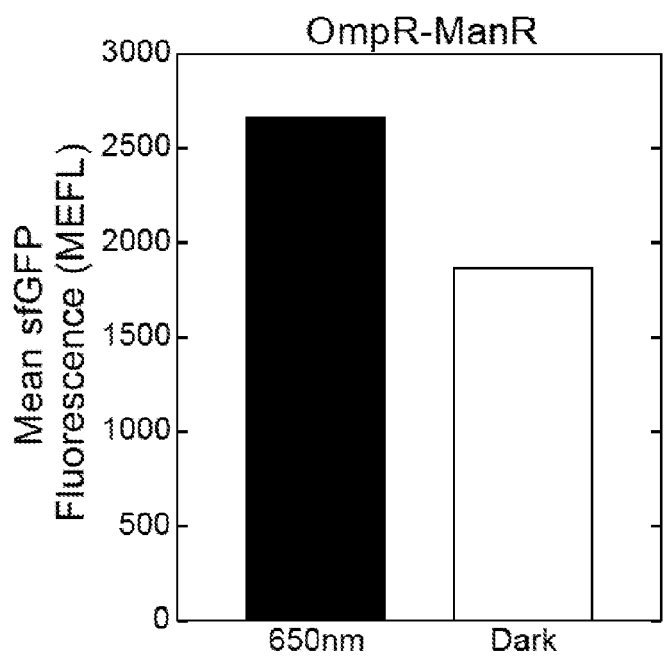

G6P Transfer Function
UhpB/UhpA-Ydfl | $P_{ydfJ-115}$

G6P Transfer Function
UhpB/UhpA-LiaR | $P_{yhc-86}$

FIGURE 28
Partial listing of embodiments, any one of which can be combined with any other one or more or portions thereof.

A genetically engineered bacteria, comprising:
a modified heterologous two component sensor system (TCS) from a different species of bacteria, said TCS being a member of a members of a OmpR-PhoB or NarL-FixJ family of two component sensor kinases, said TCS comprising:
    a sensor kinase (SK) comprising a ligand binding domain operably coupled to a kinase domain, and
    a modified response regulator (RR) that is cognate to said SK, said RR comprising a cognate receiver domain (REC) operably coupled to a heterologous DNA binding domain (DBD) of known functionality, and
a reporter gene under the control of a DNA binding site that binds said DBD, such that said reporter gene is expressed when said SK activates said modified RR and said DBD binds to said DNA binding site.

A genetically engineered bacteria, comprising:
a modified heterologous two component sensor system (TCS) from a different species of bacteria, said TCS comprising:
    a sensor kinase (SK) comprising a ligand binding domain operably coupled to a kinase domain, and
    a modified response regulator (RR) that is cognate to said SK, said RR comprising a cognate receiver domain (REC) operably coupled to a non-cognate DNA binding domain (DBD) of known functionality, and
a reporter gene under the control of a DNA binding site that binds said DBD, such that said reporter gene is expressed when said SK activates said modified RR by phosphorylating said REC domain and said DBD binds to said DNA binding site.

A genetically engineered bacteria, comprising:
a modified heterologous two component sensor system (TCS) from a different species of bacteria, said TCS being a member a OmpR-PhoB or a NarL-FixJ family of two component sensor kinases, said TCS comprising:
    a sensor kinase (SK) comprising a ligand binding domain operably coupled to a kinase domain, and
    a modified response regulator (RR) that is cognate to said SK, said RR comprising a cognate receiver domain (REC) operably coupled to a non-cognate DNA binding domain (DBD) of known functionality, and
a reporter gene under the control of a DNA binding site that binds said DBD, such that said reporter gene is expressed when said SK activates said modified RR and said DBD binds to said DNA binding site.

A genetically engineered bacteria, comprising:
a modified two component sensor system (TCS), said TCS comprising:
a wild type sensor kinase (SK) comprising a ligand binding domain operably coupled to a kinase domain, and
a modified response regulator (RR) that is cognate to said SK, said RR comprising a cognate receiver domain (REC) operably coupled to a non-cognate DNA binding domain (DBD) of known functionality, and
a reporter gene under the control of a promoter element containing an operator site that is bound by said DBD, such that said reporter gene is activated or repressed when said SK signals to said modified RR and said DBD binds to said DNA binding site.

FIGURE 28 Continuation A

Partial listing of embodiments, any one of which can be combined with any other one or more or portions thereof.

| |
|---|
| A genetically engineered bacteria, comprising: a modified two component sensor system (TCS), said TCS being a member of a OmpR-PhoB or a NarL-FixJ family of two component sensor kinases, said TCS comprising: <br>    a sensor kinase (SK) comprising a ligand binding domain of unknown input operably coupled to a kinase domain, and <br>    a modified response regulator (RR) that is cognate to said SK, said RR comprising a cognate receiver domain (REC) operably coupled to a non-cognate DNA binding domain (DBD) of known functionality, and <br>a reporter gene under the control of a DNA binding site that binds said DBD, such that said reporter gene is activated or repressed when said SK signals to said modified RR and said DBD binds to said DNA binding site; <br>wherein said REC is separated from its wild type DBD at a crossover site between amino acids 110-155, said amino acids numbered according to alignment with either wild type OmpR or wild type NarL, depending whether the TCS belongs to the OmpR-PhoB or the NarL-FixJ family, respectively. |
| A genetically engineered bacteria, said bacteria expressing a two component sensor system (TCS) comprising i) a sensor kinase gene comprising a ligand binding domain operably coupled to a kinase domain, and ii) a response regulator gene comprising a receiver domain operably coupled to an heterologous DNA binding domain (DBD), said bacteria also comprising a DNA binding site that binds said DBD that is operably coupled to a reporter gene. |
| A genetically engineered gram positive bacteria expressing a two component sensor system (TCS) from a gram negative bacteria, said TCS comprising a sensor kinase gene and a response regulator gene. Preferably the SK of any bacteria herein described is wild type and the non-cognate DBD is compatible with the host bacteria. |
| A genetically engineered gram positive bacteria expressing a two component sensor system (TCS) from a gram negative bacteria, said TCS comprising a sensor kinase (SK) gene and a response regulator (RR) gene (or vice versa). Preferably, the DBD of the RR is a non-cognate DBD operably fused to the REC domain, which remains cognate to the SK. |
| A bacteria as described, a single expression vector encoding both said SK and said modified RR. |
| A bacteria as described, said reporter gene being encoded on an expression vector. |
| A bacteria as described, said reporter gene being integrated into a genome of said bacteria. |
| A bacteria as described, said response regulator gene encoding a receiver domain operably coupled to a heterologous DBD, said bacteria also comprising a DNA targeted by said DBD that is operably coupled to a reporter gene. |
| A bacteria as described, where said bacteria is gram positive and said TCS is from a gram negative species, or vice versa. |
| A bacteria as described, where said bacteria is gram positive and said TCS is from a gram negative species, or vice versa. |
| A bacteria as described, wherein said SK and RR are members of a OmpR-PhoB family of TCSs or a member of a NarL-FixJ family of TCSs. |
| A bacteria as described, wherein said SK and RR are members of a OmpR-PhoB family of TCSs or a member of a NarL-FixJ family of TCSs. |
| A bacteria as herein described, where said bacteria is the same bacterium wherein which said TCS evolved, and a native SK and RR of said TCS is knocked out. |

FIGURE 28 Continuation B
Partial listing of embodiments, any one of which can be combined with any other one or more or portions thereof.

| |
|---|
| A bacteria as herein described, wherein: said TCS is a member of a OmpR-PhoB family and said REC is separated from its wild type DBD at a crossover site between amino acids 110 and 151, preferably 122, 137, 138 or 139, said amino acids numbered according to alignment with wild type OmpR, or said TCS is a member of a NarL-FixJ family and said REC is separated from its wild type DBD at a crossover site between amino acids 110 and 155, preferably 113, 127, 130, 132, 142 or 154, said amino acids numbered according to alignment with wild type NarL. Preferably, wherein no exogenous linker peptide is used between said REC and said non-cognate DBD. Preferably the non-cognate DBD is also cut at the same crossover site, although sites nearby may suffice. |
| A biosensor for a ligand, said biosensor comprising a bacteria expressing a two component sensor system (TCS), said TCS comprising a sensor kinase gene encoding a ligand binding domain that binds said ligand operably coupled to a kinase domain, and a response regulator encoding a receiver domain that is activated by said kinase domain operably coupled to a heterologous DNA binding domain that can change expression of a reporter gene, also found in said bacteria. |
| A method of identifying an input signal that activates a sensor kinase, comprising applying a test input signal to a genetically engineered bacteria, comprising: a modified two component sensor system (TCS), said TCS being a member of a OmpR-PhoB or a NarL-FixJ family of two component sensor kinases, said TCS comprising: a wild type sensor kinase (SK) comprising a ligand binding domain having an unknown input signal operably coupled to a kinase domain; a modified response regulator (RR) that is cognate to said SK, said RR comprising a cognate receiver domain (REC) operably coupled to a non-cognate DNA binding domain (DBD) of known functionality; a reporter gene under the control of a operator site that binds said DBD, such that said reporter gene is activated or repressed when said SK signals to said modified RR and said DBD binds to said operator site; wherein said REC is separated from its wild type DBD at a crossover site between amino acids 110-155, said amino acids numbered according to alignment with either wild type OmpR or wild type NarL, depending whether the TCS belongs to the OmpR-PhoB or the NarL-FixJ family, respectively; and wherein no exogenous linker peptide is used between said REC and said non-cognate DBD; determining whether said input signal changes expression of said reporter gene, and repeating applying and determining steps until an input signal that changes said reporter gene expression is identified, thereby identifying a cognate input signal for said TCS. |
| A method of making a biosensor, comprising applying a test input signal to a bacteria as herein described, determining whether said test input signal changes expression of said reporter gene, and repeating applying and determining steps until an input signal that changes said reporter gene expression is identified, confirming that said identified input signal is the input signal for said TCS; culturing said bacteria in an environment, and |

FIGURE 28 Continuation C
Partial listing of embodiments, any one of which can be combined with any other one or more or portions thereof.

| |
|---|
| monitoring expression of said reporter gene, wherein a change in said reporter gene expression indicates that said confirmed input signal is present in said environment. |
| A method of making a biosensor, said method comprising engineering a bacteria to have:<br>a reporter gene under the control of a promoter,<br>a heterologous two component system (TCS) comprising a sensor kinase (SK) and a cognate response regulator (RR), said TCS comprising:<br>    an operable SK having a known input ligand;<br>    an operable rewired RR having a cognate REC domain for said SK operably fused to a non-cognate DBD that activates said promoter,<br>wherein presence of an input ligand in an environment in which said bacteria resides is detected by expression of said reporter gene. |
| A method of making a biosensor, said method comprising engineering a bacteria to have:<br>a reporter gene under the control of a promoter,<br>a heterologous two component system (TCS) comprising a sensor kinase (SK) and a cognate response regulator (RR), said TCS comprising:<br>    an operable SK having a known input signal;<br>    an operable rewired RR having a cognate REC domain for said SK operably fused to a non-cognate DBD that changes expression of said promoter,<br>wherein presence of said known input signal in an environment in which said bacteria resides is detected by a change in expression of said reporter gene. |
| A method of making a modified RR, comprising obtaining a gene for a RR from a of a OmpR-PhoB or NarL-FixJ family of two component sensor kinases, cutting said gene at a site corresponding to a domain separation site between amino acids 110 and 151, preferably at amino acid 122, 137, 138 or 139, said amino acids numbered according to alignment with wild type OmpR, and operably coupling an REC domain 5' of said domain separation site to a non-cognate DBD of known functionality. Preferably, the non-cognate DBD is cut at or near the same crossover site. |
| A method of screening for a ligand that activates a sensor kinase, comprising i) applying a test ligand to the bacteria described herein, ii) determining whether said ligand activates said reporter gene, and iii) repeating steps i and ii until a ligand that activates said reporter gene expression is identified. |
| A method of screening for an input that activates a sensor kinase, comprising<br>g) applying a test input to the bacteria as described,<br>h) determining whether said input activates expression of said reporter gene, and<br>i) repeating steps a and b until an input that activates said reporter gene expression is identified. |

IDENTIFYING LIGANDS FOR BACTERIAL SENSORS

PRIOR RELATED APPLICATIONS

This application is a National Phase under 35 U.S.C. § 371 of International Application PCT/US2016/30831, filed May 4, 2016, which claims priority to U.S. Ser. No. 62/157, 293, IDENTIFYING LIGANDS FROM BACTERIAL SENSORS, filed May 5, 2015. Both applications are expressly incorporated by reference herein in their entirety for all purposes.

FEDERALLY SPONSORED RESEARCH STATEMENT

This invention was made with government support under N00014-14-1-0487 awarded by the Office of Naval Research. The government has certain rights in the invention. This invention was also supported by Grant No. C-1856, awarded by the Welch Foundation.

FIELD OF THE DISCLOSURE

The invention is a method to replace the DNA binding domains and output promoters bacterial two component signal transduction systems (a.k.a. two component systems, two component sensors, sensors, TCSs). The method enables TCSs to be transferred between different bacterial species despite incompatibilities that otherwise 'silence' their ability to respond to inputs. The method can also be used to identify the inputs of novel or poorly characterized TCSs by transporting the TCSs from their native bacteria to non-native laboratory strains, encoding reporter genes as outputs, and performing screens wherein outputs are measured in the presence of different possible input signals. The method also enables TCSs to be engineered to function as biosensors with numerous applications in medicine, industry, and basic science.

BACKGROUND OF THE DISCLOSURE

In the field of molecular biology, a two-component system serves as a basic stimulus-response coupling mechanism to allow organisms to sense and respond to changes in many different environmental conditions. A TCS typically consists of a membrane-bound sensor histidine kinase (SK) that senses a specific environmental stimulus and a corresponding response regulator (RR) that mediates the cellular response, mostly through differential expression of target genes. TCSs are widespread and highly evolutionarily diversified in the genomes of prokaryotes, but only a few TCSs have been identified in eukaryotic organisms.

Typically, signal transduction occurs through the transfer of phosphoryl groups from adenosine triphosphate (ATP) to a conserved histidine residue in the SK. This is an autophosphorylation reaction. The RRs are phosphorylated on a conserved aspartate residue and are protein phosphatases for the SKs. Phosphorylation causes a change in the RR conformation, usually activating an attached output domain, which then leads to the activation (or repression) of transcription of target genes. The phosphorylation state of an RR thereby controls its activity. Some SKs are bi-functional, catalyzing both the phosphorylation and dephosphorylation of their cognate RR. Inputs can regulate either the kinase or phosphatase activity of the bi-functional SK.

Signal transduction can also occur in a phosphorylation-independent manner. For example the SK can sequester the RR at the membrane in the absence of input. In the presence of input, the SK may then release the RR, which may then bind DNA and activate or repress transcription.

Two-component systems enable bacteria to sense, respond, and adapt to a wide range of environments, stressors, and growth conditions. Some bacteria can contain up to as many as 200 TCSs that have tight molecular specificity to prevent unwanted cross-talk. These pathways have been adapted to respond to a wide variety of stimuli, including nutrients, cellular redox state, changes in osmolarity, quorum sensing signals, antibiotics, temperature, chemoattractants, pH and more.

A few examples are provided:

In *Escherichia coli*, the EnvZ-OmpR osmoregulation system controls the differential expression of the outer membrane porin proteins OmpF and OmpC.

The KdpD-KdpE two-component regulatory system regulates the kdpFABC operon responsible for potassium transport in bacteria including *E. coli* and *Clostridium acetobutylicum*. The N-terminal domain of KdpD forms part of the cytoplasmic region of the protein, which may be the sensor domain responsible for sensing turgor pressure.

One variation of the two-component system is the phospho-relay system. In this system, a hybrid SK autophosphorylates and then transfers the phosphoryl group to an internal receiver domain, rather than to a separate RR protein. The phosphoryl group is then shuttled to histidine phosphotransferase (HPT) and subsequently to a terminal RR, which can evoke the desired response.

Signal transducing SKs are the key elements in TCSs. Examples of SKs are EnvZ, which plays a central role in osmoregulation, and CheA, which plays a central role in the chemotaxis system.

SKs usually have an N-terminal ligand-binding domain and a C-terminal kinase domain, but other domains may also be present. The N-terminal domain may also be a protein-protein interaction domain that enables activation of the SK by interaction with a third protein that binds the input, or another type of sensory domain. The kinase domain is responsible for the autophosphorylation of the histidine with ATP, the phosphotransfer from the kinase to an aspartate of the RR, and (with bi-functional enzymes) the phosphotransfer from aspartyl phosphate back to water. The kinase core has a unique fold, distinct from that of the Ser/Thr/Tyr kinase superfamily.

SKs can be roughly divided into two classes: orthodox and hybrid. Most orthodox SKs, typified by the *E. coli* EnvZ protein, function as periplasmic membrane receptors and have a signal peptide and transmembrane segment(s) that separate the protein into a periplasmic N-terminal sensing domain and a highly conserved cytoplasmic C-terminal kinase core. Members of this family, however, have an integral membrane sensor domain. Not all orthodox kinases are membrane bound, e.g., the nitrogen regulatory kinase NtrB (GlnL) is a soluble cytoplasmic SK.

Hybrid SKs contain multiple phosphodonor and phosphoacceptor sites and use multi-step phospho-relay schemes instead of promoting a single phosphoryl transfer. In addition to the sensor domain and kinase core, they contain a CheY-like receiver domain and a His-containing phosphotransfer (HPt) domain.

TCSs are highly evolutionarily diversified and have been shown to sense diverse chemical and physical inputs such as ions, sugars, polysaccharides, oxygen, antimicrobial peptides, human hormones, light, and so on. TCSs also regulate a wide range of different gene outputs and theoretically can regulate any gene output. In addition, a single bacterial cell can have hundreds of different TCSs, enabling multiplexed sensing.

It is trivial to identify TCSs from bacterial genome sequences by computational methods, such as homology and/or domain searching and the fact that most SKs reside <1000 base pairs from the RRs with which they communicate (i.e. their cognate RRs). However, such TCSs typically sense unknown inputs and control unknown output genes. In particular, output genes are more difficult to identify from genome sequences because they do not have a conserved sequence or domain structure that can be predicted from the sequence of the SK or RR. Moreover, output genes more often reside greater distances away from the SK and RR on the genome, making their identification difficult. Because output genes cannot be easily identified, they cannot be easily measured in response to different possible input signals, making inputs difficult to identify. Furthermore, the microbes containing most TCSs are un-culturable or difficult to genetically manipulate in the laboratory, further making inputs difficult to identify. Moreover, many TCSs are recalcitrant to transfer from their native strains to non-native bacteria such as laboratory strains due to incompatibilities between the transcription regulating DNA binding domain or output promoter and the transcriptional machinery (e.g. RNA Polymerase) of the non-native strain. Therefore, while TCSs have tremendous medical, industrial and basic research applications, various technical challenges have kept them from being fully exploited.

There have been a very small number of limited publications where small scale DNA binding domain (DBD) replacement has been shown for a small number of TCSs. However, those reports do not use DBD replacement to identify the inputs of the TCSs, but rather to study the fundamental structural and functional biology of the RR. These studies also do not demonstrate DBD replacement for multiple members of the OmpR-PhoB family, nor any members of the NarL-FixJ family, nor identify general primary or secondary structural "rules" for rewiring the DBD of those structural sub-families, as we do. They also do not use the method to transport TCSs to new species of bacteria where they can be studied without complicating and potentially obfuscating cross-regulation from poorly understood native regulatory networks. Importantly, they do not use the method to engineer biosensors.

In a related, but fundamentally different approach, Skerker et al. (2008) swap the SK-RR interaction interface of very closely related TCSs. The SK-RR interface is a different site than is rewired herein. Their data show molecular interaction and phosphotransfer activity in vitro and in vivo, but they do not show that the rewired TCS responds to an input. Thus, in direct contrast to the rewired TCSs described herein, the rewired TCSs in Skerker are not fully functional. Accordingly, one could not utilize the Skerker technology to identify the input of a TCS. Cheng (2014) takes a similar approach to Skerker, but all results are theoretical, not experimental. Furthermore, their focus is on the nature of the molecular interactions rather than the applications of rewired TCSs.

Wang et al. (2013) describes an idea for DBD rewiring for the NtrC subfamily of RRs, not the OmpR-PhoB and NarL-FixJ families. OmpR-PhoB and NarL-FixJ are much more widespread than NtrC, thus our method has broader scope for our applications. However, Wang et al. (2013) show no data, and thus there is no reasonable expectation of success in the absence of any proof of concept. Finally, Wang et al. claim that one should "design linkers" (i.e. non-native linkers) between REC and DBD. Non-native or exogenous linkers are not needed herein—we use only the native linker sequences. Stated another way, we literally cut and paste regions of existing RR sequences together, we add no unnatural sequences to our chimeric RRs. Wang also specifically states they are not interested in engineering "one input/one output" TCSs. On the other hand, we are precisely interested in engineering "one input/one output" TCSs. Furthermore, they do not say their method could be used to move TCSs between species, nor that their method could be used to identify the ligands sensed by TCSs. Rather, they want to use TCSs with known signals to control non-natural genes in order to study the natural genes that are regulated by the TCSs.

There are examples of rewiring in the OmpR-PhoB family. For example, Allen (2001) replaces the REC domain of the OmpR-PhoB family E. coli RR PhoB with that of the chemotaxis responsive RR CheY. They use mutant E. coli strains where the chemotaxis pathway is strongly activated or strongly de-activated to show that one of the CheY-PhoB chimeras activates a PhoB output promoter only in the former strain.

Walthers (2003) also construct chimeras between the REC domains of OmpR and PhoB and the DBDs of OmpR and PhoB. PhoB-OmpR chimeras fail to activate gene expression, but OmpR-PhoB chimeras did activate gene expression.

Howell (2003) rewires the DNA binding domain (DBD) of PhoP (OmpR-PhoB family) with that of YycF (OmpR-PhoB), both from B. subtilis, and all experiments are in B. subtilis. In this experiment, they replace the DBD of a TCS with a known input and output, with the DBD of a TCS with an unknown output. Then they use the known input for TCS 1 to identify the unknown outputs of TCS 2—the goal being to understand the fundamental biology of the gene regulatory outputs of a TCS.

Tapparel (2006) replace the REC domain of E. coli CpxR (OmpR-PhoB family) with several others, but all chimeras are constitutively active. That is, they fail to achieve functional, switchable chimeras.

None of the above use DBD rewiring to identify unknown inputs for the TCS pair, nor can they then construct biosensors for those identified inputs using the new constructions.

Thus, what is needed in the art are simple, reliable methods of identifying two component system inputs and engineering them to function as biosensors. It would also be beneficial to identify several useful crossover points for making functional hybrids, and to be able to transport two component systems between bacterial species, ensuring transcriptional compatibility of the transported two component system with the new bacterium.

SUMMARY OF THE DISCLOSURE

The general purpose of this disclosure is to re-engineer naturally evolved bacterial two component signal transduction systems (a.k.a. two component systems or two component sensors, TCSs) to transport them between different bacterial species, discover the inputs (chemicals, metabolites, hormones, environmental pollutants, industrial compounds, other bacteria, mechanical, or physical stimuli, etc.) that they sense, and enable their use as biosensors for scientific, industrial, medical, defense, environmental and other applications.

TCSs are a family of protein-based signaling pathways and the primary means by which bacteria sense and respond to the environment. Canonical TCSs consist of a "sensor histidine kinase" or "SK" and a "response regulator" or "RR". The canonical SK is embedded in the inner bacterial membrane. It contains a "sensor domain" that faces the extracellular environment (or periplasm in the case of gram negative bacteria), and a "transmembrane domain" that transmits information into an intracellular (cytoplasmic) histidine kinase "signaling domain." In the presence of the cognate input stimulus (hereinafter "input" or "input signal" or "ligand"), the sensor domain changes conformation. This conformational change is transmitted to the signaling domain by way of the transmembrane domain. The signaling domain is then activated, causing it to phosphorylate (chemically modify) itself on a specific histidine residue. The phosphoryl group is then transferred to a specific (cognate) non-membrane associated (cytoplasmic) RR, which then changes the expression of its target proteins. Some SKs can have cytoplasmic sensor domains. Others can be completely cytoplasmic (i.e. not membrane associated).

For canonical RRs, each RR has two domains, an N-terminal "REC" or "receiver" domain, which is phosphorylated by the SK, and a C-terminal DNA binding domain ("DBD") that binds to the output promoter(s). The phosphorylated RR (known as RR-P) changes (activates or deactivates) expression of one or more specific gene(s). In this way, bacteria can sense and then respond to stimuli in the environment.

We have developed a combined computational/experimental method to discover what virtually any TCS senses, or at least the orthodox TCSs. We have also shown that we can use this method to transport TCSs between species of bacteria while retaining their sensing, signaling and tranScriptional regulatory functions—which facilitates the identification of their inputs and their use as biosensors. This method also allows us to engineer novel biosensors from the newly characterized TCSs.

First, we use modern synthetic biology methods such as DNA synthesis or PCR and gene assembly methods to express computationally identified (by homology search and analysis of organization of TCS genes within bacterial genomes) TCSs in standard laboratory bacteria, such as the gram-negative organism *E. coli* and the gram-positive organism *B. subtilis*.

We have identified several specific amino acid residues in the two most widespread structural families, OmpR-PhoB (aka winged Helix-Turn-Helix; wHTH) and NarL-FixJ (aka Helix-Turn-Helix; HTH), of DNA-binding RRs wherein the DBD can be "swapped" for a well characterized DBD with a known output promoter (See FIG. 23, FIG. 24, FIG. 25, FIG. 26, and FIG. 27). We have engineered a suite of well-characterized DBDs and promoters that work in *E. coli* and *B. subtilis* in our laboratory, providing multiple options for rewiring the DBDs of any given TCS from the wHTH and HTH families.

Although the input of a novel TCS initially remains unknown, we can "rewire" that TCS to control a known output promoter. Then, by expressing any number of standard "reporter genes", such as Green Fluorescent Protein (GFP), from the known output promoter, we can monitor the activity of any TCS in *E. coli* or *B. subtilis* or other bacteria by standard laboratory methods. If the TCS is non-functional in the new organism, we can rewire its DBD to make it functional. See FIG. 19.

There are a great variety of reporter genes that can be used herein, and GFP is only one convenient reporter. The amount or activity of the reporter protein produced is taken as a proxy for the TCS response to the target. Ideal reporter proteins are easy to detect and quantify (preferably noninvasively), highly sensitive and, ideally, not present in the native organism. They can be set up to detect either activation or deactivation. Several currently popular reporter proteins and their characteristics are listed in TABLE 1.

TABLE 1

Common spectroscopically active reporter proteins and their detection

| Reporter Protein | Reporter genes | Origin | Substrate | Detection method | Comments | Refs |
|---|---|---|---|---|---|---|
| Bacterial luciferase | luxAB* or luxCDABE | Bioluminescent bacteria* | $O_2$, FMNH2, and long-chain aldehydes | Bioluminescence | Requires $O_2$; aldehyde addition is required if only luxAB is used | 94, 95 |
| Firefly luciferase | lucFF | Firefly (*photinus pyralis*) | $O_2$, ATP and luciferin | Bioluminescence | Requires $O_2$ | 96 |
| Click beetle luciferase | lucGR | Click beetle (*Pyrophorus plagiophthalamus*) | $O_2$, ATP and pholasin | Bioluminescence | Requires $O_2$ | 97 |
| *Renilla* luciferase | Rluc | *Renilla reniformis* | Coelenterazine and $Ca^{2+}$ | Bioluminescence | Requires $O_2$ | 98 |
| β-Galactosidase | lacZ | *Escherichia coli* | Galactopyranosides† | Chemiluminescence, colorimetry, electrochemistry and fluorescence | External substrate addition (may require cell permeabilization) | 1 |
| Fluorescent proteins | gfp, etc. | *Aequorea victoria* and additional marine invertebrates | N/A | Fluorescence | $O_2$ is required for maturation; different colour varieties exist | 99-101 |
| Spheroidene monooxygenase | crtA | *Rhodovulum sulfidophilum* | Spheroidene | Colorimetry | None | 102 |
| Infrared fluorescent proteins | Various | Bacteriophytochrome family | N/A | Fluorescence | None | 103 |

TABLE 1-continued

Common spectroscopically active reporter proteins and their detection

| Reporter Protein | Reporter genes | Origin | Substrate | Detection method | Comments | Refs |
|---|---|---|---|---|---|---|
| FMN-based fluorescent proteins | Various | Engineered from *Bacillus subtilis* and *Pseudomonas putida* | None | Fluorescence | Functional in both oxic and anaoxic conditions; requires endogenous FMN | 104 |

NA, not applicable.
*Most commonly used species include *Aliivibrio fischeri* (also known as *Vibrio fischeri*), *Vibrio harveyi* and *Photorhabdus luminescens*.
†For example, O-nitrophenyl-β-D-galactophyranoside (X-gal), 4-methylumbelliferyl-β-D-galactophyranoside, 4-aminophenyl-β-D-galactopyranoside and D-luciferin-O-β-galactopyranoside Using the amount of reporter gene expression as a read-out, and using standard high throughput screening methods, such as fluorimetry or flow cytometry, we can screen the novel TCS against virtually any chemical or physical input, and very easily measure those chemicals or input signals that it senses, using standard, high throughput laboratory assays.

As used herein, a "two component system", "two component signal transduction system", "two component sensor", "two component sensor system", or "TCS" is understood to be a two protein system including a sensor kinase and a response regulator, wherein the sensor kinase changes activity in response to a cognate input, resulting in a change in phosphorylation of the cognate response regulator by the sensor kinase, which then activates or de-activates transcription from the cognate output promoter(s) and thereby expression of relevant downstream proteins.

As used herein, "cognate" means the two (or more) parts function together. Non-cognate, by contrast, means a component that, under normal circumstances, would not function together with a given SK, although we subsequently rewire non-cognate DBD to be recognized by a SK by DBD swapping. Nonetheless, "non-cognate" indicates its origins from a non-cognate system.

As used herein, a sensor kinase is a protein understood to have a ligand binding domain ("LBD") or similar input mechanism operably coupled to a kinase domain (KD), such that when the LBD binds its cognate ligand or sensor input, the kinase is activated.

As used herein, a "response regulator" or "RR" typically has a "receiver" or "REC" domain that is activated by the active kinase of the SK. Typically, the REC domain is operably coupled to a DNA binding domain or DBD, which thus can bind to and turn on relevant downstream protein expression.

As used herein, a "non-cognate DBD" means a DBD that comes from another protein, not the response regulator that the REC domain comes from. Typically, the DBD then binds to the DNA it is targeted to, which is itself coupled to a reporter gene that can easily be detected.

As used herein, an OmpR-PhoB family TCS is a TCS containing an RR which has 40% or greater amino acid sequence identity to OmpR (FIG. 9).

As used herein, a NarL-FixJ family of TCS is a TCS containing an RR, which has 40% or greater amino acid sequence identity to NarL (FIG. 9).

As used herein, a "crossover site" is a site where in the two domains (REC & DBD) of the RR can be successfully separated and a non-cognate DBD fused to the REC domain. Exemplary crossover sites are shown in FIG. 10, FIG. 23, FIG. 24, FIG. 25, FIG. 26, and FIG. 27.

Preferably, the REC and DBD domains are separated at the crossover site, and recoupled in frame to a non-cognate DBD directly, e.g., without the use of added linker peptides. Linker peptides can be used, but we show herein that they are not needed and they may even be detrimental. Also, preferred, the non-cognate DBD is cut at the same crossover point, or reasonably close by, e.g., within 1-10 aa, preferably 1-3 aa. Some small amount of leeway may be accommodated, providing the 3D structure of the protein is largely retained. Of course, it is understood that the gene fragments must be fused in frame for operability.

As used herein, a "rewired" RR is a "chimeric" or "hybrid" RR to RRs with DBDs swapped for those of another family member.

As used herein, an "input" or input signal" refers to the incoming chemical or environmental condition that activates the SK of a TCS. An "output" on the other hand, refers to those genes, or promoters thereof, being regulated by the RR.

As used herein, "heterologous" means a component from another species.

As used herein, the expressions "bacterium", "bacteria", "microorganism", "microbe", "strain", "species" and the like may be used interchangeably and all such designations include their progeny. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, reference to a "cell" is generally understood to include a culture of such cells, as the work described herein is done in cultures having $10^{9-15}$ cells.

As used herein, "growing" cells used it its art accepted manner, referring to exponential growth of a culture of cells, not the few cells that may not have completed their cell cycle at stationary phase or have not yet died in the death phase or after harvesting.

As used in the claims, "homolog" means an enzyme with at least 40% identity to one of the listed sequences and also having the same general catalytic activity, although of course Km, Kcat and the like can vary. While higher identity (60%, 70%, 80%) and the like may be preferred, it is typical for bacterial sequences to diverge significantly (40, 50, 60%), yet still be identifiable as homologs, while mammalian species tend to diverge less (80-90%).

Reference to proteins herein can be understood to include reference to the gene encoding such protein. Thus, a claimed "permease" protein can include the related gene encoding that permease. However, it is preferred herein to refer to the protein by standard name per ecoliwiki or HUGO since both enzymatic and gene names have varied widely, especially in the prokaryotic arts.

Once an exemplary protein is obtained, many additional examples of proteins with similar activity can be identified by BLAST search. Further, every protein record is linked to a gene record, making it easy to design overexpression vectors. Many of the needed enzymes are already available in vectors, and can often be obtained from cell depositories or from the researchers who cloned them. But, if necessary, new clones can be prepared based on available sequence information using RT-PCR techniques. Thus, it should be easily possible to obtain all of the needed enzymes/genes for overexpression.

Another way of finding suitable enzymes/genes for use in the invention is to consider other enzymes with the same EC number, since these numbers are assigned based on the reactions performed by a given enzyme. An enzyme that thus be obtained, e.g., from AddGene or from the author of the work describing that enzyme, and tested for functionality as described herein. In addition, many sites provide lists of proteins that all catalyze the same reaction.

Understanding the inherent degeneracy of the genetic code allows one of ordinary skill in the art to design multiple nucleotides that encode the same amino acid sequence. NCBI™ provides codon usage databases for optimizing DNA sequences for protein expression in various species. Using such databases, a gene or cDNA may be "optimized" for expression in *E. coli*, yeast, algal or other species using the codon bias for the species in which the gene will be expressed.

Initial cloning experiments have proceeded in *E. coli* for convenience since most of the required genes are already available in plasmids suitable for bacterial expression, but the addition of genes to bacteria is of nearly universal applicability. Indeed, since recombinant methods were invented in the 70's and are now so commonplace, even school children perform genetic engineering experiments using bacteria. Such species include e.g., *Bacillus, Streptomyces, Azotobacter, Trichoderma, Rhizobium, Pseudomonas, Micrococcus, Nitrobacter, Proteus, Lactobacillus, Pediococcus, Lactococcus, Salmonella, Streptococcus, Paracoccus, Methanosarcina,* and *Methylococcus,* or any of the completely sequenced bacterial species. Indeed, hundreds of bacterial genomes have been completely sequenced, and this information greatly simplifies both the generation of vectors encoding the needed genes, as well as the planning of a recombinant engineering protocol. Such species are listed along with links at http://en.wikipedia.org/wiki/List_of_sequenced_bacterial_genomes.

Furthermore, a number of databases include vector information and/or a repository of vectors and can be used to choose vectors suitable for the chosen host species. See e.g., AddGene.org which provides both a repository and a searchable database allowing vectors to be easily located and obtained from colleagues. See also Plasmid Information Database (PlasmID) and DNASU having over 191,000 plasmids. A collection of cloning vectors of *E. coli* is also kept at the National Institute of Genetics as a resource for the biological research community. Furthermore, vectors (including particular ORFS therein) are usually available from colleagues.

The proteins can be added to the genome or via one or more expression vectors (preferably inducible), as desired. Preferably, multiple proteins are expressed in one vector or multiple enzymes can be combined into one operon by adding the needed signals between coding regions. Further improvements can be had by overexpressing one or more, or even all of the proteins, e.g., by adding extra copies to the cell via plasmid or other vector. Initial experiments may employ expression plasmids hosting one or more ORFs for convenience, but it may be preferred to insert operons or individual genes into the genome for long-term stability. It may be especially preferred to integrate a reporter gene construct into the genome, as that cell could then be used as the basis for many different biosensors, merely by switching out the TCS components.

In calculating "% identity" the unaligned terminal portions of the query sequence are not included in the calculation. The identity is calculated over the entire length of the reference sequence, thus short local alignments with a query sequence are not relevant (e.g., % identity=number of aligned residues in the query sequence/length of reference sequence). Alignments are performed using BLAST homology alignment as described by Tatusova T A & Madden T L (1999) FEMS Microbiol. Lett. 174:247-250, and available through the NCBI website. The default parameters were used, except the filters were turned OFF.

"Operably associated," "operably linked", or "operably coupled" as used herein, refer to functionally coupled nucleic acid or amino acid sequences.

"Recombinant" is relating to, derived from, or containing genetically engineered material. In other words, the genetic material of an organism was intentionally manipulated by the hand-of-man in some way.

"Overexpression" or "overexpressed" is defined herein to be at least 150% of protein activity as compared with an appropriate control species, or any detectable expression in a species that lacks the activity altogether. Preferably, the activity is increased 100-500% or even ten fold. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or up-regulating the endogenous gene, and the like. All overexpressed genes or proteins are signified herein by "+".

In certain species, it is possible to genetically engineer an endogenous protein to be overexpressed by changing the regulatory sequences or removing repressors. However, overexpressing the gene by inclusion on selectable plasmids or other vectors that exist in hundreds of copies in the cell may be preferred due to its simplicity and ease of exerting externals controls, although permanent modifications to the genome may be preferred in the long term for stability reasons.

The term "endogenous" means that a gene originated from the species in question, although that gene may be naturally or intentionally mutated, or placed under the control of a promoter that results in overexpression or controlled expression of said gene. Thus, genes from *Clostridia* would not be endogenous to *Escherichia*, but a plasmid expressing a gene from *E. coli* or would be considered to be endogenous to any *E. coli* strain, even though it may now be overexpressed. In contrast, a "wild type" gene or protein means the gene coding regions and have not been substantively changed, nor the activity, and the amino acid sequence corresponds to one found in nature. A "wild type endogenous" gene would thus be the same gene found in that species, without any substantive mutations to the coding regions.

"Expression vectors" are used in accordance with the art-accepted definition of a plasmid, virus or other propagatable sequence designed for protein expression in cells. There are thousands of such vectors commercially available, and typically each has an origin of replication (ori); a multiple cloning site; a selectable marker; ribosome binding sites; a promoter and often enhancers; and the needed termination sequences. Most expression vectors are inducible, although constitutive expression vectors also exist.

As used herein, "inducible" means that gene expression can be controlled by the hand-of-man, by adding e.g., a ligand to induce expression from an inducible promoter. Exemplary inducible promoters include the lac operon, inducible by IPTG, the strong LAC4 promoter inducible with lactate, and the like. Low level of constitutive protein synthesis may occur even in expression vectors with tightly controlled promoters.

As used herein, an "integrated sequence" means the sequence has been integrated into the host genome, as opposed to being maintained on an expression vector. It will still be expressible, and preferably is inducible as well.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention, such as instructions for use, buffers, background mutations that do not effect the invention, and the like.

The following abbreviations are used herein:

| ABBREVIATION | TERM |
| --- | --- |
| aa | Amino acid |
| ACCN | Accession number |
| aTc | Anhydrotetracyline |
| BAD_0568 | RR from *Bifidobacterium adolescentis* (see Kegg entry for BAD_0568). |
| BAD_0569 | SK from *B. adolescentis*. Phosphorylates BAD-0568. |
| BceR | RR from *B. subtilis*, ACCN: WP_004399109 |
| CcaR | RR from *Synechocystis* PCC6803, ACCN: WP_010874216. |
| CcaS | Green light activated, red light repressed SK from *Synechocystis* PCC 6803 engineered to work in *E. coli*. Phosphorylates CcaR. |
| CopR | RR from *Synechocystis* PCC 6803, ACCN: WP_010873936 SEQ ID NO: 3 |
| Cph8 | Engineered red/far red light switchable SK in *E. coli*. Phosphorylates OmpR. |
| DBD | DNA binding domain |
| FusR | RR from *E. coli*, ACCN: AAG54714 SEQ ID NO: 29, the cognate SK is fusK |
| GFP | Green fluorescent protein |
| KD | Kinase domain |
| LBD | Ligand binding domain |
| LiaR | RR from *B. subtilis*, ACCN: WP_003243201 SEQ ID NO: 28 |
| ManR | RR from *Synechocystis* PCC6803, ACCN: WP_010872074 |
| mCherry | mCherry fluorescent protein |
| NarL | RR from *Escherichia coli*. ACCN: NP_415739 |
| NarX | Nitrate sensing SK from *Escherichia coli*. Phosphorylates NarL. |
| OmpR | RR from *E. coli*. ACCN: NP_417864 |
| PydfJ | *B. subtilis* Promoter activated by the phosphorylated form of the response regulator YdfI. |
| PdcuS | Phosphorylated NarL binds to the repressible PdcuS promoter from *E. coli*, regulating the expression of sfGFP. Low nitrate conditions result in high sfGFP expression, high nitrate conditions repress transcription. The sensitivity of the sensor is in the sub-mM to mM range for nitrate. |
| PcpcG2 | Inverted Green light inducible pCpcG2 promoter, from pJT122 plasmid constructed by Tabor et al. (2010). It is positively regulated by the two component system CcaS/R, which exhibits a maximum response in 535 nm and is inactivated in 650 nm light. Light intensities must be carefully regulated to achieve successful gene expression. The sequence was inverted to ease DNA synthesis. |
| PsdR | RR from *B. subtilis*, ACCN: WP_003244535 |
| REC | Receiver domain |
| RR | Response regulator |
| SK | Sensor kinase or sensor histidine kinase |
| TCS | Two component sensor system including a SK and an RR |
| UhpA | RR from *E. coli*, ACCN: NP_418125 |
| UhpB | *E. coli* SK that interacts with UhpC, a periplasmic protein that binds Glucose-6-phosphate. UhpB phosphorylates UhpA. |
| UhpC | *E. coli* periplasmic protein that binds Glucose-6-phosphate and then stimulates the SK UhpB. |
| YdfI | RR from *B. subtilis*, ACCN: WP_003244318 |
| YxdJ | RR from *B. subtilis*, ACCN: WP_003243527 |

BRIEF DESCRIPTION OF FIGURES

FIG. 6. Validation of pathway activity. Mutation of BAD_0569 catalytic histidine (H298) to non-catalytic asparagine (N) residue (i.e. H298N) as shown here, greatly reduced if not eliminated reporter gene expression (see FIG. 7).

FIG. 9. Amino acid sequences for the native RRs and hybrid RRs tested herein.

FIG. 10. Identification of crossover points permitting the rewiring of OmpR-CcaR to make chimeric or hybrid RRs. The 705 nm light activated, 650 nm light de-activated sensor histidine kinase (SK) Cph8 phosphorylates our novel OmpR-CcaR hybrids. The phosphorylated OmpR-CcaR hybrids activate transcription from the CcaR activated PcpcG2-172 promoter in *E. coli*. PcpcG2-172 activity is measured using sfGFP reporter gene and flow cytometry.

FIG. 11. OmpR-ManR rewire. Dark and 705 nm light both stimulate the SK Cph8—the latter shown in FIG. 10. Thus, dark results in phosphorylation of OmpR-ManR, causing repression of the ManR output promoter in *E. coli*.

FIG. 28. A partial listing of embodiments of the invention, any one of which can be combined with any one or more embodiments, or portions thereof.

DETAILED DESCRIPTION

Figure 1:
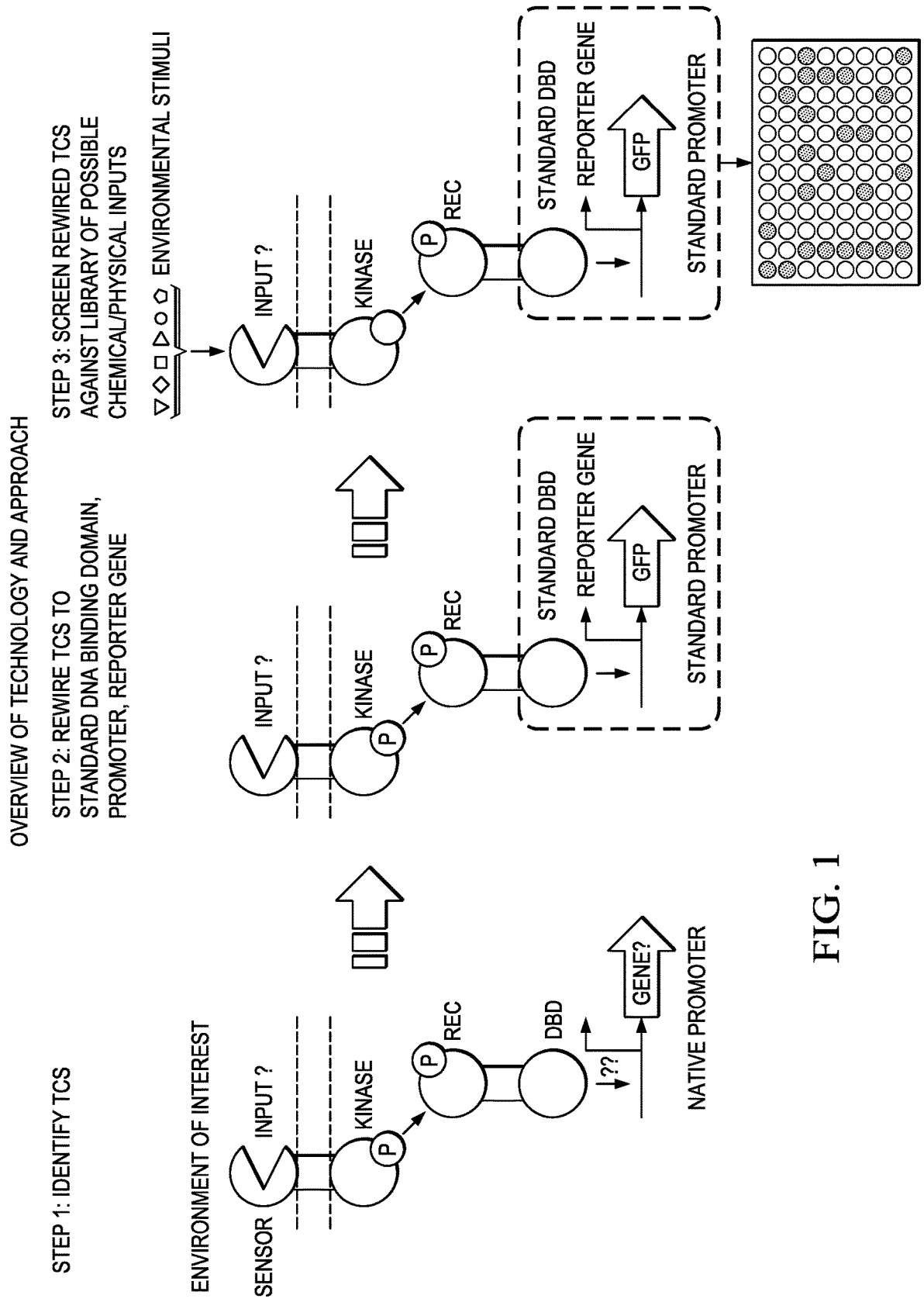
FIG. 1. Overview of new technology and approach.

The steps of the method include one or more of the following, although control experiments may be varied and certain steps can be omitted, depending on the state of research:

1) Identify a TCS (SK and RR) of interest from published literature or computational search of DNA or preferably amino acid sequence. The SK and its cognate RR are typically within 200-1000 base pairs of one another on the genome, encoded on the same or opposite strands, making the pairing of the cognate SK and RR fairly simple to determine based on homology search and domain identification.

2) Swap the naturally occurring DBD of the RR with that of a well-characterized non-cognate DBD of an RR with a known output promoter, such as CcaR (or a list of numerous others that we have developed herein or can be identified from the literature).

3) Express the SK and the modified RR in a model laboratory bacterium such as *E. coli* or *Bacillus subtilis*, and the like. Constitutive or inducible promoters may be used, but inducible promoters enable rapid identification of SK and RR expression levels resulting in proper input-dependent TCS response. Improper SK or RR expression levels can reduce or eliminate input dependent TCS response.

The functionality of the chimeric RR alone can be validated by inducing its expression over a wide range and measuring the response of the output promoter that the chimeric RR is intended to regulate with a GFP reporter gene. In a typical case, the chimeric RR may activate the desired output promoter. Thus induction of the RR over a wide range will result in activation of the new promoter. Activation without the input (or even SK) present can result from alternative sources of phosphorylation of the RR in the cell (e.g. from acetyl-phosphate or non-cognate SKs) or low-affinity binding of the promoter, which nonetheless becomes significant at high levels of RR expression. By mutating the conserved RR aspartate to a non-phosphorylatable residue, the chimera can be further validated (this mutant should not activate the desired output promoter as strongly, or at all).

4) Co-express a reporter gene, such as a fluorescent protein, a chromogenic enzyme (beta-galactosidase) or an mRNA that can be quantified under the known output promoter of the replacement DBD. The three components (SK, modified RR and reporter gene) can be provided on the same expression vector, or multiple expression vectors. The reporter gene can also be integrated into the genome, such that the same cell line can be used for a number of different SK/RR pairs. The SK and RR can also be integrated, but do not have to be.

6) Screen the cells expressing the SK and modified RR against any input signals that may activate the SK by growing the bacteria at different concentrations of the candidate input signals.

7) Identify those input signals that trigger a change in the reporter gene expression.

Preferably, these experiments are followed up by validation experiments, to confirm proper signaling. Alternatively, these experiments can be performed simultaneously, but fewer sample runs are needed with sequential experiments since only those positive inputs are then tested by these control experiments.

8) Validate those input signals by mutating the conserved histidine on the SK or phosphorylated aspartate on the RR and repeating the treatment with the input. These mutations should reduce if not eliminate the signal.

9) Demonstrate that the input does not activate the RR or output promoter or reporter gene non-specifically by expressing a second reporter gene (e.g. mCherry) from a constitutively active promoter (not regulated) in the same bacterium. A true input will result in a change in the ratio of the pathway-specific reporter to the constitutive reporter, but not when the histidine or aspartate is mutated.

If a TCS cannot be expressed (e.g. does not fold) in a standard laboratory bacterium, this can be overcome by a number of standard means for increasing solubility (lower temperature, fusion to maltose binding protein, chaperone overexpression). Other model organisms, including other bacteria and yeasts, could also be used to expand work around possible failures.

If a TCS is not completely self contained (e.g. requires an additional gene, protein, or cofactor in the native organism that is not present in the model organism), this could be overcome by expressing the additional gene (if known) or libraries of genes from the genome of the native organism alongside the DBD-replaced TCS in the laboratory organism, or using other model organisms. Alternatively, the additional gene may be simple to identify because it resides adjacent to the TCS on the genome and is homologous to known additional genes that are required for signaling (e.g. UhpC resides next to UhpB and UhpA on the *E. coli* genome and UhpC is a transporter like protein shown to bind Glucose-6-phosphate for UhpB mediated signaling to UhpA and UhpC homologs are found next to other TCSs as well).

We have demonstrated proof of concept for the method using a novel OmpR-PhoB family TCS, BAD_0569-BAD_0568 (aka BAD_0569/8), which is taken from the species *Bifidobacterium adolescentis*. Homologs of BAD_0569/8 have also been discovered to be enriched in the colonic bacteria of obese humans, and thus this particular TCS is of general interest in obesity research.

Figure 2:
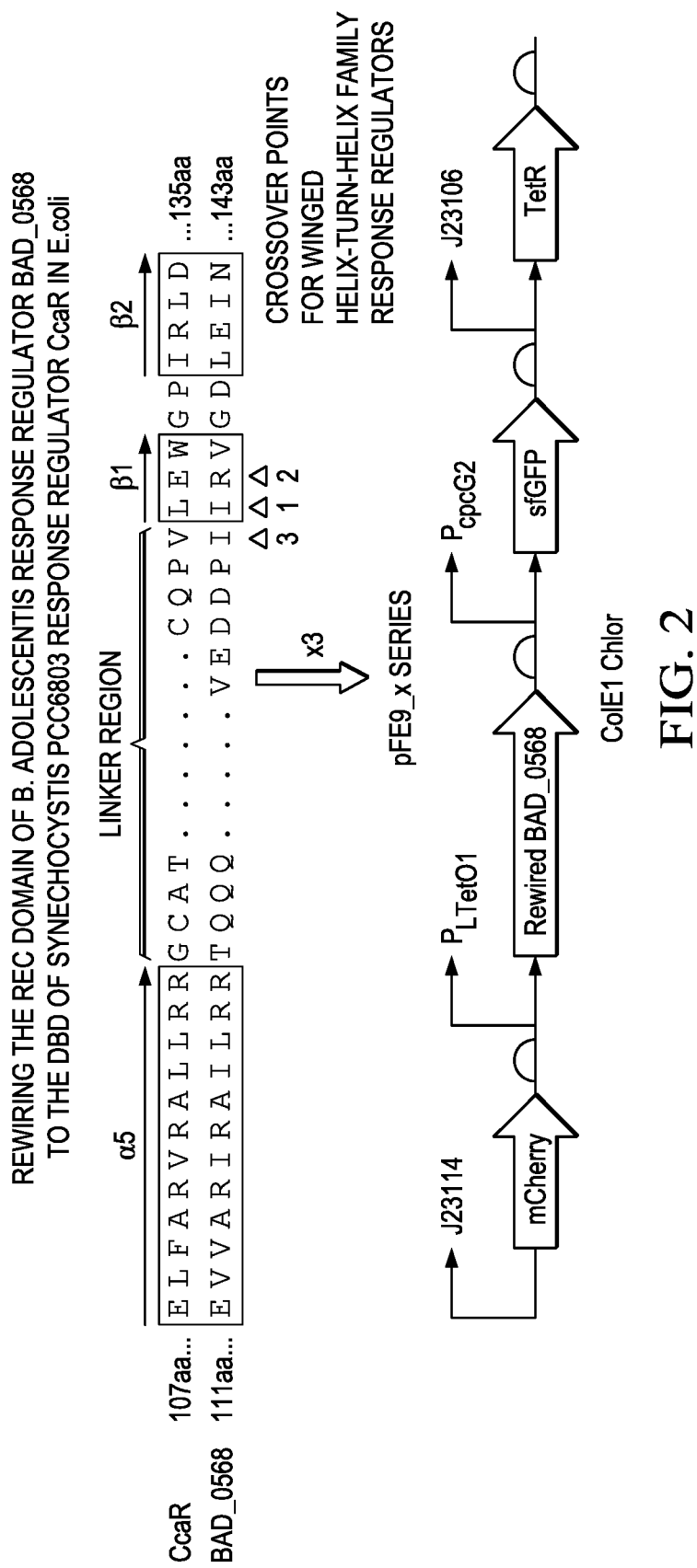
FIG. 2. Rewiring the REC domain of the *B. adolescentis* response regulator BAD_0568 to the known output DBD of *Synechocystis* PCC6803 response regulator CcaR in *E. coli*.

The general experimental outline for this proof of concept experiment is shown in FIG. 2. Briefly, the wild type BAD_0569 SK of *Bifidobacterium adolescent* was expressed in *E. coli*. A modified cognate response regulator BAD_0568 was simultaneously expressed in *E. coli*, wherein the native DBD from the *Bifidobacterium adolescentis* RR was replaced with that of the DBD from the well-characterized OmpR-PhoB family RR CcaR. When phosphorylated, native CcaR activates transcription from PcpcG2, or its derivatives. A superfolder GFP reporter gene (a.k.a. GFP) was expressed from PcpcG2 in the same *E. coli*. Anydrotetracyline (aTc) induces expression of the BAD_0568-CcaR hybrid, which activates PcpcG2 transcription and thus GFP expression.

Generally speaking herein, SK was expressed from a ColE1 plasmid, the RR was expressed from a p15A plasmid, and the output promoter and reporter were expressed from a p15A or a pSC101 plasmid. However, this is a matter of convenience only, and two or all three components could be co-expressed from a single plasmid, and/or one or more components can be integrated.

Figure 3:
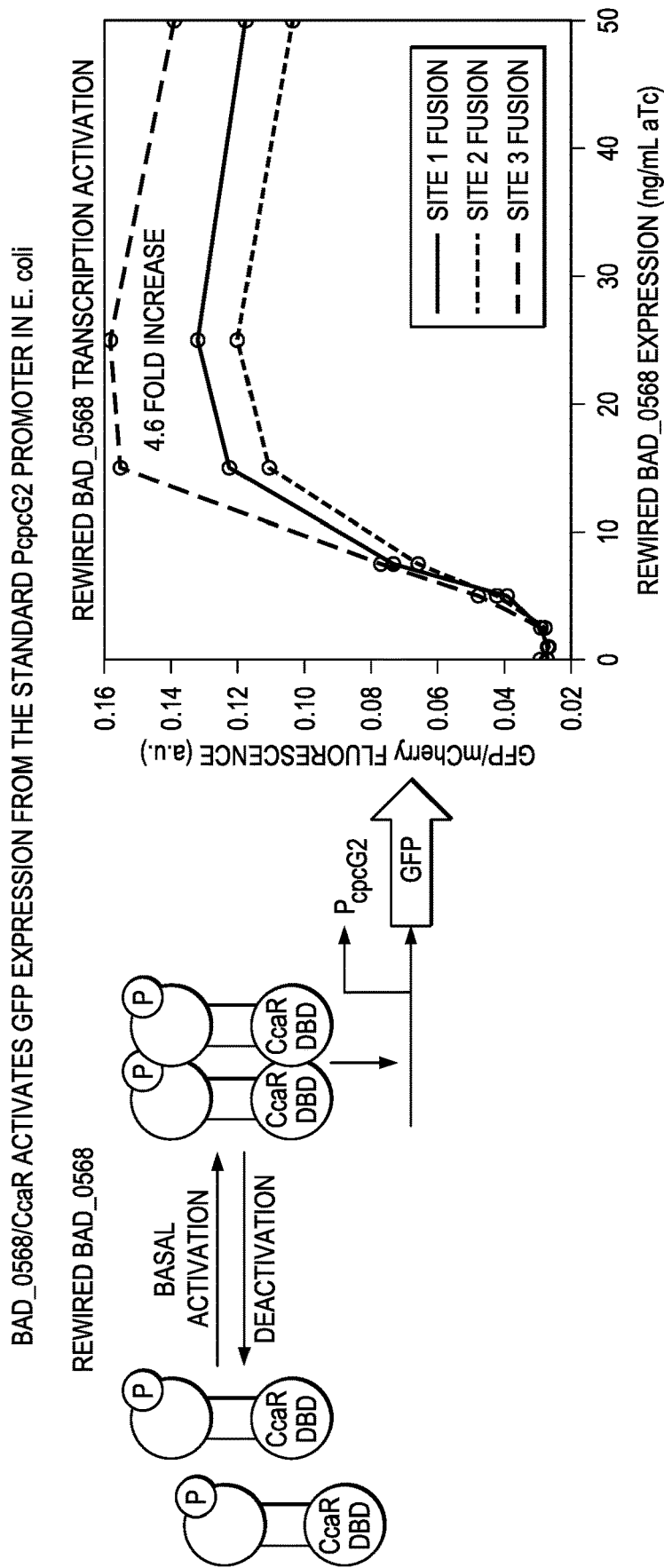
FIG. 3. BAD_0568-CcaR activates GFP expression from the standard PcpcG2 promoter in *E. coli*. BAD 0568 is an RR from *Bifidobacterium adolescentis* (see Kegg entry for BAD_0568). CcaR is an RR from *Synechocytis* PCC 6803 that we have transported to *E. coli*. It induces transcription from PcpcG2 in *Synechocystis* PCC6803 and *E. coli*. Anhydrotetracyline is used to induce BAD_0568/CcaR expression. Superfolder GFP is being expressed from the PcpcG2-172 promoter (a variant of PcpcG2) in *E. coli*. The cognate BAD_0569 SK is absent, but BAD 0568/CcaR is being phosphorylated from another source, such as acetyl phosphate or a non-cognate SK. A plasmid vector with the ColE1 origin of replication and chloramphenicol resistance maker is used to carry the SK, RR constructs, and the reporter gene construct was described in Tabor (2010) and Tabor (2011).
Figure 4:
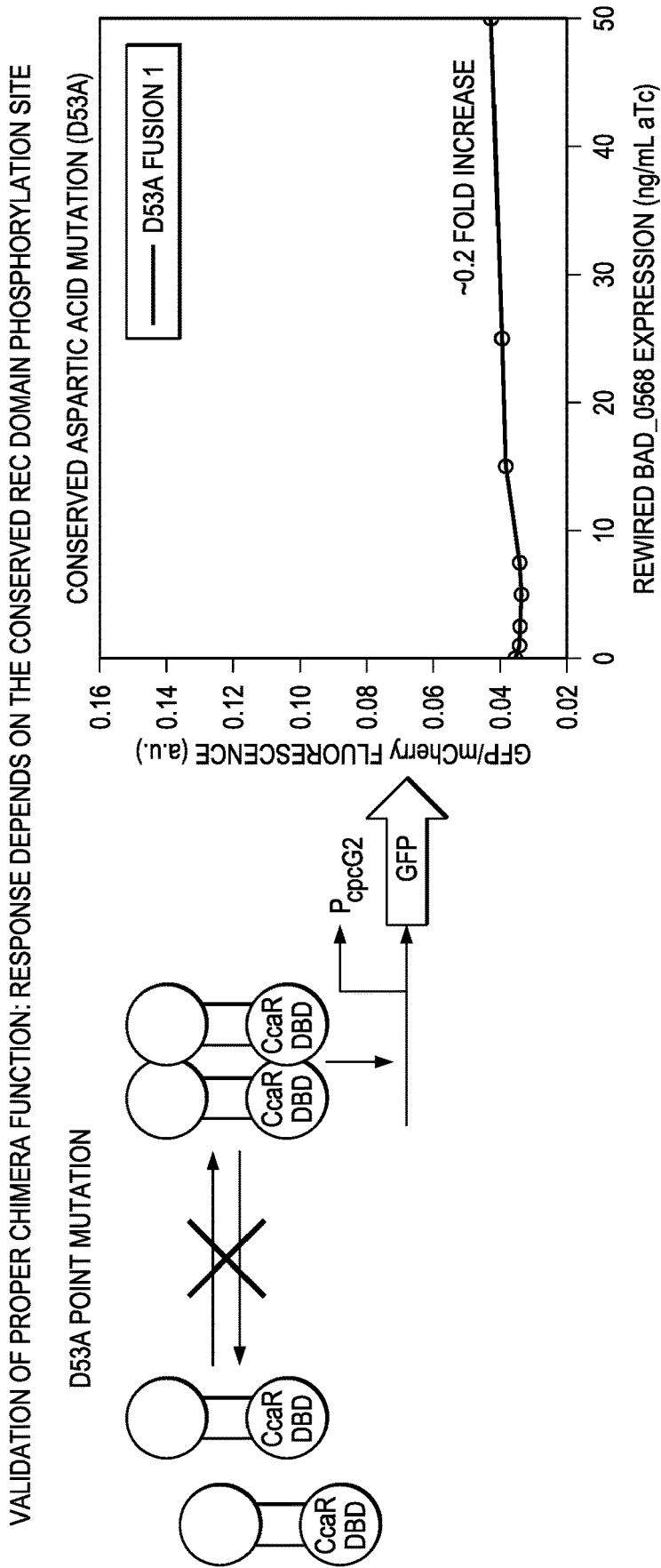
FIG. 4. Validation of proper BAD_0568-CcaR chimera function: activation of PcpcG2-172 depends on the conserved REC domain phosphorylation site.
Figure 5:
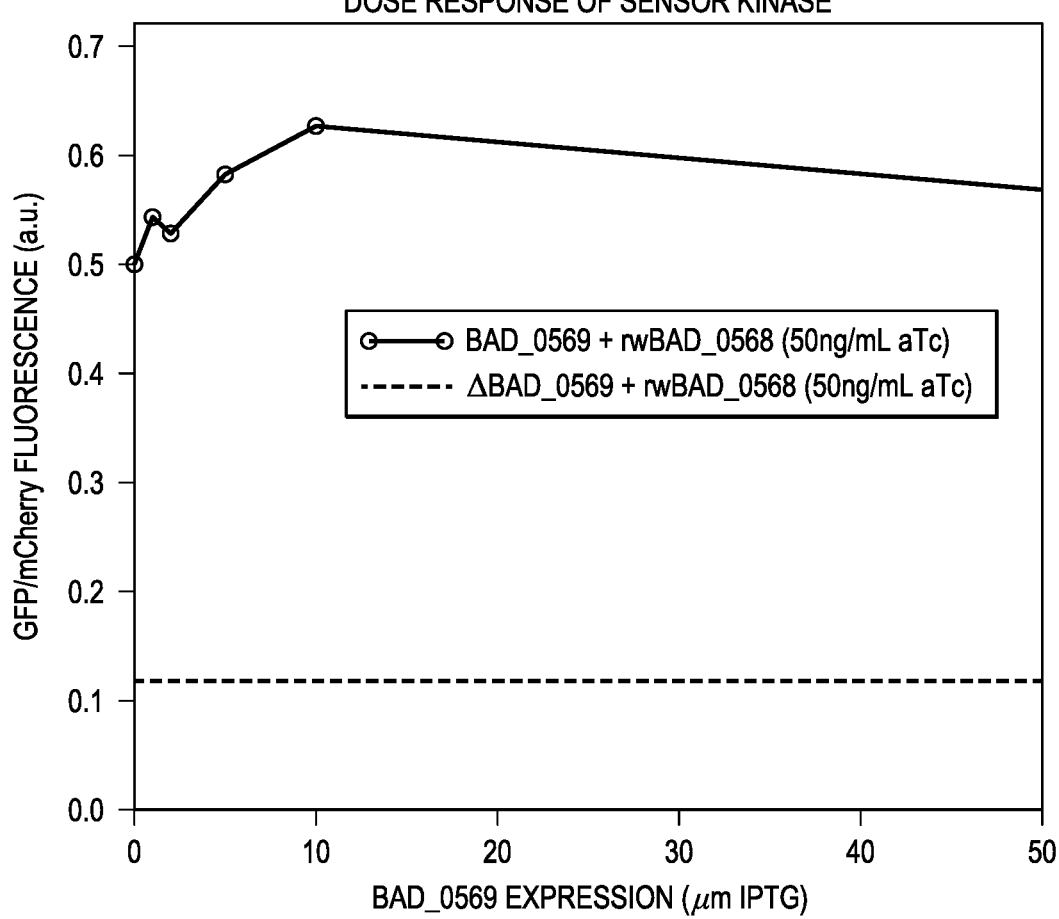
FIG. 5. Validation of chimeric pathway activity. Expression of the sensor kinase BAD_0569 activates transcription from PcpcG2-172 in the presence of BAD_0568/CcaR chimera.

FIG. 3 shows the functionality of the system. Three different BAD_0568-CcaR chimeras were made and induced with aTc as in FIG. 2. GFP expression increases with induction of the BAD_0568-CcaR chimeras, likely due to spontaneous phosphorylation of the chimera by acetyl phosphate or non-cognate SKs in *E. coli* (BAD_0569 is absent). This experiment shows that the chimera can activate the non-native PcpcG2 output promoter. Functionality of the chimera was also validated in several ways. For example, in FIG. 4, we show that response completely depends on the conserved REC domain phosphorylation site. FIG. 5. shows that co-expression of the BAD_0569 SK (induced by IPTG in this case), which phosphorylates the BAD_0568 REC domain to some extent even in the absence of its input increases PcpcG2 activity. In FIG. 6, we show that mutation of catalytic histidine to non-catalytic asparagine (N) residue eliminates the activating effect of BAD_0569, validating that the effect is due to phosphotransfer (see FIG. 7 for exemplary data).

Figure 7A:
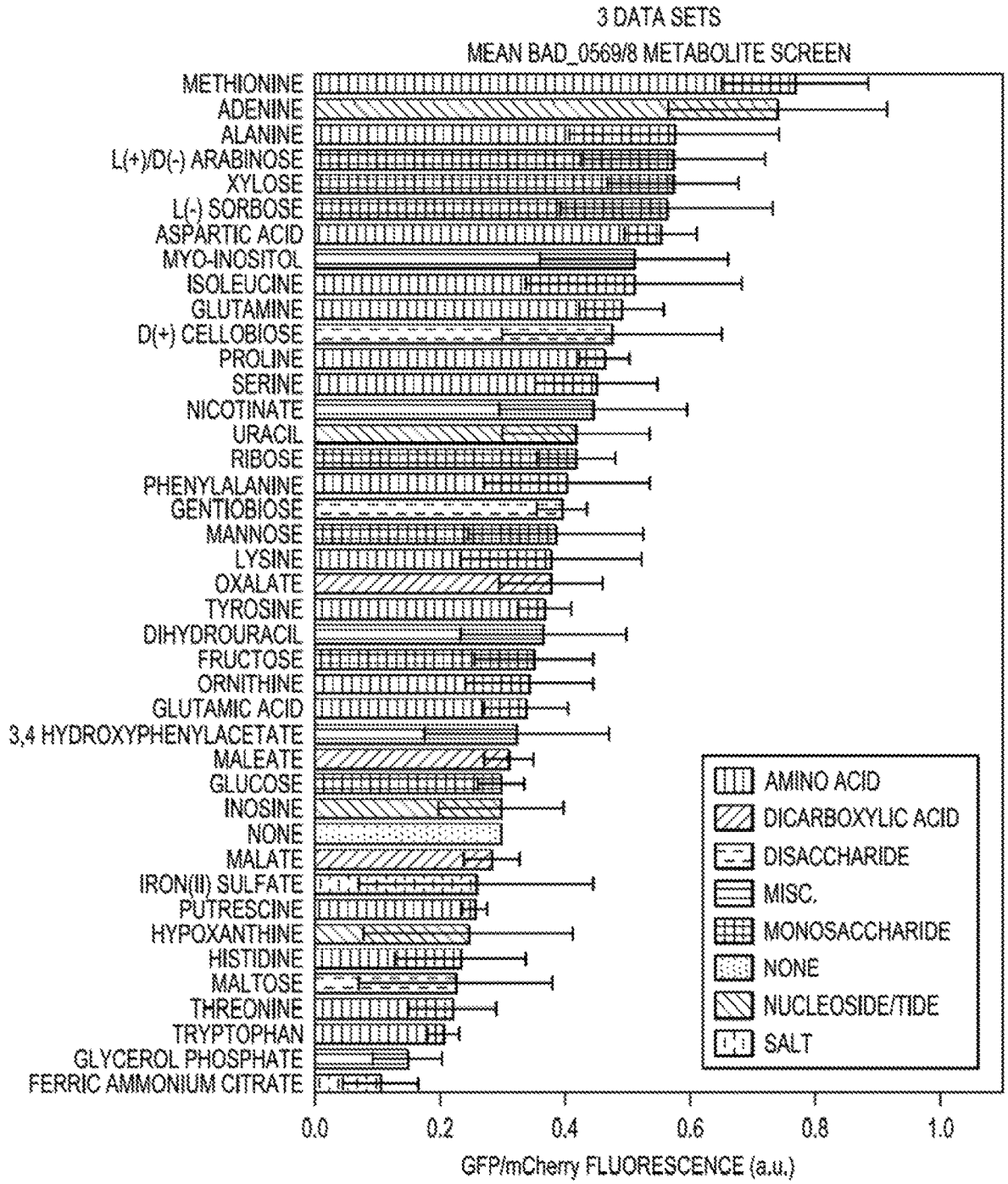
FIG. 7. High throughput screen of rewired BAD_0569/BAD_0568 (a.k.a. BAD_0569/8)-CcaR pathway to panel of mammalian gut metabolites in *E. coli* with negative control H298N showing no response and positive control of TAZ/OmpR-CcaR system (wherein the SK TAZ senses only aspartate and phosphorylates OmpR-CcaR which activates transcription from PcpcG2-172) responding only to aspartate.
Figure 7B:
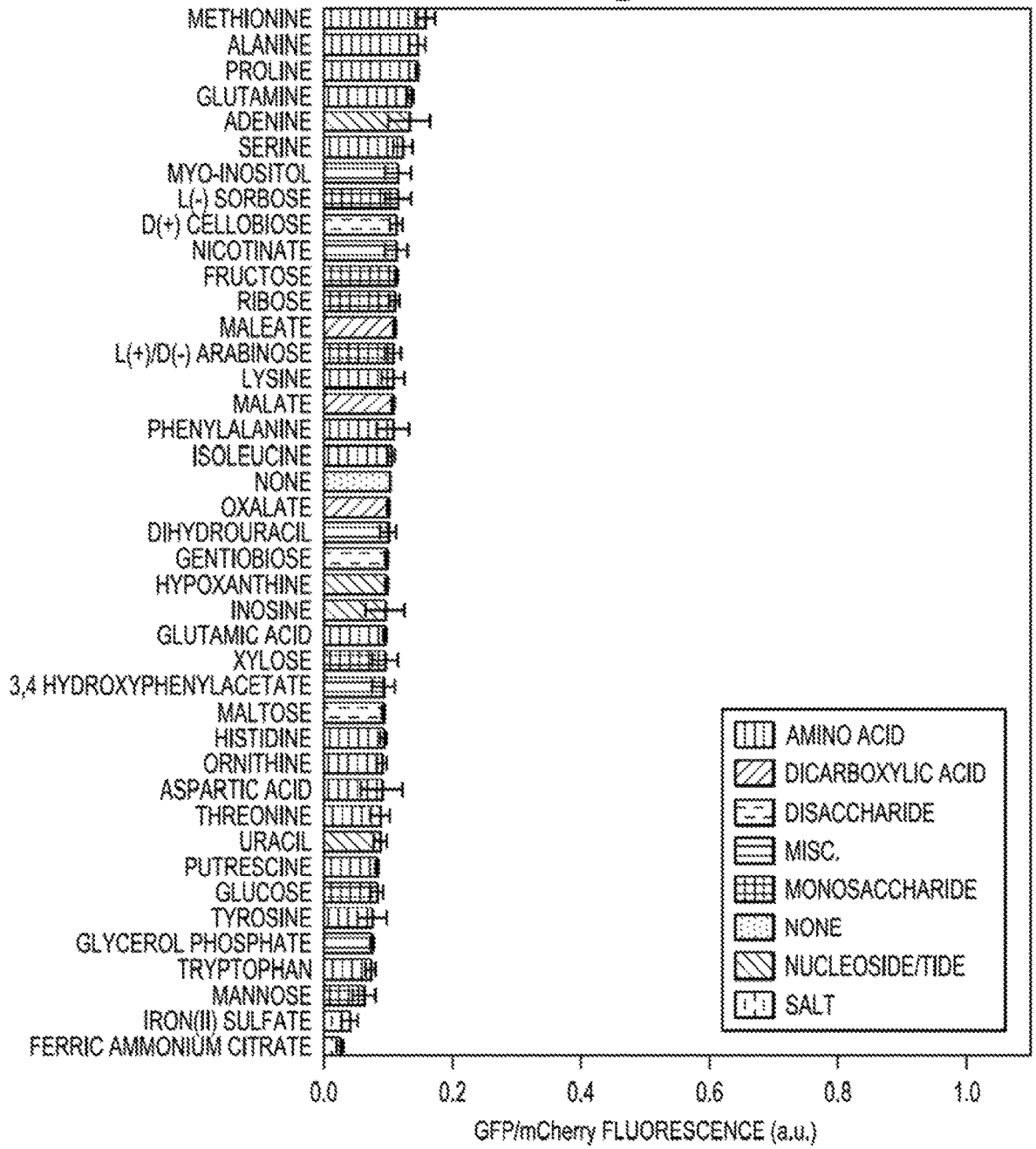
Figure 7C:
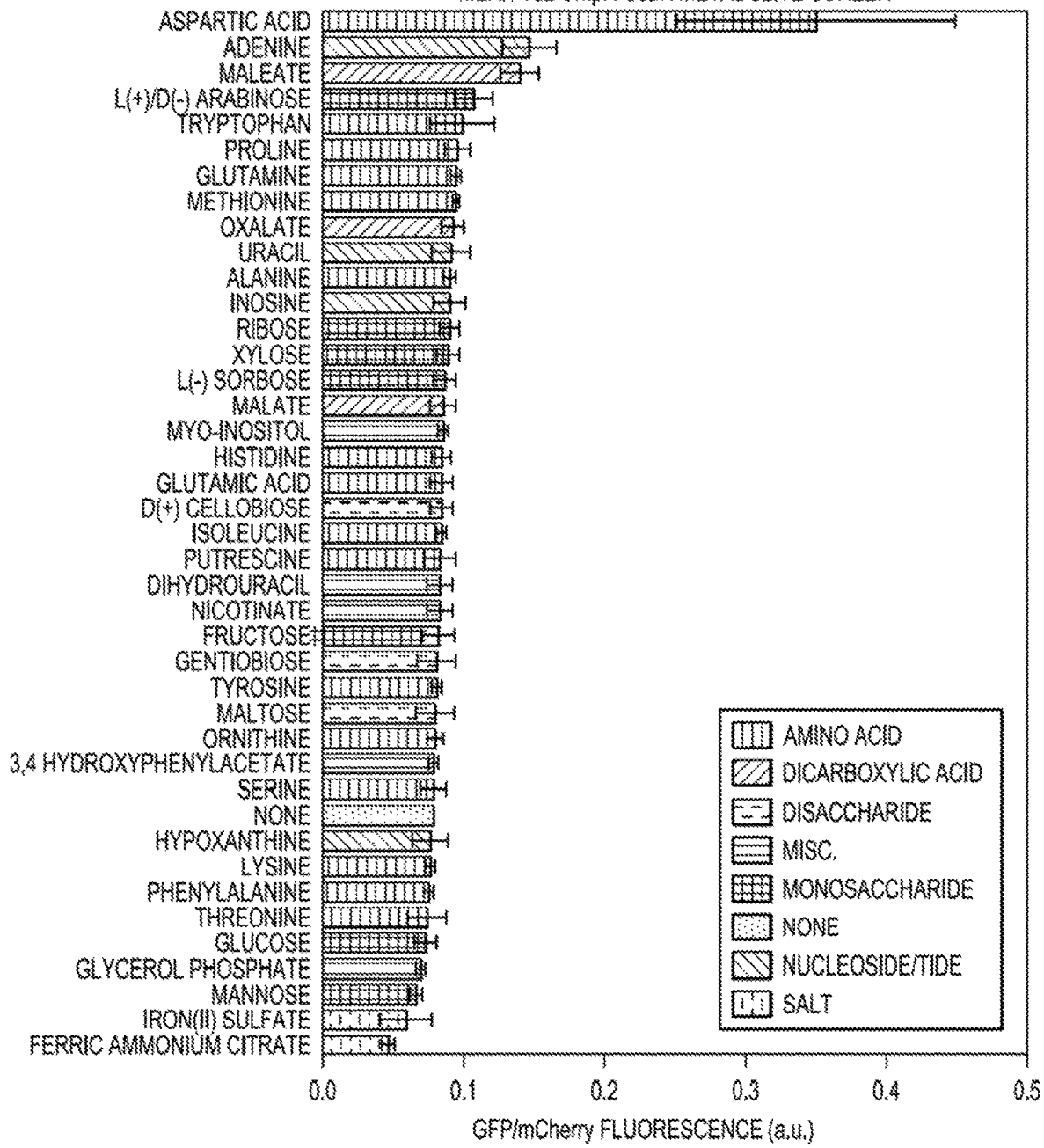
Figure 8:
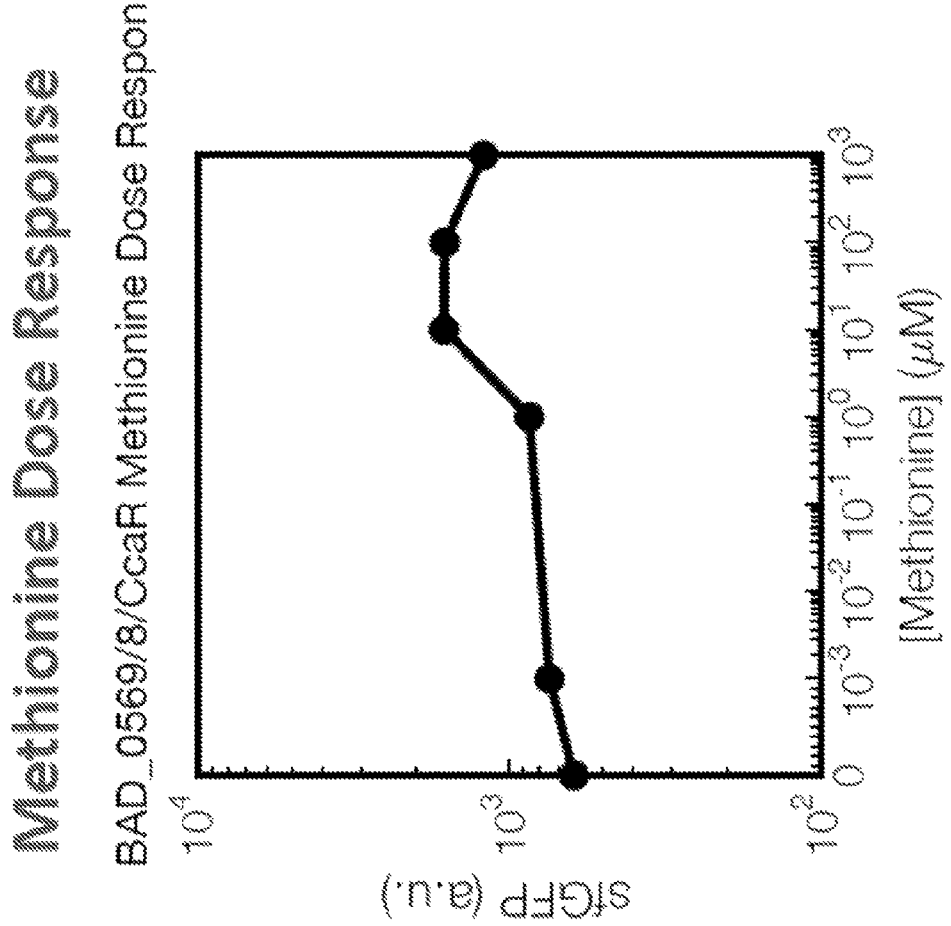
FIG. 8. Methionine Dose Response of rewired BAD_0569/BAD_0568-CcaR TCS with sfGFP output from PcpcG2-172 in *E. coli*.
Figures 12, 13:
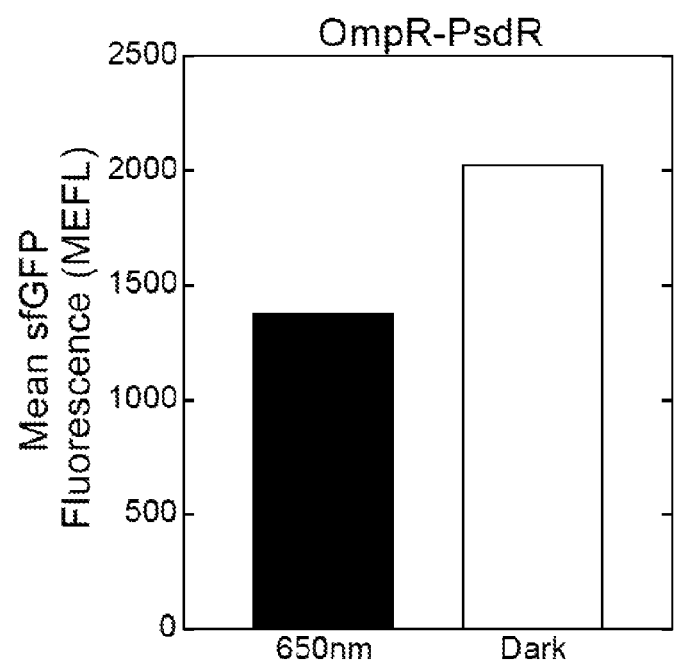
FIG. 12. OmpR-PsdR rewire. Data collected in *E. coli* expressing Cph8. PsdR activates its output promoter, thus dark results in increased transcription and 650 nm results in decreased transcription in this chimera.
FIG. 13. OmpR-YxdJ. Data collected in *E. coli* expressing Cph8. YxdJ activates its output promoter.
Figure 14:
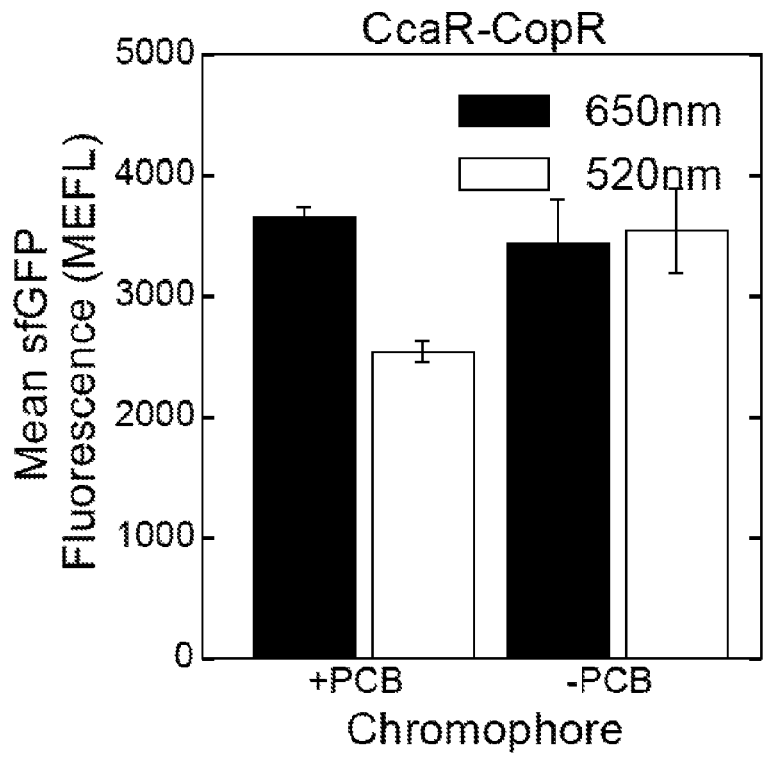
FIG. 14. CcaR-CopR rewire. The SK CcaS is activated by green light (520 nm) and repressed by red (650 nm) in the presence of the chromophore phycocyanobilin (PCB), but not in its absence. These data were collected in *E. coli* expressing CcaS with and without PCB. CcaS phosphorylates CcaR-CopR, causing repression of its output promoter. This effect is absent without chromophore.
Figure 15:
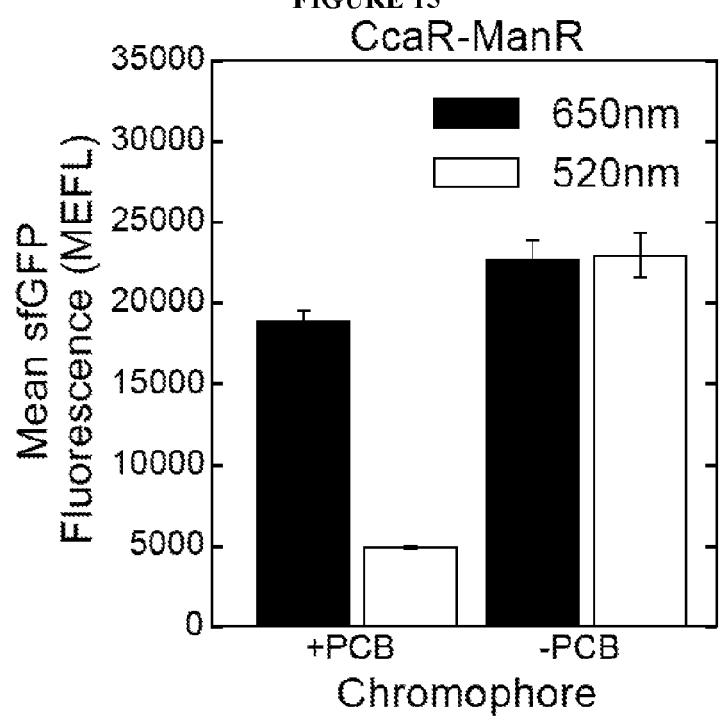
FIG. 15. CcaR-ManR rewire. Experiments are as described in FIG. 14, unless stated otherwise.
Figure 16:
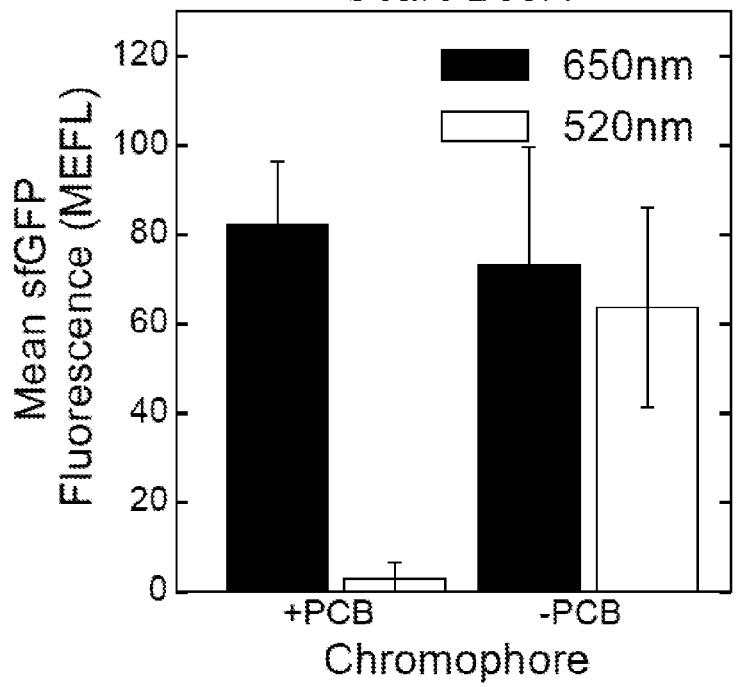
FIG. 16. CcaR-BceR rewire.
Figure 17:
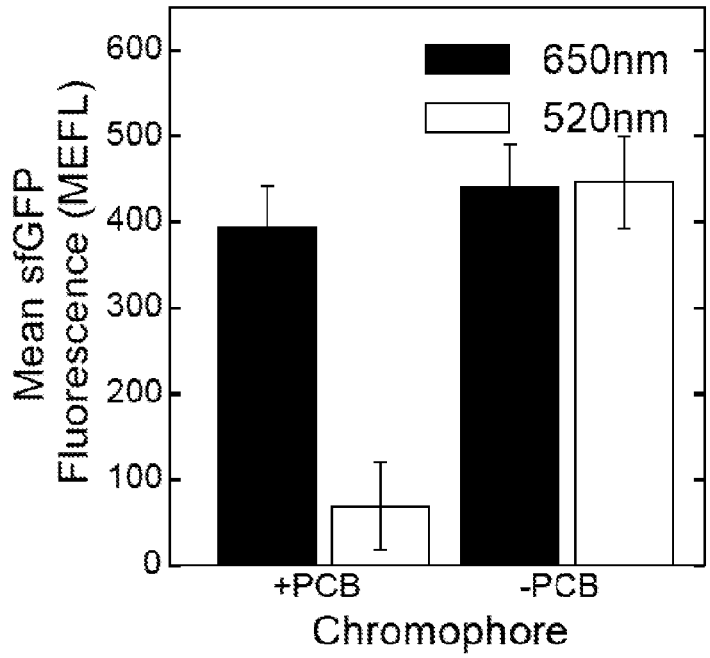
FIG. 17. CcaR-PsdR rewire.
Figure 18:
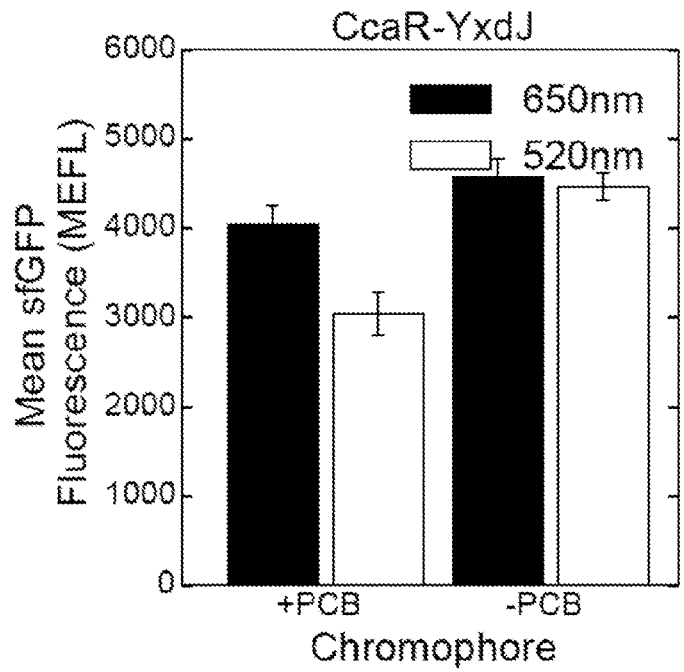
FIG. 18. CcaR-YxdJ rewire.
Figure 19:
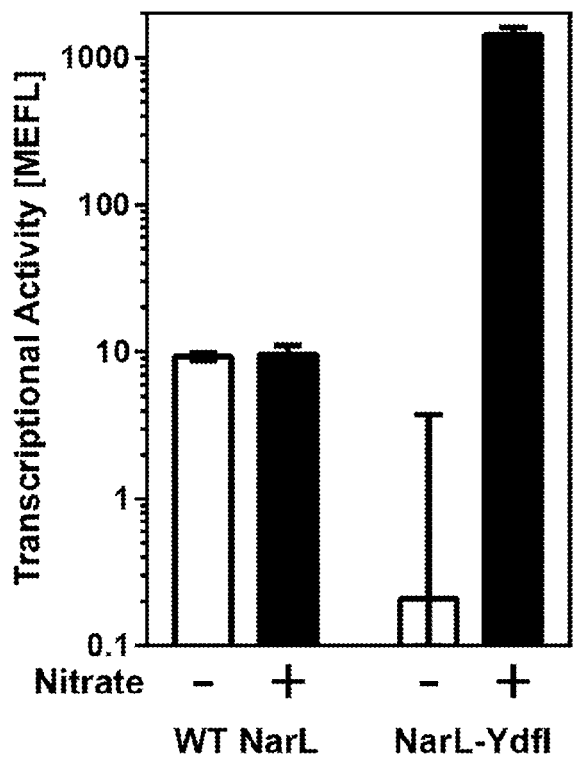
FIG. 19. NarL-YdfI rewire. The wild-type TCS NarX-NarL with PdcuS promoter output was transported from *E. coli* to *B. subtilis*. The bacteria were treated with and without the NarX inducer nitrate. No response is seen (Left). When NarL DBD is replaced with YdfI and the PydfJ output promoter, which is activated by the YdfI DBD, the nitrate response is recovered. This data shows that DBD rewiring allows transport of TCSs between organisms with otherwise incompatible transcriptional regulation systems.
Figure 20:
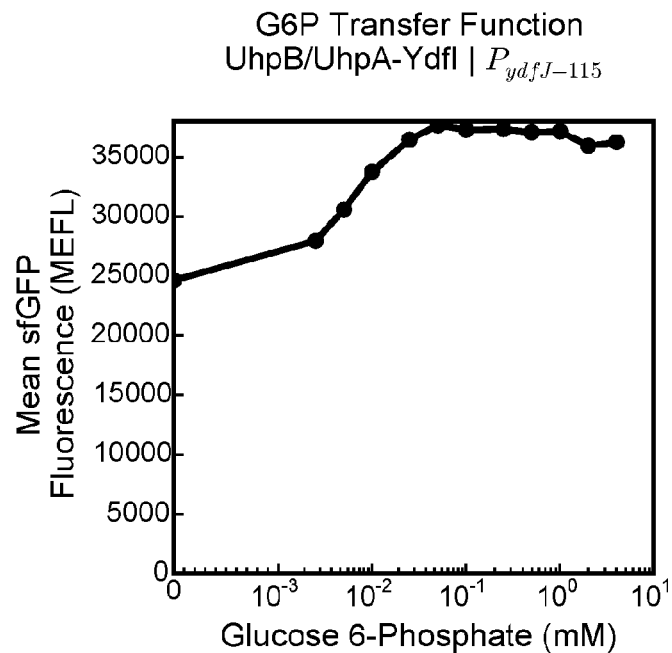
FIG. 20. UhpA-YdfI chimera in *E. coli*. The SK UhpB is activated by Glucose-6-phosphate. UhpB phosphorylates UhpA-YdfI, which activates the PydfJ output promoter. The dose response curve to the inducer is shown.
Figure 21:
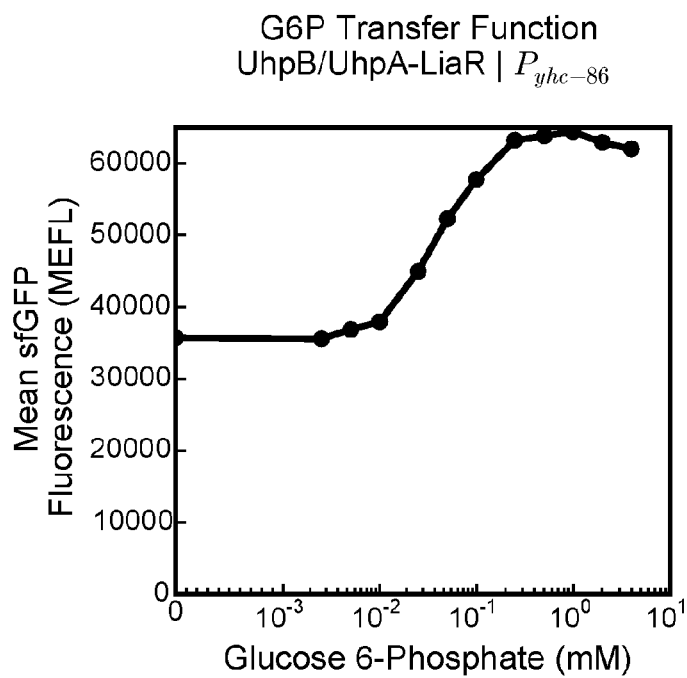
FIG. 21. UhpA-LiaR rewire. The experiment is as described in FIG. 20 unless stated otherwise.

We then tested *E. coli* expressing the hybrid BAD_0569/8 TCS (i.e. BAD_0569 and BAD_0568-CcaR with sfGFP expressed from PcpcG2) in the presence of over 40 chemicals previously found to be enriched in the large intestines of germ-free mice made to carry gut bacteria of obese humans, but not found to be enriched in those mice carrying the gut bacteria of their lean twins. From this list, we have found several possible candidate molecules that are sensed by BAD_0569/8. FIG. 7.

Although we engineered our system in order to identify the inputs for BAD-0569, once the input was identified, our bacteria could then be used as a biosensor for that input. The molecule yielding the largest response was methionine, an amino acid, which may be a biomarker of an unbalanced gut microbiome that can potentially cause obesity (based on published mouse studies and human observations), or at least be a marker for same. Thus, we have used DBD rewiring to engineer a bacterial sensor of pre-obesity or obesity conditions in the human gut.

Of note, B. adolescentis is a gram-positive bacterium (lacks an outer membrane), while E. coli is a gram negative bacterium (has an outer and inner membrane, and the sensor domain of the SK is in the middle periplasmic region). Thus, we demonstrate herein that the TCS can be moved between these two types of bacteria via DBD rewiring. In particular, the output promoter of wild-type BAD_0568 is not known, which precludes movement of a functional pathway into a new organism. Thus, DBD rewiring overcame this limitation, enabling facile movement into E. coli.

We next showed that the proof of concept could be applied more generally to other TCSs—or at least those of the OmpR-PhoB and NarL-FixJ families. FIG. 10 shows some 15 rewired sequences that we have tested using the methods described herein.

We have identified multiple amino acid positions wherein the DBDs of RRs with OmpR-PhoB (a.k.a. winged Helix-turn-Helix; wHTH) and NarL-FixJ (a.k.a. Helix-turn-Helix; HTH) family DBDs can be rewired. Specifically, we have used a set of 7 wHTH RRs from E. coli, Synechocystis PCC 6803, and B. subtilis, and 5 HTH RRs from E. coli and B. subtilis. We have created 15 wHTH rewires (i.e. the DBD of a wHTH RR is replaced with that of a different wHTH RR) from this set and demonstrated their functionality using input (visible light or chemical ligand)-induced transcriptional activation and a superfolder GFP (sfGFP) reporter gene and flow cytometry in E. coli (see FIG. 11-22).

We have created 4 successful HTH family rewires and similarly demonstrated their functionality using chemical ligand induced transcriptional activation and sfGFP and flow cytometry in E. coli and B. subtilis. In particular, we have moved the nitrate activated TCS NarX-NarL from E. coli into B. subtilis by replacing the E. coli-derived NarL DBD with that of the B. subtilis derived YdfI DBD.

Figure 22:
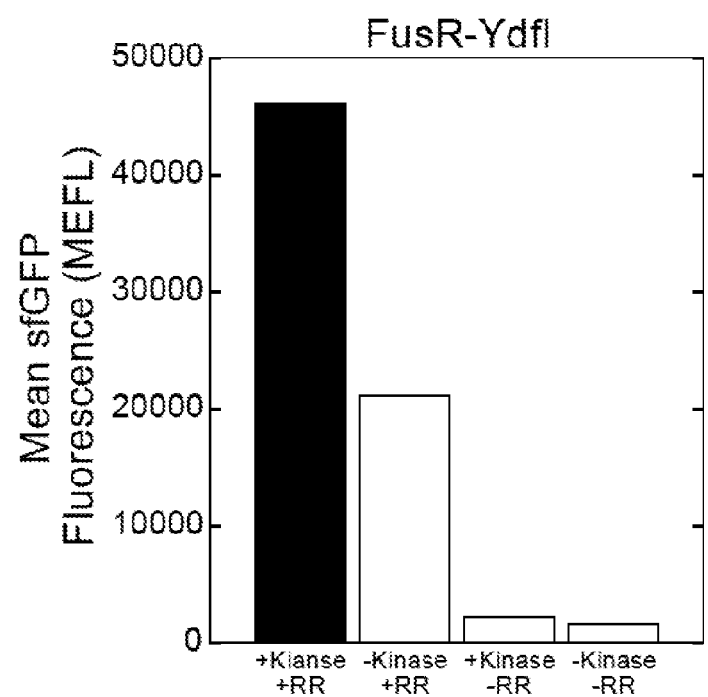
FIG. 22. FusR-YdfI rewire. In the presence of the SK (kinase) FusK, FusR-YdfI (RR) is activated, activating the PydfJ output promoter. In the absence of FusK, the RR is less activated. In the absence of RR, the output promoter is not activated. Experiments done in *E. coli*.
Figure 23A:
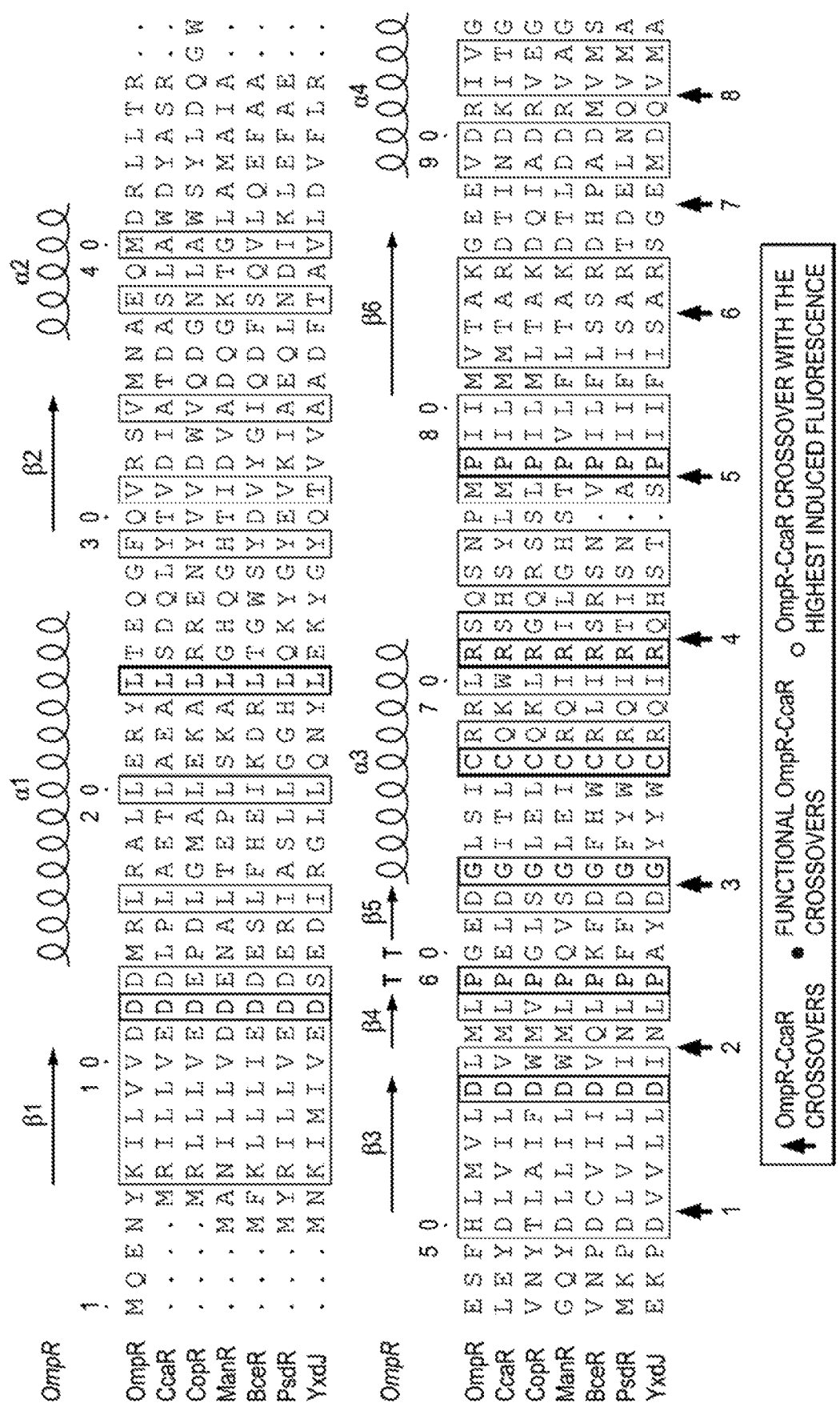
FIG. 23. Alignment of amino acid sequences, numbered according to the numbering of the OmpR RR, and showing all the various sites tested for successful cleavage of the REC domain from the DBD.
Figure 23B:
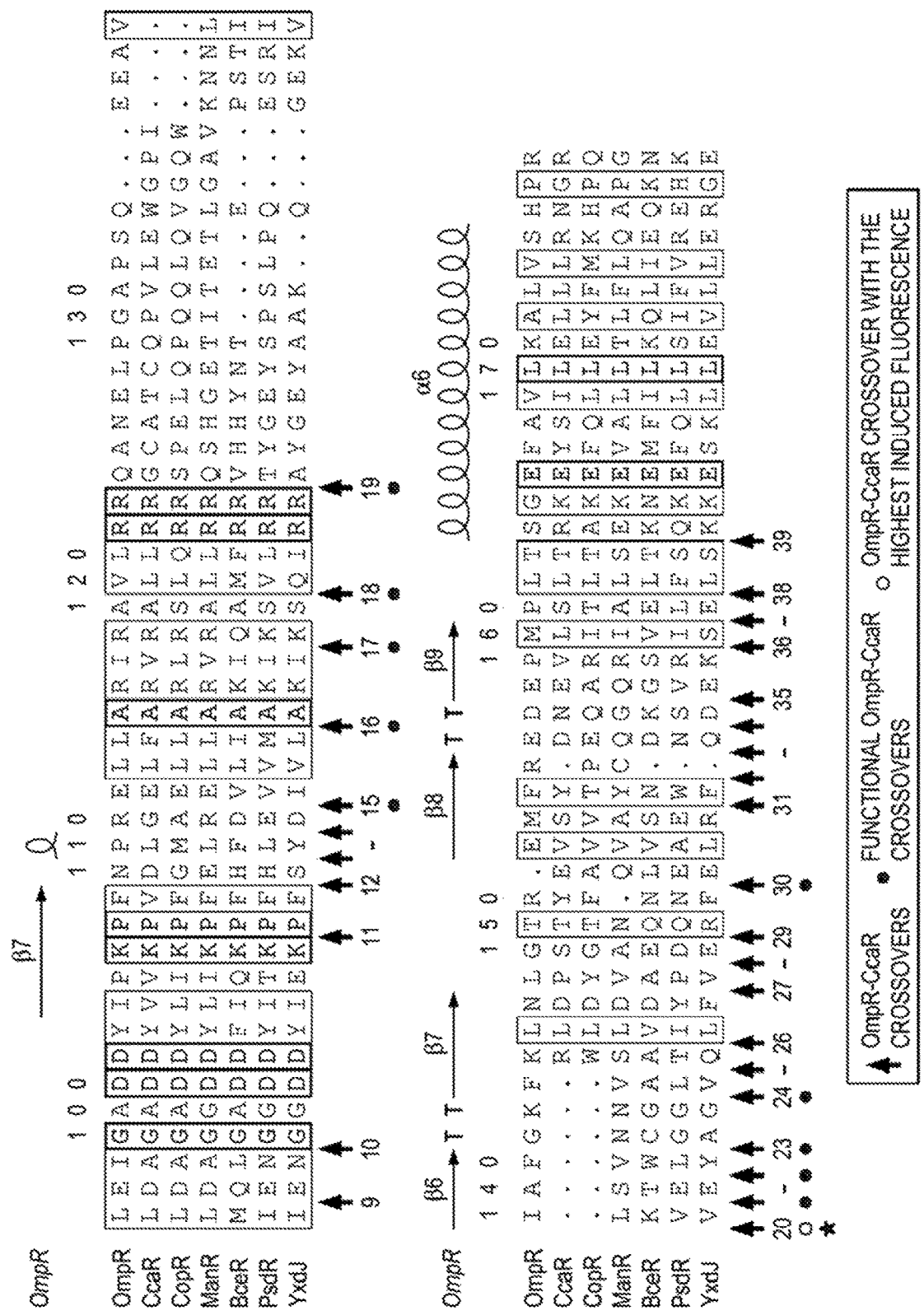
Figure 23C:
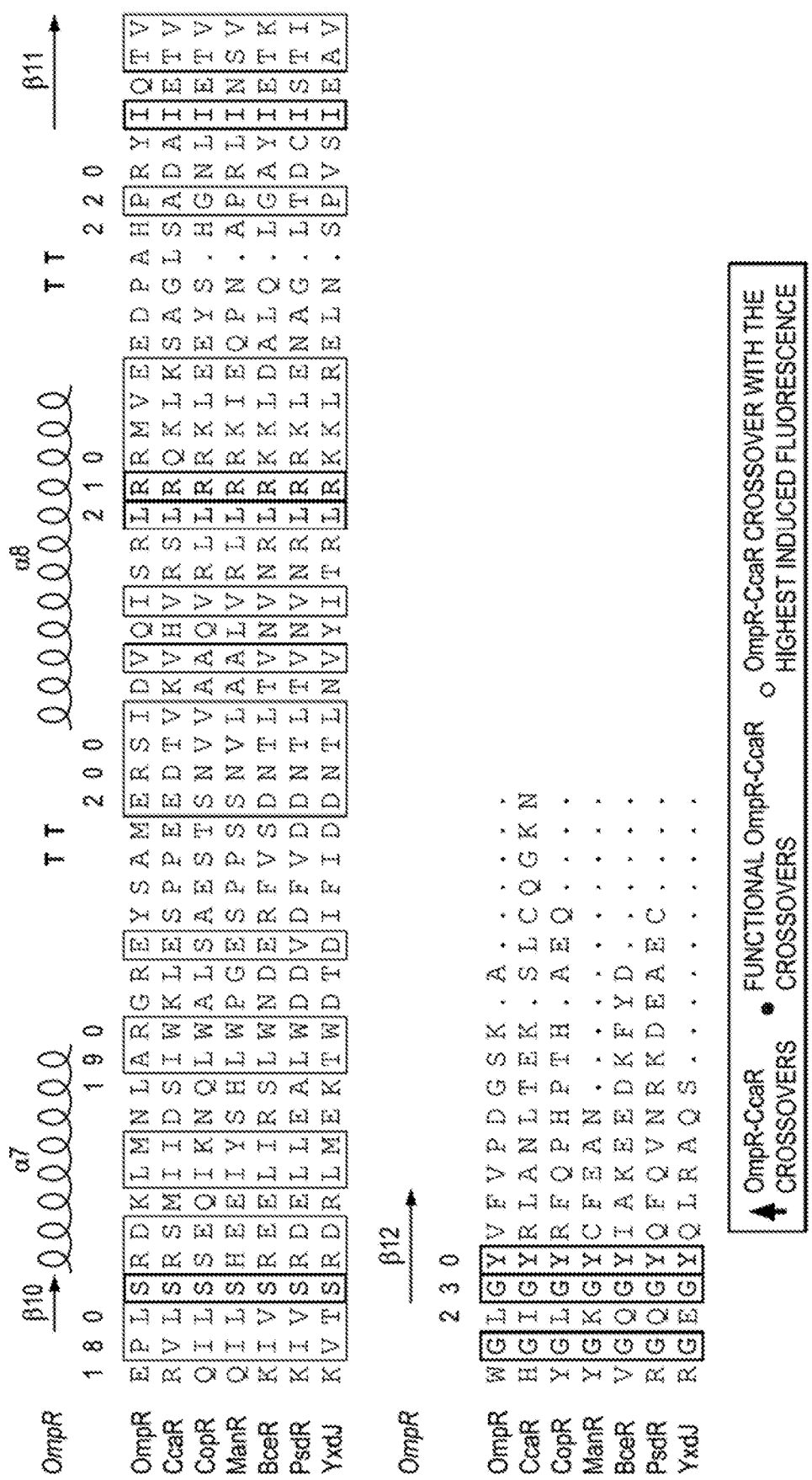
Figure 24:
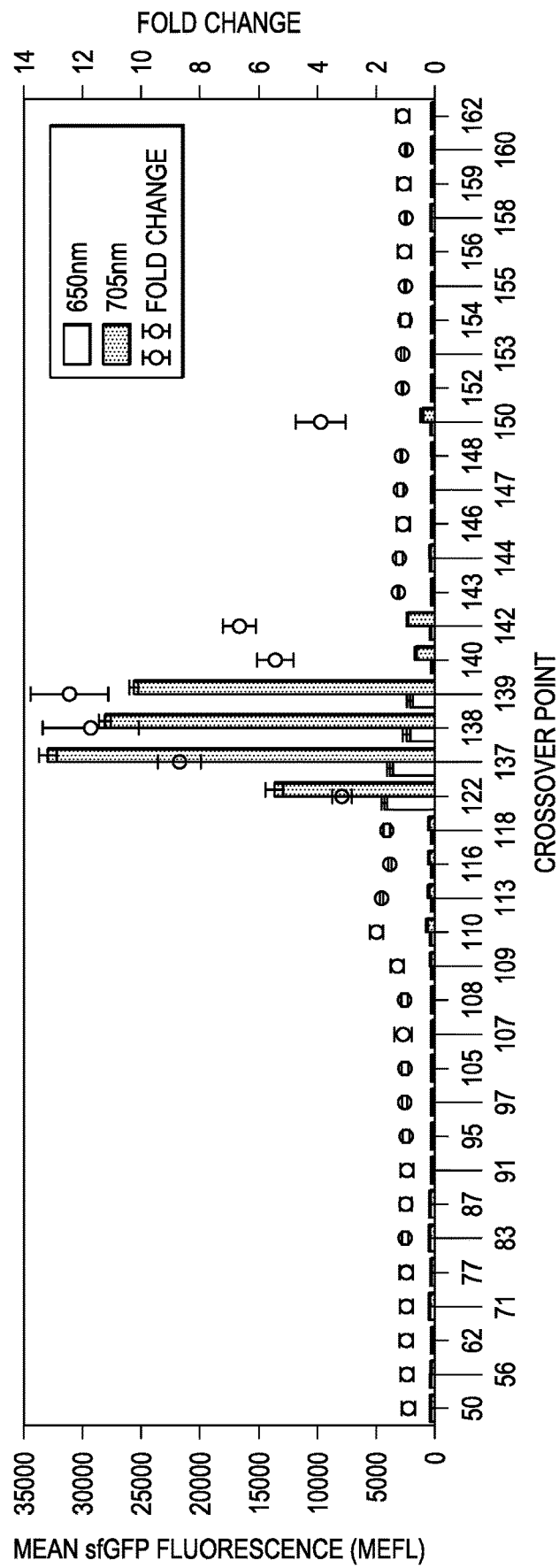
FIG. 24. The various crossover sites tested in the OmpR family, showing the best results are seen with crossover sites in the 120-140 range.
Figure 25:
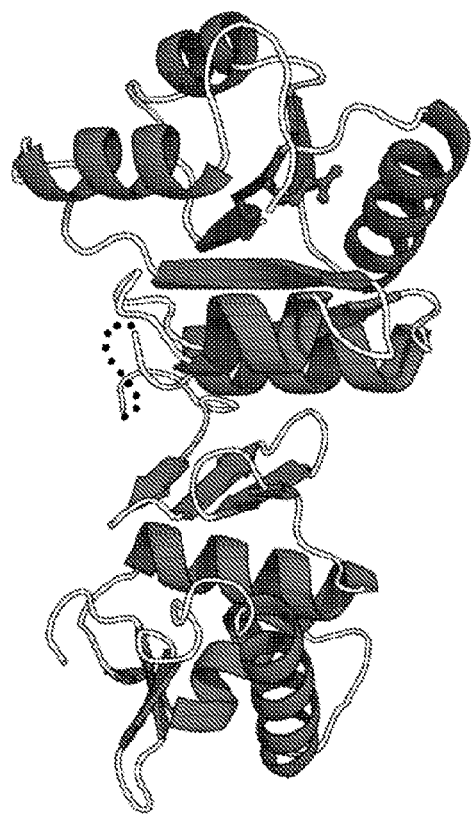
FIG. 25. OmpR 3D structure with the optimal crossover point from the OmpR-CcaR crossover survey highlighted.
Figure 26A:
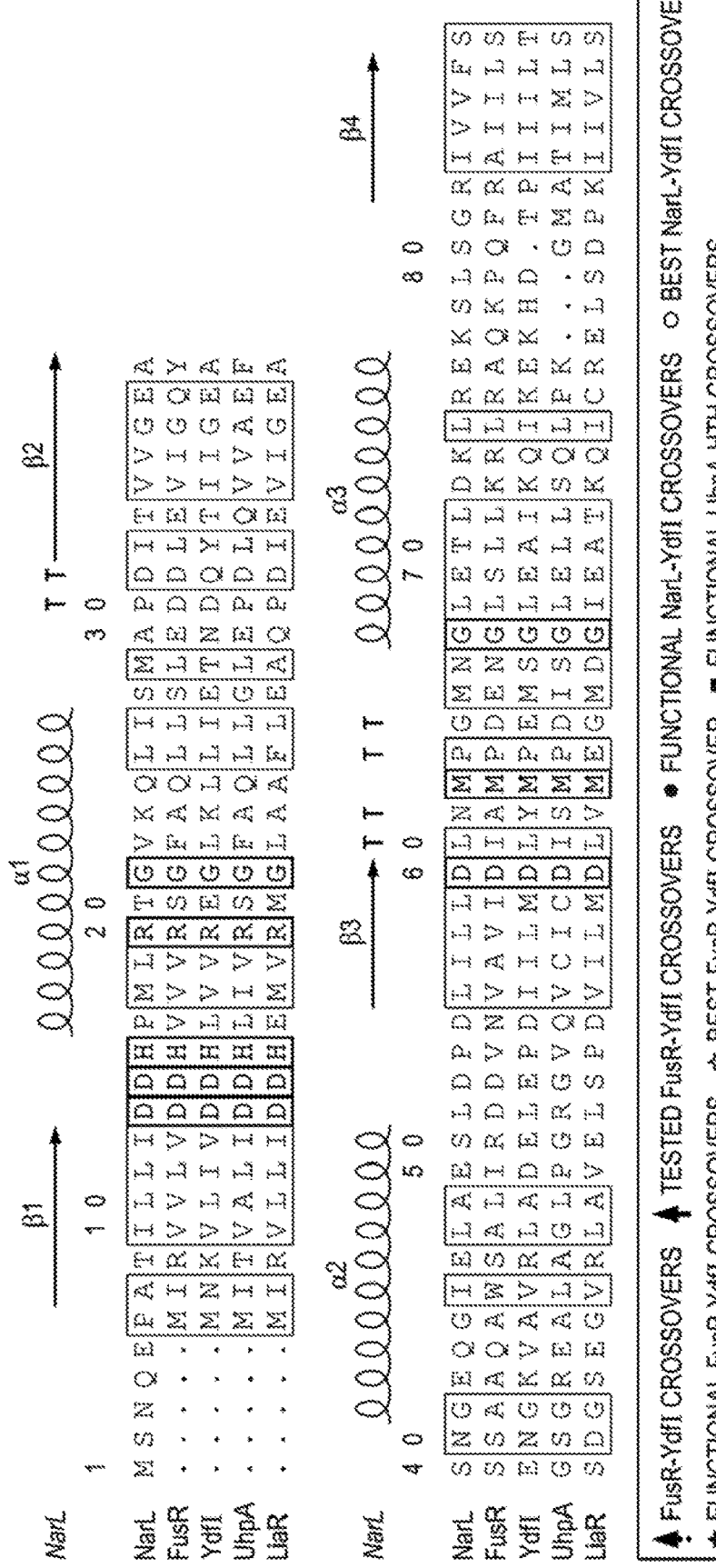
FIG. 26. Alignment of NarL-FixJ family members with crossover points tested and best identified crossover points for specific cross-overs indicated.
Figure 26B:
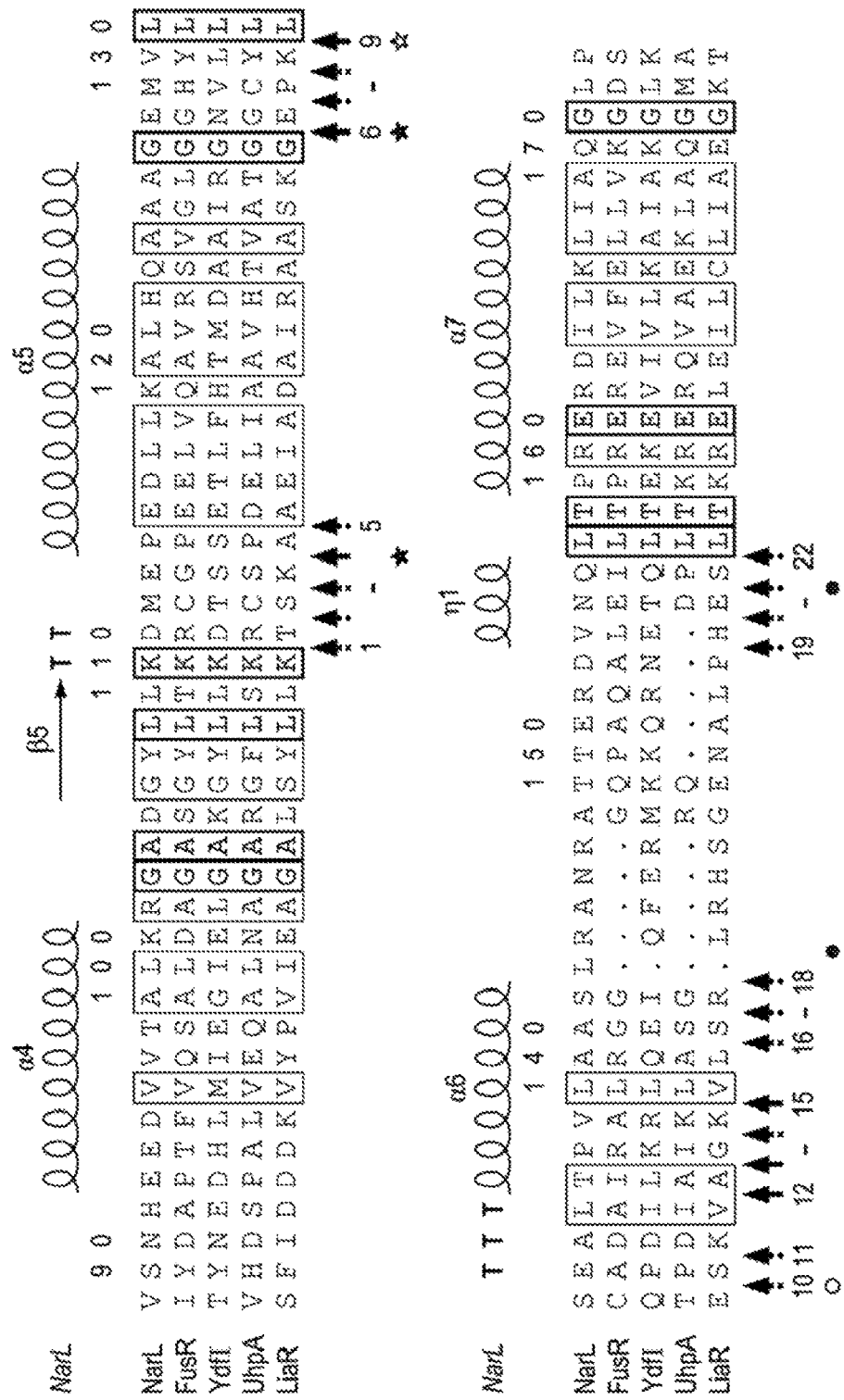
Figure 26C:
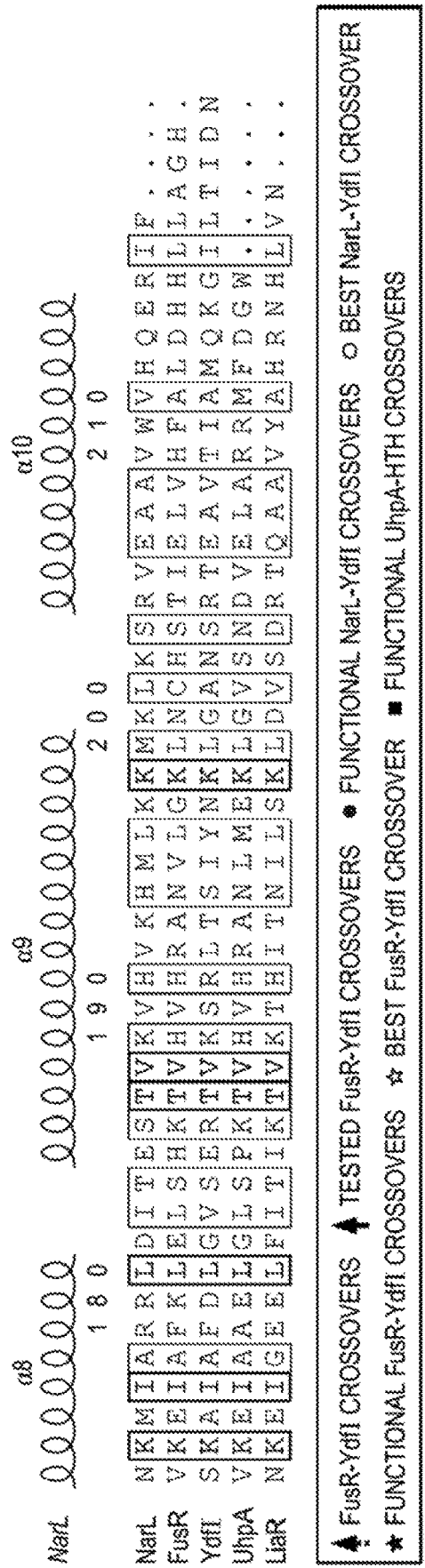
Figure 27:
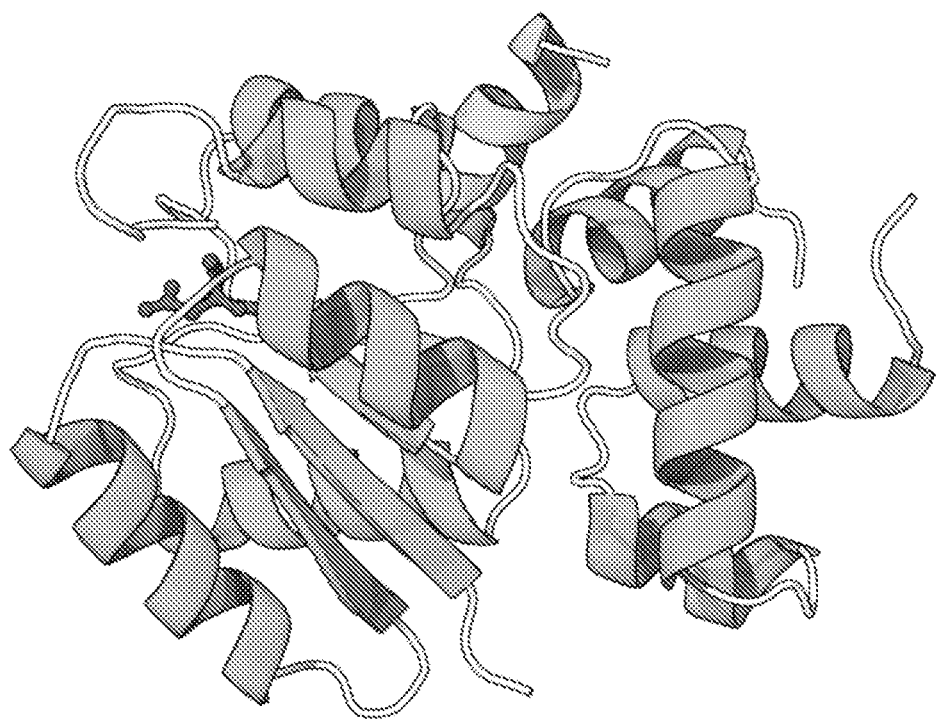
FIG. 27. NarL 3D structure with the optimal crossover point from the NarL-YdfI crossover study highlighted.

FIG. 22 shows a compilation of results obtained by testing a wide range of crossover sites in OmpR family RRs. As can be seen, successful separation occurs in the range of amino acid 110-151. FIG. 23 provides additional detail, and it can be see that the best separation sites are about 120-140, especially, 122, 137, 138 and 139. All amino acid sequences are numbered according to their alignment with OmpR.

We have also shown that certain TCSs cannot be transported from one bacterium into different species due to incompatibilities of the native DBD with the transcriptional apparatus in the target or host bacterium. However, we have shown that DBD rewiring overcomes this challenge, enabling TCSs to be transported between otherwise incompatible species. In particular, replacement of a native DBD from the native organism (wherein the TCS evolved) with that of a DBD from the target organism (where the DBD is to be moved) enables successful transport. Thus, use of a host DBD of known output overcomes expression incompatibilities.

We have also used rewiring to move the nitrate activated TCS NarX-NarL from the gram-negative E. coli to the gram-positive B. subtilis. In particular, we showed that nitrate does not alter gene expression from the E. coli output promoter PdcuS in B. subtilis, likely due to transcriptional incompatibilities. However, we then replaced the DBD of NarL with that of the B. subtilis RR YdfI, and expressed sfGFP from the YdfI-activated PydfJ output promoter. In this system, nitrate strongly activates sfGFP expression, demonstrating that we have used DBD rewiring to transport this TCS from E. coli to B. subtilis.

The fact that we can now move modified TCSs between gram positive and gram-negative bacteria dramatically increases the utility and breadth of the method, allowing us to characterize most computationally identifiable TCSs in the laboratory.

Because we have demonstrated that DBD rewiring is general, and that TCSs can be moved between the major classes of bacteria, this method has potential to be used very widely to determine the inputs sensed by virtually any computationally (or otherwise) identifiable TCS. Our high-throughput approach to developing novel bacterial sensors has wide utility across biotechnology and medicine.

Some major uses are:

1. To better understand the biology of the human microbiome by revealing what the bacteria in and upon our bodies are sensing.

2. To engineer novel diagnostic agents for a wide range of chemical and physical signals within or upon the human body.

3. To engineer novel biosensors for a wide range of chemical and physical signals in the environment (e.g. pollutants, toxins, chemical weapons, pathogenic bacteria, etc.)

4. To engineer "smart probiotics" that secrete therapeutic molecules in the body only in the presence of biomarkers that indicate a diseased state.

5. To engineer metabolic sensors for "smart" fermentation strains that can detect diverse ranges of feedstocks, metabolic intermediates, fermenter conditions, and so on, and tune gene expression for optimal product yields in response.

6. To understand existing complex bacterial regulatory machinery—by replacing native TCSs with unknown outputs with our known TCSs using our technique, we could identify and uncover existing modes of regulation with relevance to elucidating antibiotic resistance or novel therapeutic strategies.

Most evolved bacteria in which TCSs naturally occur cannot be cultured nor genetically manipulated in the laboratory. This makes studying their function highly difficult. Additionally, it is computationally difficult to identify the output promoters of most TCSs, meaning one must perform screens to identify their input signals, yet screening methods are very difficult where there are no culturing methods available. Our method overcomes these problems for virtually all TCSs, rendering identification of their inputs much easier. Our method also inherently generates an engineered biosensor for the molecule sensed by the new TCS.

The above experiments are repeated in Bacillus subtilis. The same genes can be used, especially since Bacillus has no significant codon bias. A protease-deficient strain like WB800N is preferably used for greater stability of heterologous protein. The E. coli-B. subtilis shuttle vector pMTLBS72 exhibiting full structural stability can be used to move the genes easily to a more suitable vector for Bacillus. Alternatively, two vectors pHT01 and pHT43 allow high-level expression of recombinant proteins within the cytoplasm. As yet another alternative, plasmids using the theta-mode of replication such as those derived from the natural plasmids pAMβ1 and pBS72 can be used. Several other suitable expression systems are available.

Our future plans include use of the method to characterize other TCSs from the human microbiome. We also plan to use the method to characterize other TCSs from marine and other environmental bacteria. We hope to characterize hundreds of novel TCSs overall in the coming three years and generate a large number of biological sensors for a variety of chemicals and other inputs.

Each of the following citations is incorporated by reference herein in its entirety for all purposes.

US20030049799 Engineered stimulus-responsive switches.
U.S. Pat. No. 9,062,320 Biological systems input-output response system and plant sentinels
Allen, et al. Genetic Evidence that the α5 Helix of the Receiver Domain of PhoB Is Involved in Interdomain Interactions, J. Bacteriology 183(72001): 2204-2211 (2001).
Castillo-Hair, S. M., et al., How to train your microbe: methods for dynamically characterizing gene networks, Current opinion in microbiology 24, 113-123 (2015).
da Silva D. P. et al., Studies on synthetic LuxR solo hybrids, Front. Cell. Infect. Microbiol., Vl. 5, Art. 52 (2015).
Howell, et al, Genes controlled by the essential YycG/YycF two component system of *Bacillus subtilis* revealed through a novel hybrid regulator approach, Molecular Microbiology, 49(6) 1639-1655 (2003).
Kohanski, M. A., & Collins J. J., Rewiring Bacteria, Two Components at a Time, Cell 133: 947-948 (2008).
Levskaya, A., et al., Synthetic biology: engineering *Escherichia coli* to see light, Nature 438 (7067), 441-442 (2005).
Ryan, R. et al., Toward rationally redesigning bacterial two-component signaling systems using coevolutionary information, PNAS 111(5): E563-E571 (2014).
Schmidl, S. R., et al., Refactoring and optimization of light-switchable *Escherichia coli* two-component systems, ACS synthetic biology 3 (11), 820-831 (2014).
Skerker, J. M., et al., Rewiring the Specificity of Two-Component Signal Transduction Systems, Cell. 133(6): 1043-1054 (2008).
Tabor, J. J., et al., A synthetic genetic edge detection program, Cell 137 (7), 1272-1281 (2009).
Tabor, J. J., et al., Performance characteristics for sensors and circuits used to program *E. coli*, Systems Biology and Biotechnology of *Escherichia coli*, 401-4397 (2009).
Tabor J J, et al., Multichromatic Control of Gene Expression in *Escherichia coli*. J Mol Biol 405:315-324 (2010).
Tapparel et al. The DNA-binding domain of the *Escherichia coli* CpxR two-component response regulator is constitutively active and cannot be fully attenuated by fused adjacent heterologous regulatory domains, Microbiology 152: 431-441 (2006).
Walthers et al. Interdomain Linkers of Homologous Response Regulators Determine Their Mechanism of Action, J. Bacteriology January 185(1): 317-324 (2003).
Wang, B., et al., Rewiring cell signalling through chimaeric regulatory protein engineering, Biochem. Soc. Trans. (2013) 41, 1195-1200 (2013).

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope. It is also intended that any detail anywhere in the claims or anywhere in the specification can be combined with any other detail herein, even if not yet expressly so combined, as the specification would be of inordinate length if we were to recite all possible combinations of DBDs, reporter genes, promoters, host species, and the like.

The invention claimed is:

1. A genetically engineered bacteria, comprising:
   a) a modified two-component sensor system (TCS), said TCS comprising:
      i) a wild-type sensor histidine kinase (SK) comprising a sensing domain operably coupled to a kinase domain; and
      ii) a modified response regulator (RR) that is cognate to said SK, said RR comprising a cognate receiver domain (REC) operably coupled to a non-cognate DNA binding domain (DBD) of known functionality; and
   b) a reporter gene under the control of a promoter containing an operator site that is bound by said DBD, such that said reporter gene is activated or repressed when said SK signals to said modified RR and said DBD binds to said DNA binding site.

2. The bacteria of claim 1, wherein said SK and RR are members of an OmpR-PhoB family of TCSs or a member of a NarL-FixJ family of TCSs.

3. The bacteria of claim 2, wherein:
a) said TCS is a member of the OmpR-PhoB family and said REC is separated from its wild-type DBD at a crossover site between amino acids 110 and 151, said amino acids numbered according to alignment with wild-type OmpR, or
b) said TCS is a member of the NarL-FixJ family and said REC is separated from its wild-type DBD at a crossover site between amino acids 110 and 155, said amino acids numbered according to alignment with wild-type NarL.

4. The bacteria of claim 2, wherein:
a) said TCS is of the OmpR-PhoB family and said REC is separated from its wild-type DBD at a crossover site at amino acid 122, 137, 138 or 139, said amino acids numbered according to alignment with wild-type OmpR; or
b) said TCS is of the NarL-FixJ family, and said REC is separated from its wild-type DBD at a crossover site at amino acid 113, 127, 130, 132, 142 or 154, said amino acids numbered according to alignment with wild-type NarL.

5. The bacteria of claim 1, where said bacteria is gram-positive and said TCS is from a gram-negative species, or vice versa.

6. The bacteria of claim 1, wherein both of said bacteria and said TCS are from a gram-negative species, or both of said bacteria and said TCS are from a gram-positive species.

7. The bacteria of claim 1, where said bacteria is the same bacterium wherein which said TCS evolved.

8. The bacteria of claim 1, having one or more inducible expression vectors encoding said SK and said modified RR.

9. The bacteria of claim 1, said reporter gene being encoded on an expression vector.

10. The bacteria of claim 1, said reporter gene being integrated into a genome of said bacteria.

11. The bacteria of claim 1, wherein said kinase domain is a bi-functional kinase and phosphatase domain.

12. A method of identifying an input signal that activates a sensor histidine kinase, comprising:
a) applying a test input to the bacteria of claim 1;
b) determining whether said test input changes expression of said reporter gene;
and,
c) repeating steps a and b until an input signal that changes said reporter gene expression is identified.

13. The bacteria of claim 1, wherein said SK and said REC and said reporter gene are non-native to said bacteria, and said DBD is native to said bacteria.

* * * * *

SEQUENCE LISTING

```
<160> NUMBER OF SEQ ID NOS: 37

<210> SEQ ID NO 1
<211> LENGTH: 239
<212> TYPE: PRT
<213> ORGANISM: E. coli
<220> FEATURE:
<221> NAME/KEY: misc_feature
<222> LOCATION: (1)..(239)
<223> OTHER INFORMATION: OmpR (E. coli)

<400> SEQUENCE: 1

Met Gln Glu Asn Tyr Lys Ile Leu Val Val Asp Asp Met Arg Leu
1               5                   10                  15

Arg Ala Leu Leu Glu Arg Tyr Leu Thr Glu Gln Gly Phe Gln Val Arg
                20                  25                  30

Ser Val Ala Asn Ala Glu Gln Met Asp Arg Leu Leu Thr Arg Glu Ser
            35                  40                  45

Phe His Leu Met Val Leu Asp Leu Met Leu Pro Gly Glu Asp Gly Leu
        50                  55                  60

Ser Ile Cys Arg Arg Leu Arg Ser Gln Ser Asn Pro Met Pro Ile Ile
65                  70                  75                  80

Met Val Thr Ala Lys Gly Glu Glu Val Asp Arg Ile Val Gly Leu Glu
                85                  90                  95

Ile Gly Ala Asp Asp Tyr Ile Pro Lys Pro Phe Asn Pro Arg Glu Leu
            100                 105                 110
```

Leu Ala Arg Ile Arg Ala Val Leu Arg Arg Gln Ala Asn Glu Leu Pro
            115                 120                 125

Gly Ala Pro Ser Gln Glu Glu Ala Val Ile Ala Phe Gly Lys Phe Lys
        130                 135                 140

Leu Asn Leu Gly Thr Arg Glu Met Phe Arg Glu Asp Glu Pro Met Pro
145                 150                 155                 160

Leu Thr Ser Gly Glu Phe Ala Val Leu Lys Ala Leu Val Ser His Pro
                165                 170                 175

Arg Glu Pro Leu Ser Arg Asp Lys Leu Met Asn Leu Ala Arg Gly Arg
            180                 185                 190

Glu Tyr Ser Ala Met Glu Arg Ser Ile Asp Val Gln Ile Ser Arg Leu
        195                 200                 205

Arg Arg Met Val Glu Glu Asp Pro Ala His Pro Arg Tyr Ile Gln Thr
    210                 215                 220

Val Trp Gly Leu Gly Tyr Val Phe Val Pro Asp Gly Ser Lys Ala
225                 230                 235

<210> SEQ ID NO 2
<211> LENGTH: 234
<212> TYPE: PRT
<213> ORGANISM: Synechocystis sp. PCC 6803
<220> FEATURE:
<221> NAME/KEY: misc_feature
<222> LOCATION: (1)..(234)
<223> OTHER INFORMATION: CcaR (Synechocystis PCC6803)

<400> SEQUENCE: 2

Met Arg Ile Leu Leu Val Glu Asp Asp Leu Pro Leu Ala Glu Thr Leu
1               5                   10                  15

Ala Glu Ala Leu Ser Asp Gln Leu Tyr Thr Val Asp Ile Ala Thr Asp
            20                  25                  30

Ala Ser Leu Ala Trp Asp Tyr Ala Ser Arg Leu Glu Tyr Asp Leu Val
        35                  40                  45

Ile Leu Asp Val Met Leu Pro Glu Leu Asp Gly Ile Thr Leu Cys Gln
    50                  55                  60

Lys Trp Arg Ser His Ser Tyr Leu Met Pro Ile Leu Met Met Thr Ala
65                  70                  75                  80

Arg Asp Thr Ile Asn Asp Lys Ile Thr Gly Leu Asp Ala Gly Ala Asp
                85                  90                  95

Asp Tyr Val Val Lys Pro Val Asp Leu Gly Glu Leu Phe Ala Arg Val
            100                 105                 110

Arg Ala Leu Leu Arg Arg Gly Cys Ala Thr Cys Gln Pro Val Leu Glu
        115                 120                 125

Trp Gly Pro Ile Arg Leu Asp Pro Ser Thr Tyr Glu Val Ser Tyr Asp
    130                 135                 140

Asn Glu Val Leu Ser Leu Thr Arg Lys Glu Tyr Ser Ile Leu Glu Leu
145                 150                 155                 160

Leu Leu Arg Asn Gly Arg Arg Val Leu Ser Arg Ser Met Ile Ile Asp
                165                 170                 175

Ser Ile Trp Lys Leu Glu Ser Pro Pro Glu Glu Asp Thr Val Lys Val
            180                 185                 190

His Val Arg Ser Leu Arg Gln Lys Leu Lys Ser Ala Gly Leu Ser Ala
        195                 200                 205

Asp Ala Ile Glu Thr Val His Gly Ile Gly Tyr Arg Leu Ala Asn Leu
    210                 215                 220

Thr Glu Lys Ser Leu Cys Gln Gly Lys Asn
225                 230

<210> SEQ ID NO 3
<211> LENGTH: 232
<212> TYPE: PRT
<213> ORGANISM: Synechocystis sp. PCC 6803
<220> FEATURE:
<221> NAME/KEY: misc_feature
<222> LOCATION: (1)..(232)
<223> OTHER INFORMATION: CopR (Synechocystis PCC 6803)

<400> SEQUENCE: 3

Met Arg Leu Leu Leu Val Glu Asp Glu Pro Asp Leu Gly Met Ala Leu
1               5                   10                  15

Glu Lys Ala Leu Arg Arg Glu Asn Tyr Val Val Asp Trp Val Gln Asp
                20                  25                  30

Gly Asn Leu Ala Trp Ser Tyr Leu Asp Gln Gly Trp Val Asn Tyr Thr
            35                  40                  45

Leu Ala Ile Phe Asp Trp Met Val Pro Gly Leu Ser Gly Leu Glu Leu
    50                  55                  60

Cys Gln Lys Leu Arg Gly Gln Arg Ser Ser Leu Pro Ile Leu Met Leu
65                  70                  75                  80

Thr Ala Lys Asp Gln Ile Ala Asp Arg Val Glu Gly Leu Asp Ala Gly
                85                  90                  95

Ala Asp Asp Tyr Leu Ile Lys Pro Phe Gly Met Ala Glu Leu Leu Ala
            100                 105                 110

Arg Leu Arg Ser Leu Gln Arg Arg Ser Pro Glu Leu Gln Pro Gln Gln
        115                 120                 125

Leu Gln Val Gly Gln Trp Trp Leu Asp Tyr Gly Thr Phe Ala Val Val
    130                 135                 140

Thr Pro Glu Gln Ala Arg Ile Thr Leu Thr Ala Lys Glu Phe Gln Leu
145                 150                 155                 160

Leu Glu Tyr Phe Met Lys His Pro Gln Gln Ile Leu Ser Ser Glu Gln
                165                 170                 175

Ile Lys Asn Gln Leu Trp Ala Leu Ser Ala Glu Ser Thr Ser Asn Val
            180                 185                 190

Val Ala Ala Gln Val Arg Leu Leu Arg Arg Lys Leu Glu Glu Tyr Ser
        195                 200                 205

His Gly Asn Leu Ile Glu Thr Val Tyr Gly Leu Gly Tyr Arg Phe Gln
    210                 215                 220

Pro His Pro Thr His Ala Glu Gln
225                 230

<210> SEQ ID NO 4
<211> LENGTH: 234
<212> TYPE: PRT
<213> ORGANISM: Synechocystis sp. PCC 6803
<220> FEATURE:
<221> NAME/KEY: misc_feature
<222> LOCATION: (1)..(234)
<223> OTHER INFORMATION: ManR (Synechocystis PCC6803)

<400> SEQUENCE: 4

Met Ala Asn Ile Leu Leu Val Asp Asp Glu Asn Ala Leu Thr Glu Pro
1               5                   10                  15

Leu Ser Lys Ala Leu Gly His Gln Gly His Thr Ile Asp Val Ala Asp
                20                  25                  30

Gln Gly Lys Thr Gly Leu Ala Met Ala Ile Ala Gly Gln Tyr Asp Leu

```
                35                  40                  45
Leu Ile Leu Asp Trp Met Leu Pro Gln Val Ser Gly Leu Glu Ile Cys
 50                  55                  60

Arg Gln Ile Arg Ile Leu Gly His Ser Thr Pro Val Leu Phe Leu Thr
 65                  70                  75                  80

Ala Lys Asp Thr Leu Asp Asp Arg Val Ala Gly Leu Asp Ala Gly Gly
                 85                  90                  95

Asp Asp Tyr Leu Ile Lys Pro Phe Glu Leu Arg Glu Leu Leu Ala Arg
                100                 105                 110

Val Arg Ala Leu Leu Arg Arg Gln Ser His Gly Glu Thr Ile Thr Glu
            115                 120                 125

Thr Leu Gly Ala Val Lys Asn Asn Leu Leu Ser Val Asn Asn Val Ser
130                 135                 140

Leu Asp Val Ala Asn Gln Val Ala Tyr Cys Gln Gly Gln Arg Ile Ala
145                 150                 155                 160

Leu Ser Glu Lys Glu Val Ala Leu Leu Thr Leu Phe Leu Gln Ala Pro
                165                 170                 175

Gly Gln Ile Leu Ser His Glu Ile Tyr Ser His Leu Trp Pro Gly
            180                 185                 190

Glu Ser Pro Pro Ser Ser Asn Val Leu Ala Ala Leu Val Arg Leu Leu
            195                 200                 205

Arg Arg Lys Ile Glu Gln Pro Asn Ala Pro Arg Leu Ile Asn Ser Val
210                 215                 220

Tyr Gly Lys Gly Tyr Cys Phe Glu Ala Asn
225                 230

<210> SEQ ID NO 5
<211> LENGTH: 231
<212> TYPE: PRT
<213> ORGANISM: B. subtilis
<220> FEATURE:
<221> NAME/KEY: misc_feature
<222> LOCATION: (1)..(231)
<223> OTHER INFORMATION: BceR (B. subtilis)

<400> SEQUENCE: 5

Met Phe Lys Leu Leu Ile Glu Asp Asp Glu Ser Leu Phe His Glu
 1               5                  10                  15

Ile Lys Asp Arg Leu Thr Gly Trp Ser Tyr Asp Val Tyr Gly Ile Gln
                 20                  25                  30

Asp Phe Ser Gln Val Leu Gln Glu Phe Ala Ala Val Asn Pro Asp Cys
             35                  40                  45

Val Ile Ile Asp Val Gln Leu Pro Lys Phe Asp Gly Phe His Trp Cys
 50                  55                  60

Arg Leu Ile Arg Ser Arg Ser Asn Val Pro Ile Leu Phe Leu Ser Ser
 65                  70                  75                  80

Arg Asp His Pro Ala Asp Met Val Met Ser Met Gln Leu Gly Ala Asp
                 85                  90                  95

Asp Phe Ile Gln Lys Pro Phe His Phe Asp Val Leu Ile Ala Lys Ile
                100                 105                 110

Gln Ala Met Phe Arg Arg Val His His Tyr Asn Thr Glu Pro Ser Thr
            115                 120                 125

Ile Lys Thr Trp Cys Gly Ala Ala Val Asp Ala Glu Gln Asn Leu Val
130                 135                 140

Ser Asn Asp Lys Gly Ser Val Glu Leu Thr Lys Asn Glu Met Phe Ile
145                 150                 155                 160
```

```
Leu Lys Gln Leu Ile Glu Gln Lys Asn Lys Ile Val Ser Arg Glu Glu
                165                 170                 175

Leu Ile Arg Ser Leu Trp Asn Asp Glu Arg Phe Val Ser Asp Asn Thr
            180                 185                 190

Leu Thr Val Asn Val Asn Arg Leu Arg Lys Lys Leu Asp Ala Leu Gln
        195                 200                 205

Leu Gly Ala Tyr Ile Glu Thr Lys Val Gly Gln Gly Tyr Ile Ala Lys
    210                 215                 220

Glu Glu Asp Lys Phe Tyr Asp
225                 230

<210> SEQ ID NO 6
<211> LENGTH: 237
<212> TYPE: PRT
<213> ORGANISM: B. subtilis
<220> FEATURE:
<221> NAME/KEY: misc_feature
<222> LOCATION: (1)..(237)
<223> OTHER INFORMATION: PsdR (B. subtilis)

<400> SEQUENCE: 6

Met Tyr Arg Ile Leu Leu Val Glu Asp Asp Glu Arg Ile Ala Ser Leu
1               5                   10                  15

Leu Gly Gly His Leu Gln Lys Tyr Gly Tyr Glu Val Lys Ile Ala Glu
            20                  25                  30

Gln Leu Asn Asp Ile Lys Leu Glu Phe Ala Glu Met Lys Pro Asp Leu
        35                  40                  45

Val Leu Leu Asp Ile Asn Leu Pro Phe Phe Asp Gly Phe Tyr Trp Cys
    50                  55                  60

Arg Gln Ile Arg Thr Ile Ser Asn Ala Pro Ile Ile Phe Ile Ser Ala
65                  70                  75                  80

Arg Thr Asp Glu Leu Asn Gln Val Met Ala Ile Glu Asn Gly Gly Asp
                85                  90                  95

Asp Tyr Ile Thr Lys Pro Phe His Leu Glu Val Val Met Ala Lys Ile
            100                 105                 110

Lys Ser Val Leu Arg Arg Thr Tyr Gly Glu Tyr Ser Pro Ser Leu Pro
        115                 120                 125

Gln Glu Ser Arg Ile Val Glu Leu Gly Gly Leu Thr Ile Tyr Pro Asp
    130                 135                 140

Gln Asn Glu Ala Glu Trp Asn Ser Val Arg Ile Leu Phe Ser Gln Lys
145                 150                 155                 160

Glu Phe Gln Leu Leu Ser Ile Phe Val Arg Glu His Lys Lys Ile Val
                165                 170                 175

Ser Arg Asp Glu Leu Leu Glu Ala Leu Trp Asp Asp Val Asp Phe Val
            180                 185                 190

Asp Asp Asn Thr Leu Thr Val Asn Val Asn Arg Leu Arg Arg Lys Leu
        195                 200                 205

Glu Asn Ala Gly Leu Thr Asp Cys Ile Ser Thr Ile Arg Gly Gln Gly
    210                 215                 220

Tyr Gln Phe Gln Val Asn Arg Lys Asp Glu Ala Glu Cys
225                 230                 235

<210> SEQ ID NO 7
<211> LENGTH: 229
<212> TYPE: PRT
<213> ORGANISM: B. subtilis
<220> FEATURE:
```

<221> NAME/KEY: misc_feature
<222> LOCATION: (1)..(229)
<223> OTHER INFORMATION: YxdJ (B. subtilis)

<400> SEQUENCE: 7

```
Met Asn Lys Ile Met Ile Val Glu Asp Ser Glu Asp Ile Arg Gly Leu
1               5                   10                  15

Leu Gln Asn Tyr Leu Glu Lys Tyr Gly Tyr Gln Thr Val Val Ala Ala
            20                  25                  30

Asp Phe Thr Ala Val Leu Asp Val Phe Leu Arg Glu Lys Pro Asp Val
        35                  40                  45

Val Leu Leu Asp Ile Asn Leu Pro Ala Tyr Asp Gly Tyr Tyr Trp Cys
    50                  55                  60

Arg Gln Ile Arg Gln His Ser Thr Ser Pro Ile Ile Phe Ile Ser Ala
65                  70                  75                  80

Arg Ser Gly Glu Met Asp Gln Val Met Ala Ile Glu Asn Gly Gly Asp
                85                  90                  95

Asp Tyr Ile Glu Lys Pro Phe Ser Tyr Asp Ile Val Leu Ala Lys Ile
            100                 105                 110

Lys Ser Gln Ile Arg Arg Ala Tyr Gly Glu Tyr Ala Ala Lys Gln Gly
        115                 120                 125

Glu Lys Val Val Glu Tyr Ala Gly Val Gln Leu Phe Val Glu Arg Phe
    130                 135                 140

Glu Leu Arg Phe Gln Asp Glu Lys Ser Glu Leu Ser Lys Lys Glu Ser
145                 150                 155                 160

Lys Leu Leu Glu Val Leu Leu Glu Arg Gly Lys Val Thr Ser Arg
                165                 170                 175

Asp Arg Leu Met Glu Lys Thr Trp Asp Thr Asp Ile Phe Ile Asp Asp
            180                 185                 190

Asn Thr Leu Asn Val Tyr Ile Thr Arg Leu Arg Lys Lys Leu Arg Glu
        195                 200                 205

Leu Asn Ala Pro Val Ser Ile Glu Ala Val Arg Gly Glu Gly Tyr Gln
    210                 215                 220

Leu Arg Ala Gln Ser
225
```

<210> SEQ ID NO 8
<211> LENGTH: 242
<212> TYPE: PRT
<213> ORGANISM: B. adolescentis
<220> FEATURE:
<221> NAME/KEY: misc_feature
<222> LOCATION: (1)..(242)
<223> OTHER INFORMATION: BAD_0569 (B. adolescentis)

<400> SEQUENCE: 8

```
Met Ser Lys Pro Ile Glu Ala Ser Ile Val Val Asp Asp Glu Pro
1               5                   10                  15

Ser Ile Arg Glu Leu Leu Val Ala Ser Leu His Phe Ala Gly Phe Glu
            20                  25                  30

Val Asn Thr Ala Ala Ser Gly Ser Glu Ala Ile Glu Val Ile Glu Arg
        35                  40                  45

Leu Gln Pro Asp Leu Ile Val Leu Asp Val Met Leu Pro Asp Ile Asp
    50                  55                  60

Gly Phe Thr Val Thr Arg Arg Ile Arg Gln Glu Gly Ile Thr Thr Pro
65                  70                  75                  80

Val Leu Tyr Leu Thr Ala Arg Asp Asp Thr Gln Asp Lys Val Met Gly
```

```
                    85                  90                  95
Leu Thr Val Gly Gly Asp Asp Tyr Val Thr Lys Pro Phe Ser Leu Glu
            100                 105                 110

Glu Val Val Ala Arg Ile Arg Ala Ile Leu Arg Arg Thr Gln Gln Gln
        115                 120                 125

Val Glu Asp Asp Pro Ile Ile Arg Val Gly Asp Leu Glu Ile Asn Glu
    130                 135                 140

Asp Ser His Asp Val Ser Arg Ala Gly Gln Pro Ile Asp Leu Ser Pro
145                 150                 155                 160

Thr Glu Tyr Lys Leu Leu Arg Tyr Leu Met Asp Asn Glu Gly Arg Val
                165                 170                 175

Leu Ser Lys Ala Gln Ile Leu Asp His Val Trp Gln Tyr Asp Trp Gly
            180                 185                 190

Gly Asp Ala Ala Ile Val Glu Ser Tyr Ile Ser Tyr Leu Arg Lys Lys
        195                 200                 205

Val Asp Gly Ile Val Ile Glu Asp Glu Asn Gly Asp Lys His Lys Val
    210                 215                 220

Thr Pro Leu Ile Glu Thr Lys Arg Gly Ile Gly Tyr Met Ile Arg Ala
225                 230                 235                 240

Pro Lys
```

<210> SEQ ID NO 9
<211> LENGTH: 238
<212> TYPE: PRT
<213> ORGANISM: Artificial Sequence
<220> FEATURE:
<223> OTHER INFORMATION: Synthetic: OmpR-CcaR (122aa)

<400> SEQUENCE: 9

```
Met Gln Glu Asn Tyr Lys Ile Leu Val Val Asp Asp Met Arg Leu
1               5                   10                  15

Arg Ala Leu Leu Glu Arg Tyr Leu Thr Glu Gln Gly Phe Gln Val Arg
            20                  25                  30

Ser Val Ala Asn Ala Glu Gln Met Asp Arg Leu Leu Thr Arg Glu Ser
        35                  40                  45

Phe His Leu Met Val Leu Asp Leu Met Leu Pro Gly Glu Asp Gly Leu
    50                  55                  60

Ser Ile Cys Arg Arg Leu Arg Ser Gln Ser Asn Pro Met Pro Ile Ile
65                  70                  75                  80

Met Val Thr Ala Lys Gly Glu Glu Val Asp Arg Ile Val Gly Leu Glu
                85                  90                  95

Ile Gly Ala Asp Asp Tyr Ile Pro Lys Pro Phe Asn Pro Arg Glu Leu
            100                 105                 110

Leu Ala Arg Ile Arg Ala Val Leu Arg Arg Gly Cys Ala Thr Cys Gln
        115                 120                 125

Pro Val Leu Glu Trp Gly Pro Ile Arg Leu Asp Pro Ser Thr Tyr Glu
    130                 135                 140

Val Ser Tyr Asp Asn Glu Val Leu Ser Leu Thr Arg Lys Glu Tyr Ser
145                 150                 155                 160

Ile Leu Glu Leu Leu Leu Arg Asn Gly Arg Arg Val Leu Ser Arg Ser
                165                 170                 175

Met Ile Ile Asp Ser Ile Trp Lys Leu Glu Ser Pro Pro Glu Glu Asp
            180                 185                 190

Thr Val Lys Val His Val Arg Ser Leu Arg Gln Lys Leu Lys Ser Ala
        195                 200                 205
```

Gly Leu Ser Ala Asp Ala Ile Glu Thr Val His Gly Ile Gly Tyr Arg
    210                 215                 220

Leu Ala Asn Leu Thr Glu Lys Ser Leu Cys Gln Gly Lys Asn
225                 230                 235

<210> SEQ ID NO 10
<211> LENGTH: 245
<212> TYPE: PRT
<213> ORGANISM: Artificial Sequence
<220> FEATURE:
<223> OTHER INFORMATION: Synthetic: OmpR-CcaR (137aa)

<400> SEQUENCE: 10

Met Gln Glu Asn Tyr Lys Ile Leu Val Val Asp Asp Asp Met Arg Leu
1               5                   10                  15

Arg Ala Leu Leu Glu Arg Tyr Leu Thr Glu Gln Gly Phe Gln Val Arg
            20                  25                  30

Ser Val Ala Asn Ala Glu Gln Met Asp Arg Leu Leu Thr Arg Glu Ser
        35                  40                  45

Phe His Leu Met Val Leu Asp Leu Met Leu Pro Gly Glu Asp Gly Leu
    50                  55                  60

Ser Ile Cys Arg Arg Leu Arg Ser Gln Ser Asn Pro Met Pro Ile Ile
65                  70                  75                  80

Met Val Thr Ala Lys Gly Glu Glu Val Asp Arg Ile Val Gly Leu Glu
                85                  90                  95

Ile Gly Ala Asp Asp Tyr Ile Pro Lys Pro Phe Asn Pro Arg Glu Leu
            100                 105                 110

Leu Ala Arg Ile Arg Ala Val Leu Arg Arg Gln Ala Asn Glu Leu Pro
        115                 120                 125

Gly Ala Pro Ser Gln Glu Glu Ala Val Leu Glu Trp Gly Pro Ile Arg
    130                 135                 140

Leu Asp Pro Ser Thr Tyr Glu Val Ser Tyr Asp Asn Glu Val Leu Ser
145                 150                 155                 160

Leu Thr Arg Lys Glu Tyr Ser Ile Leu Glu Leu Leu Arg Asn Gly
                165                 170                 175

Arg Arg Val Leu Ser Arg Ser Met Ile Ile Asp Ser Ile Trp Lys Leu
            180                 185                 190

Glu Ser Pro Pro Glu Glu Asp Thr Val Lys Val His Val Arg Ser Leu
        195                 200                 205

Arg Gln Lys Leu Lys Ser Ala Gly Leu Ser Ala Asp Ala Ile Glu Thr
    210                 215                 220

Val His Gly Ile Gly Tyr Arg Leu Ala Asn Leu Thr Glu Lys Ser Leu
225                 230                 235                 240

Cys Gln Gly Lys Asn
                245

<210> SEQ ID NO 11
<211> LENGTH: 245
<212> TYPE: PRT
<213> ORGANISM: Artificial Sequence
<220> FEATURE:
<223> OTHER INFORMATION: Synthetic: OmpR-CcaR (138aa)

<400> SEQUENCE: 11

Met Gln Glu Asn Tyr Lys Ile Leu Val Val Asp Asp Asp Met Arg Leu
1               5                   10                  15

Arg Ala Leu Leu Glu Arg Tyr Leu Thr Glu Gln Gly Phe Gln Val Arg

```
            20                  25                  30
Ser Val Ala Asn Ala Glu Gln Met Asp Arg Leu Leu Thr Arg Glu Ser
        35                  40                  45

Phe His Leu Met Val Leu Asp Leu Met Leu Pro Gly Glu Asp Gly Leu
    50                  55                  60

Ser Ile Cys Arg Arg Leu Arg Ser Gln Ser Asn Pro Met Pro Ile Ile
65                  70                  75                  80

Met Val Thr Ala Lys Gly Glu Glu Val Asp Arg Ile Val Gly Leu Glu
                85                  90                  95

Ile Gly Ala Asp Asp Tyr Ile Pro Lys Pro Phe Asn Pro Arg Glu Leu
            100                 105                 110

Leu Ala Arg Ile Arg Ala Val Leu Arg Arg Gln Ala Asn Glu Leu Pro
        115                 120                 125

Gly Ala Pro Ser Gln Glu Glu Ala Val Ile Glu Trp Gly Pro Ile Arg
    130                 135                 140

Leu Asp Pro Ser Thr Tyr Glu Val Ser Tyr Asp Asn Glu Val Leu Ser
145                 150                 155                 160

Leu Thr Arg Lys Glu Tyr Ser Ile Leu Glu Leu Leu Arg Asn Gly
                165                 170                 175

Arg Arg Val Leu Ser Arg Ser Met Ile Ile Asp Ser Ile Trp Lys Leu
            180                 185                 190

Glu Ser Pro Pro Glu Glu Asp Thr Val Lys Val His Val Arg Ser Leu
        195                 200                 205

Arg Gln Lys Leu Lys Ser Ala Gly Leu Ser Ala Asp Ala Ile Glu Thr
    210                 215                 220

Val His Gly Ile Gly Tyr Arg Leu Ala Asn Leu Thr Glu Lys Ser Leu
225                 230                 235                 240

Cys Gln Gly Lys Asn
                245

<210> SEQ ID NO 12
<211> LENGTH: 245
<212> TYPE: PRT
<213> ORGANISM: Artificial Sequence
<220> FEATURE:
<223> OTHER INFORMATION: Synthetic: OmpR-CcaR (139aa)

<400> SEQUENCE: 12

Met Gln Glu Asn Tyr Lys Ile Leu Val Val Asp Asp Asp Met Arg Leu
1               5                   10                  15

Arg Ala Leu Leu Glu Arg Tyr Leu Thr Glu Gln Gly Phe Gln Val Arg
            20                  25                  30

Ser Val Ala Asn Ala Glu Gln Met Asp Arg Leu Leu Thr Arg Glu Ser
        35                  40                  45

Phe His Leu Met Val Leu Asp Leu Met Leu Pro Gly Glu Asp Gly Leu
    50                  55                  60

Ser Ile Cys Arg Arg Leu Arg Ser Gln Ser Asn Pro Met Pro Ile Ile
65                  70                  75                  80

Met Val Thr Ala Lys Gly Glu Glu Val Asp Arg Ile Val Gly Leu Glu
                85                  90                  95

Ile Gly Ala Asp Asp Tyr Ile Pro Lys Pro Phe Asn Pro Arg Glu Leu
            100                 105                 110

Leu Ala Arg Ile Arg Ala Val Leu Arg Arg Gln Ala Asn Glu Leu Pro
        115                 120                 125

Gly Ala Pro Ser Gln Glu Glu Ala Val Ile Ala Trp Gly Pro Ile Arg
```

```
            130                 135                 140
Leu Asp Pro Ser Thr Tyr Glu Val Ser Tyr Asp Asn Glu Val Leu Ser
145                 150                 155                 160

Leu Thr Arg Lys Glu Tyr Ser Ile Leu Glu Leu Leu Arg Asn Gly
                165                 170                 175

Arg Arg Val Leu Ser Arg Ser Met Ile Ile Asp Ser Ile Trp Lys Leu
                180                 185                 190

Glu Ser Pro Pro Glu Glu Asp Thr Val Lys Val His Val Arg Ser Leu
                195                 200                 205

Arg Gln Lys Leu Lys Ser Ala Gly Leu Ser Ala Asp Ala Ile Glu Thr
                210                 215                 220

Val His Gly Ile Gly Tyr Arg Leu Ala Asn Leu Thr Glu Lys Ser Leu
225                 230                 235                 240

Cys Gln Gly Lys Asn
                245

<210> SEQ ID NO 13
<211> LENGTH: 245
<212> TYPE: PRT
<213> ORGANISM: Artificial Sequence
<220> FEATURE:
<223> OTHER INFORMATION: Synthetic: OmpR-CcaR (140aa)

<400> SEQUENCE: 13

Met Gln Glu Asn Tyr Lys Ile Leu Val Val Asp Asp Met Arg Leu
1               5                   10                  15

Arg Ala Leu Leu Glu Arg Tyr Leu Thr Glu Gln Gly Phe Gln Val Arg
                20                  25                  30

Ser Val Ala Asn Ala Glu Gln Met Asp Arg Leu Leu Thr Arg Glu Ser
                35                  40                  45

Phe His Leu Met Val Leu Asp Leu Met Leu Pro Gly Glu Asp Gly Leu
            50                  55                  60

Ser Ile Cys Arg Arg Leu Arg Ser Gln Ser Asn Pro Met Pro Ile Ile
65                  70                  75                  80

Met Val Thr Ala Lys Gly Glu Glu Val Asp Arg Ile Val Gly Leu Glu
                85                  90                  95

Ile Gly Ala Asp Asp Tyr Ile Pro Lys Pro Phe Asn Pro Arg Glu Leu
                100                 105                 110

Leu Ala Arg Ile Arg Ala Val Leu Arg Arg Gln Ala Asn Glu Leu Pro
                115                 120                 125

Gly Ala Pro Ser Gln Glu Glu Ala Val Ile Ala Phe Gly Pro Ile Arg
                130                 135                 140

Leu Asp Pro Ser Thr Tyr Glu Val Ser Tyr Asp Asn Glu Val Leu Ser
145                 150                 155                 160

Leu Thr Arg Lys Glu Tyr Ser Ile Leu Glu Leu Leu Arg Asn Gly
                165                 170                 175

Arg Arg Val Leu Ser Arg Ser Met Ile Ile Asp Ser Ile Trp Lys Leu
                180                 185                 190

Glu Ser Pro Pro Glu Glu Asp Thr Val Lys Val His Val Arg Ser Leu
                195                 200                 205

Arg Gln Lys Leu Lys Ser Ala Gly Leu Ser Ala Asp Ala Ile Glu Thr
                210                 215                 220

Val His Gly Ile Gly Tyr Arg Leu Ala Asn Leu Thr Glu Lys Ser Leu
225                 230                 235                 240

Cys Gln Gly Lys Asn
```

245

<210> SEQ ID NO 14
<211> LENGTH: 245
<212> TYPE: PRT
<213> ORGANISM: Artificial Sequence
<220> FEATURE:
<223> OTHER INFORMATION: Synthetic: OmpR-CcaR (142aa)

<400> SEQUENCE: 14

Met Gln Glu Asn Tyr Lys Ile Leu Val Val Asp Asp Met Arg Leu
1               5                   10                  15

Arg Ala Leu Leu Glu Arg Tyr Leu Thr Glu Gln Gly Phe Gln Val Arg
            20                  25                  30

Ser Val Ala Asn Ala Glu Gln Met Asp Arg Leu Leu Thr Arg Glu Ser
        35                  40                  45

Phe His Leu Met Val Leu Asp Leu Met Leu Pro Gly Glu Asp Gly Leu
    50                  55                  60

Ser Ile Cys Arg Arg Leu Arg Ser Gln Ser Asn Pro Met Pro Ile Ile
65                  70                  75                  80

Met Val Thr Ala Lys Gly Glu Glu Val Asp Arg Ile Val Gly Leu Glu
                85                  90                  95

Ile Gly Ala Asp Asp Tyr Ile Pro Lys Pro Phe Asn Pro Arg Glu Leu
            100                 105                 110

Leu Ala Arg Ile Arg Ala Val Leu Arg Arg Gln Ala Asn Glu Leu Pro
        115                 120                 125

Gly Ala Pro Ser Gln Glu Glu Ala Val Ile Ala Phe Gly Lys Ile Arg
    130                 135                 140

Leu Asp Pro Ser Thr Tyr Glu Val Ser Tyr Asp Asn Glu Val Leu Ser
145                 150                 155                 160

Leu Thr Arg Lys Glu Tyr Ser Ile Leu Glu Leu Leu Arg Asn Gly
                165                 170                 175

Arg Arg Val Leu Ser Arg Ser Met Ile Ile Asp Ser Ile Trp Lys Leu
            180                 185                 190

Glu Ser Pro Pro Glu Glu Asp Thr Val Lys Val His Val Arg Ser Leu
        195                 200                 205

Arg Gln Lys Leu Lys Ser Ala Gly Leu Ser Ala Asp Ala Ile Glu Thr
    210                 215                 220

Val His Gly Ile Gly Tyr Arg Leu Ala Asn Leu Thr Glu Lys Ser Leu
225                 230                 235                 240

Cys Gln Gly Lys Asn
                245

<210> SEQ ID NO 15
<211> LENGTH: 245
<212> TYPE: PRT
<213> ORGANISM: Artificial Sequence
<220> FEATURE:
<223> OTHER INFORMATION: Synthetic: OmpR-CcaR (150aa)

<400> SEQUENCE: 15

Met Gln Glu Asn Tyr Lys Ile Leu Val Val Asp Asp Met Arg Leu
1               5                   10                  15

Arg Ala Leu Leu Glu Arg Tyr Leu Thr Glu Gln Gly Phe Gln Val Arg
            20                  25                  30

Ser Val Ala Asn Ala Glu Gln Met Asp Arg Leu Leu Thr Arg Glu Ser
        35                  40                  45

```
Phe His Leu Met Val Leu Asp Leu Met Leu Pro Gly Glu Asp Gly Leu
 50                  55                  60

Ser Ile Cys Arg Arg Leu Arg Ser Gln Ser Asn Pro Met Pro Ile Ile
 65                  70                  75                  80

Met Val Thr Ala Lys Gly Glu Glu Val Asp Arg Ile Val Gly Leu Glu
                 85                  90                  95

Ile Gly Ala Asp Asp Tyr Ile Pro Lys Pro Phe Asn Pro Arg Glu Leu
                100                 105                 110

Leu Ala Arg Ile Arg Ala Val Leu Arg Arg Gln Ala Asn Glu Leu Pro
                115                 120                 125

Gly Ala Pro Ser Gln Glu Glu Ala Val Ile Ala Phe Gly Lys Phe Lys
130                 135                 140

Leu Asn Leu Gly Thr Arg Glu Val Ser Tyr Asp Asn Glu Val Leu Ser
145                 150                 155                 160

Leu Thr Arg Lys Glu Tyr Ser Ile Leu Glu Leu Leu Arg Asn Gly
                165                 170                 175

Arg Arg Val Leu Ser Arg Ser Met Ile Ile Asp Ser Ile Trp Lys Leu
                180                 185                 190

Glu Ser Pro Pro Glu Glu Asp Thr Val Lys Val His Val Arg Ser Leu
                195                 200                 205

Arg Gln Lys Leu Lys Ser Ala Gly Leu Ser Ala Asp Ala Ile Glu Thr
                210                 215                 220

Val His Gly Ile Gly Tyr Arg Leu Ala Asn Leu Thr Glu Lys Ser Leu
225                 230                 235                 240

Cys Gln Gly Lys Asn
                245

<210> SEQ ID NO 16
<211> LENGTH: 234
<212> TYPE: PRT
<213> ORGANISM: Artificial Sequence
<220> FEATURE:
<223> OTHER INFORMATION: Synthetic: OmpR-ManR (137aa)

<400> SEQUENCE: 16

Met Gln Glu Asn Tyr Lys Ile Leu Val Val Asp Asp Asp Met Arg Leu
 1               5                  10                  15

Arg Ala Leu Leu Glu Arg Tyr Leu Thr Glu Gln Gly Phe Gln Val Arg
                 20                  25                  30

Ser Val Ala Asn Ala Glu Gln Met Asp Arg Leu Leu Thr Arg Glu Ser
                 35                  40                  45

Phe His Leu Met Val Leu Asp Leu Met Leu Pro Gly Glu Asp Gly Leu
 50                  55                  60

Ser Ile Cys Arg Arg Leu Arg Ser Gln Ser Asn Pro Met Pro Ile Ile
 65                  70                  75                  80

Met Val Thr Ala Lys Gly Glu Glu Val Asp Arg Ile Val Gly Leu Glu
                 85                  90                  95

Ile Gly Ala Asp Asp Tyr Ile Pro Lys Pro Phe Asn Pro Arg Glu Leu
                100                 105                 110

Leu Ala Arg Ile Arg Ala Val Leu Arg Arg Gln Ala Asn Glu Leu Pro
                115                 120                 125

Gly Ala Pro Ser Gln Glu Glu Ala Val Leu Ser Val Asn Asn Val Ser
130                 135                 140

Leu Asp Val Ala Asn Gln Val Ala Tyr Cys Gln Gly Gln Arg Ile Ala
145                 150                 155                 160
```

```
Leu Ser Glu Lys Glu Val Ala Leu Leu Thr Leu Phe Leu Gln Ala Pro
            165                 170                 175

Gly Gln Ile Leu Ser His Glu Glu Ile Tyr Ser His Leu Trp Pro Gly
            180                 185                 190

Glu Ser Pro Ser Ser Asn Val Leu Ala Ala Leu Val Arg Leu Leu
            195                 200                 205

Arg Arg Lys Ile Glu Gln Pro Asn Ala Pro Arg Leu Ile Asn Ser Val
            210                 215                 220

Tyr Gly Lys Gly Tyr Cys Phe Glu Ala Asn
225                 230

<210> SEQ ID NO 17
<211> LENGTH: 241
<212> TYPE: PRT
<213> ORGANISM: Artificial Sequence
<220> FEATURE:
<223> OTHER INFORMATION: Synthetic: OmpR-PsdR (137aa)

<400> SEQUENCE: 17

Met Gln Glu Asn Tyr Lys Ile Leu Val Val Asp Asp Asp Met Arg Leu
1               5                   10                  15

Arg Ala Leu Leu Glu Arg Tyr Leu Thr Glu Gln Gly Phe Gln Val Arg
            20                  25                  30

Ser Val Ala Asn Ala Glu Gln Met Asp Arg Leu Leu Thr Arg Glu Ser
            35                  40                  45

Phe His Leu Met Val Leu Asp Leu Met Leu Pro Gly Glu Asp Gly Leu
        50                  55                  60

Ser Ile Cys Arg Arg Leu Arg Ser Gln Ser Asn Pro Met Pro Ile Ile
65                  70                  75                  80

Met Val Thr Ala Lys Gly Glu Glu Val Asp Arg Ile Val Gly Leu Glu
            85                  90                  95

Ile Gly Ala Asp Asp Tyr Ile Pro Lys Pro Phe Asn Pro Arg Glu Leu
            100                 105                 110

Leu Ala Arg Ile Arg Ala Val Leu Arg Arg Gln Ala Asn Glu Leu Pro
            115                 120                 125

Gly Ala Pro Ser Gln Glu Glu Ala Val Val Glu Leu Gly Gly Leu Thr
            130                 135                 140

Ile Tyr Pro Asp Gln Asn Glu Ala Glu Trp Asn Ser Val Arg Ile Leu
145                 150                 155                 160

Phe Ser Gln Lys Glu Phe Gln Leu Leu Ser Ile Phe Val Arg Glu His
            165                 170                 175

Lys Lys Ile Val Ser Arg Asp Glu Leu Leu Glu Ala Leu Trp Asp Asp
            180                 185                 190

Val Asp Phe Val Asp Asp Asn Thr Leu Thr Val Asn Val Asn Arg Leu
            195                 200                 205

Arg Arg Lys Leu Glu Asn Ala Gly Leu Thr Asp Cys Ile Ser Thr Ile
            210                 215                 220

Arg Gly Gln Gly Tyr Gln Phe Gln Val Asn Arg Lys Asp Glu Ala Glu
225                 230                 235                 240

Cys

<210> SEQ ID NO 18
<211> LENGTH: 235
<212> TYPE: PRT
<213> ORGANISM: Artificial Sequence
<220> FEATURE:
<223> OTHER INFORMATION: Synthetic: OmpR-YxdJ (137aa)
```

```
<400> SEQUENCE: 18

Met Gln Glu Asn Tyr Lys Ile Leu Val Val Asp Asp Met Arg Leu
1               5                   10                  15

Arg Ala Leu Leu Glu Arg Tyr Leu Thr Glu Gln Gly Phe Gln Val Arg
            20                  25                  30

Ser Val Ala Asn Ala Glu Gln Met Asp Arg Leu Leu Thr Arg Glu Ser
            35                  40                  45

Phe His Leu Met Val Leu Asp Leu Met Leu Pro Gly Glu Asp Gly Leu
        50                  55                  60

Ser Ile Cys Arg Arg Leu Arg Ser Gln Ser Asn Pro Met Pro Ile Ile
65                  70                  75                  80

Met Val Thr Ala Lys Gly Glu Glu Val Asp Arg Ile Val Gly Leu Glu
                85                  90                  95

Ile Gly Ala Asp Asp Tyr Ile Pro Lys Pro Phe Asn Pro Arg Glu Leu
            100                 105                 110

Leu Ala Arg Ile Arg Ala Val Leu Arg Arg Gln Ala Asn Glu Leu Pro
        115                 120                 125

Gly Ala Pro Ser Gln Glu Glu Ala Val Val Glu Tyr Ala Gly Val Gln
130                 135                 140

Leu Phe Val Glu Arg Phe Glu Leu Arg Phe Gln Asp Glu Lys Ser Glu
145                 150                 155                 160

Leu Ser Lys Lys Glu Ser Lys Leu Leu Glu Val Leu Leu Glu Arg Gly
                165                 170                 175

Glu Lys Val Thr Ser Arg Asp Arg Leu Met Glu Lys Thr Trp Asp Thr
            180                 185                 190

Asp Ile Phe Ile Asp Asp Asn Thr Leu Asn Val Tyr Ile Thr Arg Leu
        195                 200                 205

Arg Lys Lys Leu Arg Glu Leu Asn Ala Pro Val Ser Ile Glu Ala Val
    210                 215                 220

Arg Gly Glu Gly Tyr Gln Leu Arg Ala Gln Ser
225                 230                 235

<210> SEQ ID NO 19
<211> LENGTH: 230
<212> TYPE: PRT
<213> ORGANISM: Artificial Sequence
<220> FEATURE:
<223> OTHER INFORMATION: Synthetic: CcaR-CopR (137aa)

<400> SEQUENCE: 19

Met Arg Ile Leu Leu Val Glu Asp Asp Leu Pro Leu Ala Glu Thr Leu
1               5                   10                  15

Ala Glu Ala Leu Ser Asp Gln Leu Tyr Thr Val Asp Ile Ala Thr Asp
            20                  25                  30

Ala Ser Leu Ala Trp Asp Tyr Ala Ser Arg Leu Glu Tyr Asp Leu Val
        35                  40                  45

Ile Leu Asp Val Met Leu Pro Glu Leu Asp Gly Ile Thr Leu Cys Gln
    50                  55                  60

Lys Trp Arg Ser His Ser Tyr Leu Met Pro Ile Leu Met Met Thr Ala
65                  70                  75                  80

Arg Asp Thr Ile Asn Asp Lys Ile Thr Gly Leu Asp Ala Gly Ala Asp
                85                  90                  95

Asp Tyr Val Val Lys Pro Val Asp Leu Gly Glu Leu Phe Ala Arg Val
            100                 105                 110
```

```
Arg Ala Leu Leu Arg Arg Gly Cys Ala Thr Cys Gln Pro Val Leu Gln
            115                 120                 125

Val Gly Gln Trp Trp Leu Asp Tyr Gly Thr Phe Ala Val Val Thr Pro
        130                 135                 140

Glu Gln Ala Arg Ile Thr Leu Thr Ala Lys Glu Phe Gln Leu Leu Glu
145                 150                 155                 160

Tyr Phe Met Lys His Pro Gln Gln Ile Leu Ser Ser Glu Gln Ile Lys
                165                 170                 175

Asn Gln Leu Trp Ala Leu Ser Ala Glu Ser Thr Ser Asn Val Val Ala
            180                 185                 190

Ala Gln Val Arg Leu Leu Arg Arg Lys Leu Glu Glu Tyr Ser His Gly
        195                 200                 205

Asn Leu Ile Glu Thr Val Tyr Gly Leu Gly Tyr Arg Phe Gln Pro His
    210                 215                 220

Pro Thr His Ala Glu Gln
225                 230

<210> SEQ ID NO 20
<211> LENGTH: 223
<212> TYPE: PRT
<213> ORGANISM: Artificial Sequence
<220> FEATURE:
<223> OTHER INFORMATION: Synthetic: CcaR-ManR (137aa)

<400> SEQUENCE: 20

Met Arg Ile Leu Leu Val Glu Asp Asp Leu Pro Leu Ala Glu Thr Leu
1               5                   10                  15

Ala Glu Ala Leu Ser Asp Gln Leu Tyr Thr Val Asp Ile Ala Thr Asp
            20                  25                  30

Ala Ser Leu Ala Trp Asp Tyr Ala Ser Arg Leu Glu Tyr Asp Leu Val
        35                  40                  45

Ile Leu Asp Val Met Leu Pro Glu Leu Asp Gly Ile Thr Leu Cys Gln
    50                  55                  60

Lys Trp Arg Ser His Ser Tyr Leu Met Pro Ile Leu Met Met Thr Ala
65                  70                  75                  80

Arg Asp Thr Ile Asn Asp Lys Ile Thr Gly Leu Asp Ala Gly Ala Asp
                85                  90                  95

Asp Tyr Val Val Lys Pro Val Asp Leu Gly Glu Leu Phe Ala Arg Val
            100                 105                 110

Arg Ala Leu Leu Arg Arg Gly Cys Ala Thr Cys Gln Pro Val Leu Ser
        115                 120                 125

Val Asn Asn Val Ser Leu Asp Val Ala Asn Gln Val Ala Tyr Cys Gln
    130                 135                 140

Gly Gln Arg Ile Ala Leu Ser Glu Lys Glu Val Ala Leu Leu Thr Leu
145                 150                 155                 160

Phe Leu Gln Ala Pro Gly Gln Ile Leu Ser His Glu Glu Ile Tyr Ser
                165                 170                 175

His Leu Trp Pro Gly Glu Ser Pro Pro Ser Ser Asn Val Leu Ala Ala
            180                 185                 190

Leu Val Arg Leu Leu Arg Arg Lys Ile Glu Gln Pro Asn Ala Pro Arg
        195                 200                 205

Leu Ile Asn Ser Val Tyr Gly Lys Gly Tyr Cys Phe Glu Ala Asn
    210                 215                 220

<210> SEQ ID NO 21
<211> LENGTH: 228
```

```
<212> TYPE: PRT
<213> ORGANISM: Artificial Sequence
<220> FEATURE:
<223> OTHER INFORMATION: Synthetic: CcaR-BceR (137aa)

<400> SEQUENCE: 21

Met Arg Ile Leu Leu Val Glu Asp Asp Leu Pro Leu Ala Glu Thr Leu
1               5                   10                  15

Ala Glu Ala Leu Ser Asp Gln Leu Tyr Thr Val Asp Ile Ala Thr Asp
            20                  25                  30

Ala Ser Leu Ala Trp Asp Tyr Ala Ser Arg Leu Glu Tyr Asp Leu Val
        35                  40                  45

Ile Leu Asp Val Met Leu Pro Glu Leu Asp Gly Ile Thr Leu Cys Gln
    50                  55                  60

Lys Trp Arg Ser His Ser Tyr Leu Met Pro Ile Leu Met Met Thr Ala
65                  70                  75                  80

Arg Asp Thr Ile Asn Asp Lys Ile Thr Gly Leu Asp Ala Gly Ala Asp
                85                  90                  95

Asp Tyr Val Val Lys Pro Val Asp Leu Gly Glu Leu Phe Ala Arg Val
            100                 105                 110

Arg Ala Leu Leu Arg Arg Gly Cys Ala Thr Cys Gln Pro Val Lys Thr
        115                 120                 125

Trp Cys Gly Ala Ala Val Asp Ala Glu Gln Asn Leu Val Ser Asn Asp
    130                 135                 140

Lys Gly Ser Val Glu Leu Thr Lys Asn Glu Met Phe Ile Leu Lys Gln
145                 150                 155                 160

Leu Ile Glu Gln Lys Asn Lys Ile Val Ser Arg Glu Glu Leu Ile Arg
                165                 170                 175

Ser Leu Trp Asn Asp Glu Arg Phe Val Ser Asp Asn Thr Leu Thr Val
            180                 185                 190

Asn Val Asn Arg Leu Arg Lys Lys Leu Asp Ala Leu Gln Leu Gly Ala
        195                 200                 205

Tyr Ile Glu Thr Lys Val Gly Gln Gly Tyr Ile Ala Lys Glu Glu Asp
    210                 215                 220

Lys Phe Tyr Asp
225

<210> SEQ ID NO 22
<211> LENGTH: 230
<212> TYPE: PRT
<213> ORGANISM: Artificial Sequence
<220> FEATURE:
<223> OTHER INFORMATION: Synthetic: CcaR-PsdR (137aa)

<400> SEQUENCE: 22

Met Arg Ile Leu Leu Val Glu Asp Asp Leu Pro Leu Ala Glu Thr Leu
1               5                   10                  15

Ala Glu Ala Leu Ser Asp Gln Leu Tyr Thr Val Asp Ile Ala Thr Asp
            20                  25                  30

Ala Ser Leu Ala Trp Asp Tyr Ala Ser Arg Leu Glu Tyr Asp Leu Val
        35                  40                  45

Ile Leu Asp Val Met Leu Pro Glu Leu Asp Gly Ile Thr Leu Cys Gln
    50                  55                  60

Lys Trp Arg Ser His Ser Tyr Leu Met Pro Ile Leu Met Met Thr Ala
65                  70                  75                  80

Arg Asp Thr Ile Asn Asp Lys Ile Thr Gly Leu Asp Ala Gly Ala Asp
                85                  90                  95
```

Asp Tyr Val Val Lys Pro Val Asp Leu Gly Glu Leu Phe Ala Arg Val
            100                 105                 110

Arg Ala Leu Leu Arg Arg Gly Cys Ala Thr Cys Gln Pro Val Val Glu
        115                 120                 125

Leu Gly Gly Leu Thr Ile Tyr Pro Asp Gln Asn Glu Ala Glu Trp Asn
    130                 135                 140

Ser Val Arg Ile Leu Phe Ser Gln Lys Glu Phe Gln Leu Leu Ser Ile
145                 150                 155                 160

Phe Val Arg Glu His Lys Lys Ile Val Ser Arg Asp Glu Leu Leu Glu
                165                 170                 175

Ala Leu Trp Asp Asp Val Asp Phe Val Asp Asp Asn Thr Leu Thr Val
                180                 185                 190

Asn Val Asn Arg Leu Arg Arg Lys Leu Glu Asn Ala Gly Leu Thr Asp
            195                 200                 205

Cys Ile Ser Thr Ile Arg Gly Gln Gly Tyr Gln Phe Gln Val Asn Arg
210                 215                 220

Lys Asp Glu Ala Glu Cys
225                 230

<210> SEQ ID NO 23
<211> LENGTH: 224
<212> TYPE: PRT
<213> ORGANISM: Artificial Sequence
<220> FEATURE:
<223> OTHER INFORMATION: Synthetic: CcaR-YxdJ (137aa)

<400> SEQUENCE: 23

Met Arg Ile Leu Leu Val Glu Asp Asp Leu Pro Leu Ala Glu Thr Leu
1               5                   10                  15

Ala Glu Ala Leu Ser Asp Gln Leu Tyr Thr Val Asp Ile Ala Thr Asp
            20                  25                  30

Ala Ser Leu Ala Trp Asp Tyr Ala Ser Arg Leu Glu Tyr Asp Leu Val
        35                  40                  45

Ile Leu Asp Val Met Leu Pro Glu Leu Asp Gly Ile Thr Leu Cys Gln
    50                  55                  60

Lys Trp Arg Ser His Ser Tyr Leu Met Pro Ile Leu Met Met Thr Ala
65                  70                  75                  80

Arg Asp Thr Ile Asn Asp Lys Ile Thr Gly Leu Asp Ala Gly Ala Asp
                85                  90                  95

Asp Tyr Val Val Lys Pro Val Asp Leu Gly Glu Leu Phe Ala Arg Val
            100                 105                 110

Arg Ala Leu Leu Arg Arg Gly Cys Ala Thr Cys Gln Pro Val Val Glu
        115                 120                 125

Tyr Ala Gly Val Gln Leu Phe Val Glu Arg Phe Glu Leu Arg Phe Gln
    130                 135                 140

Asp Glu Lys Ser Glu Leu Ser Lys Lys Glu Ser Lys Leu Leu Glu Val
145                 150                 155                 160

Leu Leu Glu Arg Gly Glu Lys Val Thr Ser Arg Asp Arg Leu Met Glu
                165                 170                 175

Lys Thr Trp Asp Thr Asp Ile Phe Ile Asp Asp Asn Thr Leu Asn Val
                180                 185                 190

Tyr Ile Thr Arg Leu Arg Lys Lys Leu Arg Glu Leu Asn Ala Pro Val
            195                 200                 205

Ser Ile Glu Ala Val Arg Gly Glu Gly Tyr Gln Leu Arg Ala Gln Ser
210                 215                 220

<210> SEQ ID NO 24
<211> LENGTH: 242
<212> TYPE: PRT
<213> ORGANISM: Artificial Sequence
<220> FEATURE:
<223> OTHER INFORMATION: Synthetic: BAD_0569-CcaR (137aa)

<400> SEQUENCE: 24

Met Ser Lys Pro Ile Glu Ala Ser Ile Val Val Asp Asp Glu Pro
1               5                   10                  15

Ser Ile Arg Glu Leu Leu Val Ala Ser Leu His Phe Ala Gly Phe Glu
            20                  25                  30

Val Asn Thr Ala Ala Ser Gly Ser Glu Ala Ile Glu Val Ile Glu Arg
        35                  40                  45

Leu Gln Pro Asp Leu Ile Val Leu Asp Val Met Leu Pro Asp Ile Asp
    50                  55                  60

Gly Phe Thr Val Thr Arg Arg Ile Arg Gln Glu Gly Ile Thr Thr Pro
65                  70                  75                  80

Val Leu Tyr Leu Thr Ala Arg Asp Asp Thr Gln Asp Lys Val Met Gly
                85                  90                  95

Leu Thr Val Gly Gly Asp Asp Tyr Val Thr Lys Pro Phe Ser Leu Glu
            100                 105                 110

Glu Val Val Ala Arg Ile Arg Ala Ile Leu Arg Arg Thr Gln Gln Gln
        115                 120                 125

Val Glu Asp Asp Pro Val Leu Glu Trp Gly Pro Ile Arg Leu Asp Pro
    130                 135                 140

Ser Thr Tyr Glu Val Ser Tyr Asp Asn Glu Val Leu Ser Leu Thr Arg
145                 150                 155                 160

Lys Glu Tyr Ser Ile Leu Glu Leu Leu Leu Arg Asn Gly Arg Arg Val
                165                 170                 175

Leu Ser Arg Ser Met Ile Ile Asp Ser Ile Trp Lys Leu Glu Ser Pro
            180                 185                 190

Pro Glu Glu Asp Thr Val Lys Val His Val Arg Ser Leu Arg Gln Lys
        195                 200                 205

Leu Lys Ser Ala Gly Leu Ser Ala Asp Ala Ile Glu Thr Val His Gly
    210                 215                 220

Ile Gly Tyr Arg Leu Ala Asn Leu Thr Glu Lys Ser Leu Cys Gln Gly
225                 230                 235                 240

Lys Asn

<210> SEQ ID NO 25
<211> LENGTH: 216
<212> TYPE: PRT
<213> ORGANISM: E. coli
<220> FEATURE:
<221> NAME/KEY: misc_feature
<222> LOCATION: (1)..(216)
<223> OTHER INFORMATION: NarL (E. coli)

<400> SEQUENCE: 25

Met Ser Asn Gln Glu Pro Ala Thr Ile Leu Leu Ile Asp Asp His Pro
1               5                   10                  15

Met Leu Arg Thr Gly Val Lys Gln Leu Ile Ser Met Ala Pro Asp Ile
            20                  25                  30

Thr Val Val Gly Glu Ala Ser Asn Gly Glu Gln Gly Ile Glu Leu Ala
        35                  40                  45

```
Glu Ser Leu Asp Pro Asp Leu Ile Leu Leu Asp Leu Asn Met Pro Gly
 50                  55                  60

Met Asn Gly Leu Glu Thr Leu Asp Lys Leu Arg Glu Lys Ser Leu Ser
 65                  70                  75                  80

Gly Arg Ile Val Val Phe Ser Val Ser Asn His Glu Glu Asp Val Val
                 85                  90                  95

Thr Ala Leu Lys Arg Gly Ala Asp Gly Tyr Leu Leu Lys Asp Met Glu
            100                 105                 110

Pro Glu Asp Leu Leu Lys Ala Leu His Gln Ala Ala Gly Glu Met
        115                 120                 125

Val Leu Ser Glu Ala Leu Thr Pro Val Leu Ala Ser Leu Arg Ala
130                 135                 140

Asn Arg Ala Thr Thr Glu Arg Asp Val Asn Gln Leu Thr Pro Arg Glu
145                 150                 155                 160

Arg Asp Ile Leu Lys Leu Ile Ala Gln Gly Leu Pro Asn Lys Met Ile
                165                 170                 175

Ala Arg Arg Leu Asp Ile Thr Glu Ser Thr Val Lys Val His Val Lys
            180                 185                 190

His Met Leu Lys Lys Met Lys Leu Lys Ser Arg Val Glu Ala Ala Val
        195                 200                 205

Trp Val His Gln Glu Arg Ile Phe
210                 215

<210> SEQ ID NO 26
<211> LENGTH: 196
<212> TYPE: PRT
<213> ORGANISM: E. coli
<220> FEATURE:
<221> NAME/KEY: misc_feature
<222> LOCATION: (1)..(196)
<223> OTHER INFORMATION: UhpA (E. coli)

<400> SEQUENCE: 26

Met Ile Thr Val Ala Leu Ile Asp Asp His Leu Ile Val Arg Ser Gly
 1               5                  10                  15

Phe Ala Gln Leu Leu Gly Leu Glu Pro Asp Leu Gln Val Val Ala Glu
            20                  25                  30

Phe Gly Ser Gly Arg Glu Ala Leu Ala Gly Leu Pro Gly Arg Gly Val
        35                  40                  45

Gln Val Cys Ile Cys Asp Ile Ser Met Pro Asp Ile Ser Gly Leu Glu
 50                  55                  60

Leu Leu Ser Gln Leu Pro Lys Gly Met Ala Thr Ile Met Leu Ser Val
 65                  70                  75                  80

His Asp Ser Pro Ala Leu Val Glu Gln Ala Leu Asn Ala Gly Ala Arg
                 85                  90                  95

Gly Phe Leu Ser Lys Arg Cys Ser Pro Asp Glu Leu Ile Ala Ala Val
            100                 105                 110

His Thr Val Ala Thr Gly Gly Cys Tyr Leu Thr Pro Asp Ile Ala Ile
        115                 120                 125

Lys Leu Ala Ser Gly Arg Gln Asp Pro Leu Thr Lys Arg Glu Arg Gln
130                 135                 140

Val Ala Glu Lys Leu Ala Gln Gly Met Ala Val Lys Glu Ile Ala Ala
145                 150                 155                 160

Glu Leu Gly Leu Ser Pro Lys Thr Val His Val His Arg Ala Asn Leu
                165                 170                 175

Met Glu Lys Leu Gly Val Ser Asn Asp Val Glu Leu Ala Arg Arg Met
```

```
                     180                 185                 190

Phe Asp Gly Trp
        195

<210> SEQ ID NO 27
<211> LENGTH: 213
<212> TYPE: PRT
<213> ORGANISM: B. subtilis
<220> FEATURE:
<221> NAME/KEY: misc_feature
<222> LOCATION: (1)..(213)
<223> OTHER INFORMATION: YdfI (B. subtilis)

<400> SEQUENCE: 27

Met Asn Lys Val Leu Ile Val Asp Asp His Leu Val Val Arg Glu Gly
1               5                   10                  15

Leu Lys Leu Leu Ile Glu Thr Asn Asp Gln Tyr Thr Ile Ile Gly Glu
            20                  25                  30

Ala Glu Asn Gly Lys Val Ala Val Arg Leu Ala Asp Glu Leu Glu Pro
        35                  40                  45

Asp Ile Ile Leu Met Asp Leu Tyr Met Pro Glu Met Ser Gly Leu Glu
    50                  55                  60

Ala Ile Lys Gln Ile Lys Glu Lys His Asp Thr Pro Ile Ile Ile Leu
65                  70                  75                  80

Thr Thr Tyr Asn Glu Asp His Leu Met Ile Glu Gly Ile Glu Leu Gly
                85                  90                  95

Ala Lys Gly Tyr Leu Leu Lys Asp Thr Ser Ser Glu Thr Leu Phe His
            100                 105                 110

Thr Met Asp Ala Ala Ile Arg Gly Asn Val Leu Leu Gln Pro Asp Ile
        115                 120                 125

Leu Lys Arg Leu Gln Glu Ile Gln Phe Glu Arg Met Lys Lys Gln Arg
    130                 135                 140

Asn Glu Thr Gln Leu Thr Glu Lys Glu Val Ile Val Leu Lys Ala Ile
145                 150                 155                 160

Ala Lys Gly Leu Lys Ser Lys Ala Ile Ala Phe Asp Leu Gly Val Ser
                165                 170                 175

Glu Arg Thr Val Lys Ser Arg Leu Thr Ser Ile Tyr Asn Lys Leu Gly
            180                 185                 190

Ala Asn Ser Arg Thr Glu Ala Val Thr Ile Ala Met Gln Lys Gly Ile
        195                 200                 205

Leu Thr Ile Asp Asn
    210

<210> SEQ ID NO 28
<211> LENGTH: 211
<212> TYPE: PRT
<213> ORGANISM: B. subtilis
<220> FEATURE:
<221> NAME/KEY: misc_feature
<222> LOCATION: (1)..(211)
<223> OTHER INFORMATION: LiaR (B. subtilis)

<400> SEQUENCE: 28

Met Ile Arg Val Leu Leu Ile Asp Asp His Glu Met Val Arg Met Gly
1               5                   10                  15

Leu Ala Ala Phe Leu Glu Ala Gln Pro Asp Ile Glu Val Ile Gly Glu
            20                  25                  30

Ala Ser Asp Gly Ser Glu Gly Val Arg Leu Ala Val Glu Leu Ser Pro
        35                  40                  45
```

Asp Val Ile Leu Met Asp Leu Val Met Glu Gly Met Asp Gly Ile Glu
            50                  55                  60

Ala Thr Lys Gln Ile Cys Arg Glu Leu Ser Asp Pro Lys Ile Ile Val
65                  70                  75                  80

Leu Thr Ser Phe Ile Asp Asp Lys Val Tyr Pro Val Ile Glu Ala
                85                  90                  95

Gly Ala Leu Ser Tyr Leu Leu Lys Thr Ser Lys Ala Ala Glu Ile Ala
                100                 105                 110

Asp Ala Ile Arg Ala Ala Ser Lys Gly Glu Pro Lys Leu Glu Ser Lys
            115                 120                 125

Val Ala Gly Lys Val Leu Ser Arg Leu Arg His Ser Gly Glu Asn Ala
            130                 135                 140

Leu Pro His Glu Ser Leu Thr Lys Arg Glu Leu Glu Ile Leu Cys Leu
145                 150                 155                 160

Ile Ala Glu Gly Lys Thr Asn Lys Glu Ile Gly Glu Glu Leu Phe Ile
                165                 170                 175

Thr Ile Lys Thr Val Lys Thr His Ile Thr Asn Ile Leu Ser Lys Leu
                180                 185                 190

Asp Val Ser Asp Arg Thr Gln Ala Ala Val Tyr Ala His Arg Asn His
            195                 200                 205

Leu Val Asn
    210

<210> SEQ ID NO 29
<211> LENGTH: 209
<212> TYPE: PRT
<213> ORGANISM: E. coli
<220> FEATURE:
<221> NAME/KEY: misc_feature
<222> LOCATION: (1)..(209)
<223> OTHER INFORMATION: FusR (E. coli)

<400> SEQUENCE: 29

Met Ile Arg Val Val Leu Val Asp Asp His Val Val Arg Ser Gly
1               5                   10                  15

Phe Ala Gln Leu Leu Ser Leu Glu Asp Asp Leu Glu Val Ile Gly Gln
                20                  25                  30

Tyr Ser Ser Ala Ala Gln Ala Trp Ser Ala Leu Ile Arg Asp Asp Val
            35                  40                  45

Asn Val Ala Val Ile Asp Ile Ala Met Pro Asp Glu Asn Gly Leu Ser
50                  55                  60

Leu Leu Lys Arg Leu Arg Ala Gln Lys Pro Gln Phe Arg Ala Ile Ile
65                  70                  75                  80

Leu Ser Ile Tyr Asp Ala Pro Thr Phe Val Gln Ser Ala Leu Asp Ala
                85                  90                  95

Gly Ala Ser Gly Tyr Leu Thr Lys Arg Cys Gly Pro Glu Glu Leu Val
                100                 105                 110

Gln Ala Val Arg Ser Val Gly Leu Gly Gly His Tyr Leu Cys Ala Asp
            115                 120                 125

Ala Ile Arg Ala Leu Arg Gly Gly Gly Gln Pro Ala Gln Ala Leu Glu
            130                 135                 140

Ile Leu Thr Pro Arg Glu Arg Glu Val Phe Glu Leu Leu Val Lys Gly
145                 150                 155                 160

Asp Ser Val Lys Glu Ile Ala Phe Lys Leu Glu Leu Ser His Lys Thr
                165                 170                 175

Val His Val His Arg Ala Asn Val Leu Gly Lys Leu Asn Cys His Ser
            180                 185                 190

Thr Ile Glu Leu Val His Phe Ala Leu Asp His His Leu Leu Ala Gly
        195                 200                 205

His

<210> SEQ ID NO 30
<211> LENGTH: 219
<212> TYPE: PRT
<213> ORGANISM: Artificial Sequence
<220> FEATURE:
<223> OTHER INFORMATION: Synthetic: NarL-YdfI (131aa)

<400> SEQUENCE: 30

Met Ser Asn Gln Glu Pro Ala Thr Ile Leu Leu Ile Asp Asp His Pro
1               5                   10                  15

Met Leu Arg Thr Gly Val Lys Gln Leu Ile Ser Met Ala Pro Asp Ile
            20                  25                  30

Thr Val Val Gly Glu Ala Ser Asn Gly Glu Gln Gly Ile Glu Leu Ala
        35                  40                  45

Glu Ser Leu Asp Pro Asp Leu Ile Leu Leu Asp Leu Asn Met Pro Gly
    50                  55                  60

Met Asn Gly Leu Glu Thr Leu Asp Lys Leu Arg Glu Lys Ser Leu Ser
65                  70                  75                  80

Gly Arg Ile Val Val Phe Ser Val Ser Asn His Glu Glu Asp Val Val
                85                  90                  95

Thr Ala Leu Lys Arg Gly Ala Asp Gly Tyr Leu Leu Lys Asp Met Glu
            100                 105                 110

Pro Glu Asp Leu Leu Lys Ala Leu His Gln Ala Ala Gly Glu Met
        115                 120                 125

Val Leu Ser Pro Asp Ile Leu Lys Arg Leu Gln Glu Ile Gln Phe Glu
130                 135                 140

Arg Met Lys Lys Gln Arg Asn Glu Thr Gln Leu Thr Glu Lys Glu Val
145                 150                 155                 160

Ile Val Leu Lys Ala Ile Ala Lys Gly Leu Lys Ser Lys Ala Ile Ala
                165                 170                 175

Phe Asp Leu Gly Val Ser Glu Arg Thr Val Lys Ser Arg Leu Thr Ser
            180                 185                 190

Ile Tyr Asn Lys Leu Gly Ala Asn Ser Arg Thr Glu Ala Val Thr Ile
        195                 200                 205

Ala Met Gln Lys Gly Ile Leu Thr Ile Asp Asn
    210                 215

<210> SEQ ID NO 31
<211> LENGTH: 211
<212> TYPE: PRT
<213> ORGANISM: Artificial Sequence
<220> FEATURE:
<223> OTHER INFORMATION: Synthetic: UhpA-YdfI (131aa)

<400> SEQUENCE: 31

Met Ile Thr Val Ala Leu Ile Asp Asp His Leu Ile Val Arg Ser Gly
1               5                   10                  15

Phe Ala Gln Leu Leu Gly Leu Glu Pro Asp Leu Gln Val Val Ala Glu
            20                  25                  30

Phe Gly Ser Gly Arg Glu Ala Leu Ala Gly Leu Pro Gly Arg Gly Val
        35                  40                  45

```
Gln Val Cys Ile Cys Asp Ile Ser Met Pro Asp Ile Ser Gly Leu Glu
 50                  55                  60

Leu Leu Ser Gln Leu Pro Lys Gly Met Ala Thr Ile Met Leu Ser Val
 65                  70                  75                  80

His Asp Ser Pro Ala Leu Val Glu Gln Ala Leu Asn Ala Gly Ala Arg
                 85                  90                  95

Gly Phe Leu Ser Lys Arg Cys Ser Pro Asp Glu Leu Ile Ala Ala Val
                100                 105                 110

His Thr Val Ala Thr Gly Gly Cys Tyr Leu Thr Pro Asp Ile Leu Lys
                115                 120                 125

Arg Leu Gln Glu Ile Gln Phe Glu Arg Met Lys Lys Gln Arg Asn Glu
130                 135                 140

Thr Gln Leu Thr Glu Lys Glu Val Ile Val Leu Lys Ala Ile Ala Lys
145                 150                 155                 160

Gly Leu Lys Ser Lys Ala Ile Ala Phe Asp Leu Gly Val Ser Glu Arg
                165                 170                 175

Thr Val Lys Ser Arg Leu Thr Ser Ile Tyr Asn Lys Leu Gly Ala Asn
                180                 185                 190

Ser Arg Thr Glu Ala Val Thr Ile Ala Met Gln Lys Gly Ile Leu Thr
                195                 200                 205

Ile Asp Asn
210

<210> SEQ ID NO 32
<211> LENGTH: 208
<212> TYPE: PRT
<213> ORGANISM: Artificial Sequence
<220> FEATURE:
<223> OTHER INFORMATION: Synthetic: UhpA-LiaR (131aa)

<400> SEQUENCE: 32

Met Ile Thr Val Ala Leu Ile Asp Asp His Leu Ile Val Arg Ser Gly
  1               5                  10                  15

Phe Ala Gln Leu Leu Gly Leu Glu Pro Asp Leu Gln Val Val Ala Glu
                 20                  25                  30

Phe Gly Ser Gly Arg Glu Ala Leu Ala Gly Leu Pro Gly Arg Gly Val
                 35                  40                  45

Gln Val Cys Ile Cys Asp Ile Ser Met Pro Asp Ile Ser Gly Leu Glu
 50                  55                  60

Leu Leu Ser Gln Leu Pro Lys Gly Met Ala Thr Ile Met Leu Ser Val
 65                  70                  75                  80

His Asp Ser Pro Ala Leu Val Glu Gln Ala Leu Asn Ala Gly Ala Arg
                 85                  90                  95

Gly Phe Leu Ser Lys Arg Cys Ser Pro Asp Glu Leu Ile Ala Ala Val
                100                 105                 110

His Thr Val Ala Thr Gly Gly Cys Tyr Leu Thr Ser Lys Val Ala Gly
                115                 120                 125

Lys Val Leu Ser Arg Leu Arg His Ser Gly Glu Asn Ala Leu Pro His
130                 135                 140

Glu Ser Leu Thr Lys Arg Glu Leu Glu Ile Leu Cys Leu Ile Ala Glu
145                 150                 155                 160

Gly Lys Thr Asn Lys Glu Ile Gly Glu Glu Leu Phe Ile Thr Ile Lys
                165                 170                 175

Thr Val Lys Thr His Ile Thr Asn Ile Leu Ser Lys Leu Asp Val Ser
                180                 185                 190
```

-continued

Asp Arg Thr Gln Ala Ala Val Tyr Ala His Arg Asn His Leu Val Asn
         195                 200                 205

<210> SEQ ID NO 33
<211> LENGTH: 214
<212> TYPE: PRT
<213> ORGANISM: Artificial Sequence
<220> FEATURE:
<223> OTHER INFORMATION: Synthetic: FusR-YdfI (129aa)

<400> SEQUENCE: 33

Met Ile Arg Val Val Leu Val Asp Asp His Val Val Arg Ser Gly
1               5                   10                  15

Phe Ala Gln Leu Leu Ser Leu Glu Asp Asp Leu Glu Val Ile Gly Gln
            20                  25                  30

Tyr Ser Ser Ala Ala Gln Ala Trp Ser Ala Leu Ile Arg Asp Asp Val
        35                  40                  45

Asn Val Ala Val Ile Asp Ile Ala Met Pro Asp Glu Asn Gly Leu Ser
    50                  55                  60

Leu Leu Lys Arg Leu Arg Ala Gln Lys Pro Gln Phe Arg Ala Ile Ile
65                  70                  75                  80

Leu Ser Ile Tyr Asp Ala Pro Thr Phe Val Gln Ser Ala Leu Asp Ala
                85                  90                  95

Gly Ala Ser Gly Tyr Leu Thr Lys Arg Cys Gly Pro Glu Glu Leu Val
            100                 105                 110

Gln Ala Val Arg Ser Val Gly Leu Gly Gly His Tyr Leu Gln Pro Asp
        115                 120                 125

Ile Leu Lys Arg Leu Gln Glu Ile Gln Phe Glu Arg Met Lys Lys Gln
    130                 135                 140

Arg Asn Glu Thr Gln Leu Thr Glu Lys Glu Val Ile Val Leu Lys Ala
145                 150                 155                 160

Ile Ala Lys Gly Leu Lys Ser Lys Ala Ile Ala Phe Asp Leu Gly Val
                165                 170                 175

Ser Glu Arg Thr Val Lys Ser Arg Leu Thr Ser Ile Tyr Asn Lys Leu
            180                 185                 190

Gly Ala Asn Ser Arg Thr Glu Ala Val Thr Ile Ala Met Gln Lys Gly
        195                 200                 205

Ile Leu Thr Ile Asp Asn
    210

<210> SEQ ID NO 34
<211> LENGTH: 29
<212> TYPE: PRT
<213> ORGANISM: Artificial Sequence
<220> FEATURE:
<223> OTHER INFORMATION: Synthetic: Figure 2 - CcaR

<400> SEQUENCE: 34

Glu Leu Phe Ala Arg Val Arg Ala Leu Leu Arg Arg Gly Cys Ala Thr
1               5                   10                  15

Cys Gln Pro Val Leu Glu Trp Gly Pro Ile Arg Leu Asp
            20                  25

<210> SEQ ID NO 35
<211> LENGTH: 31
<212> TYPE: PRT
<213> ORGANISM: Artificial Sequence
<220> FEATURE:
<223> OTHER INFORMATION: Synthetic: Figure 2 - BAD_0568

<400> SEQUENCE: 35

Glu Val Val Ala Arg Ile Arg Ala Ile Leu Arg Arg Thr Gln Gln Gln
1               5                   10                  15

Val Glu Asp Asp Pro Ile Ile Arg Val Gly Asp Leu Glu Ile Asn
            20                  25                  30

<210> SEQ ID NO 36
<211> LENGTH: 450
<212> TYPE: PRT
<213> ORGANISM: Artificial Sequence
<220> FEATURE:
<223> OTHER INFORMATION: Synthetic: Figure 6 sequence

<400> SEQUENCE: 36

Met Arg Arg Leu Arg Phe Ser Pro Arg Ser Ser Phe Ala Arg Thr Leu
1               5                   10                  15

Leu Leu Ile Val Thr Leu Leu Phe Ala Ser Leu Val Thr Thr Tyr Leu
            20                  25                  30

Val Val Leu Asn Phe Ala Ile Leu Pro Ser Leu Gln Gln Phe Asn Lys
        35                  40                  45

Val Leu Ala Tyr Glu Val Arg Met Leu Met Thr Asp Lys Leu Gln Leu
    50                  55                  60

Glu Asp Gly Thr Gln Leu Val Val Pro Pro Ala Phe Arg Arg Glu Ile
65                  70                  75                  80

Tyr Arg Glu Leu Gly Ile Ser Leu Tyr Ser Asn Glu Ala Ala Glu Glu
                85                  90                  95

Ala Gly Leu Arg Trp Ala Gln His Tyr Glu Phe Leu Ser His Gln Met
            100                 105                 110

Ala Gln Gln Leu Gly Gly Pro Thr Glu Val Arg Val Glu Val Asn Lys
        115                 120                 125

Ser Ser Pro Val Val Trp Leu Lys Thr Trp Leu Ser Pro Asn Ile Trp
    130                 135                 140

Val Arg Val Pro Leu Thr Glu Ile His Gln Gly Asp Phe Ser Pro Leu
145                 150                 155                 160

Phe Arg Tyr Thr Leu Ala Ile Met Leu Leu Ala Ile Gly Gly Ala Trp
                165                 170                 175

Leu Phe Ile Arg Ile Gln Asn Arg Pro Leu Val Asp Leu Glu His Ala
            180                 185                 190

Ala Leu Gln Val Gly Lys Gly Ile Ile Pro Pro Leu Arg Glu Tyr
        195                 200                 205

Gly Ala Ser Glu Val Arg Ser Val Thr Arg Ala Phe Asn His Met Ala
    210                 215                 220

Ala Gly Val Lys Gln Leu Ala Asp Asp Arg Thr Leu Leu Met Ala Gly
225                 230                 235                 240

Val Ser His Asp Leu Arg Thr Pro Leu Thr Arg Ile Arg Leu Ala Thr
                245                 250                 255

Glu Met Met Ser Glu Gln Asp Gly Tyr Leu Ala Glu Ser Ile Asn Lys
            260                 265                 270

Asp Ile Glu Glu Cys Asn Ala Ile Ile Glu Gln Phe Ile Asp Tyr Leu
        275                 280                 285

Arg Thr Gly Gln Glu Met Pro Met Glu Met Ala Asp Leu Asn Ala Val
    290                 295                 300

Leu Gly Glu Val Ile Ala Ala Glu Ser Gly Tyr Glu Arg Glu Ile Glu
305                 310                 315                 320

Thr Ala Leu Tyr Pro Gly Ser Ile Glu Val Lys Met His Pro Leu Ser

```
                          325                 330                 335
            Ile Lys Arg Ala Val Ala Asn Met Val Val Asn Ala Ala Arg Tyr Gly
                    340                 345                 350

Asn Gly Trp Ile Lys Val Ser Ser Gly Thr Glu Pro Asn Arg Ala Trp
                355                 360                 365

Phe Gln Val Glu Asp Asp Gly Pro Gly Ile Ala Pro Glu Gln Arg Lys
                370                 375                 380

His Leu Phe Gln Pro Phe Val Arg Gly Asp Ser Ala Arg Thr Ile Ser
            385                 390                 395                 400

Gly Thr Gly Leu Gly Leu Ala Ile Val Gln Arg Ile Val Asp Asn His
                            405                 410                 415

Asn Gly Met Leu Glu Leu Gly Thr Ser Glu Arg Gly Gly Leu Ser Ile
                        420                 425                 430

Arg Ala Trp Leu Pro Val Pro Val Thr Arg Ala Gln Gly Thr Thr Lys
                        435                 440                 445

Glu Gly
                450

<210> SEQ ID NO 37
<211> LENGTH: 593
<212> TYPE: PRT
<213> ORGANISM: Artificial Sequence
<220> FEATURE:
<223> OTHER INFORMATION: Synthetic: Figure 6 BAD_0569

<400> SEQUENCE: 37

Met Gln Pro Pro Arg Ser Leu Pro Lys Gln Asn Lys Val Trp Ser Arg
1               5                   10                  15

Phe Thr Arg Arg Ile Gln Ala Ile Pro Leu Ser Thr Lys Leu Val Thr
                20                  25                  30

Cys Ile Ile Val Leu Leu Thr Ile Gly Thr Ile Gly Ile Ser Phe Ser
            35                  40                  45

Ile Arg Thr Leu Val Gly Asn Tyr Leu Leu Gln Lys Thr Asp Thr Gln
        50                  55                  60

Leu Ile Asn Gln Ala Gln Leu Ile Phe Asn Ser Met Asp Ser Leu Ser
65              70                  75                  80

Ser Asp Thr Gly Asp Asp Gly Arg Ser Leu Met Asn Thr Tyr Tyr Val
                85                  90                  95

Glu Val Arg Asp Ser Glu Tyr Lys Ser Thr Gly Ala Gly Ser Val Pro
            100                 105                 110

Met Leu Arg Asp Gly Val Val Ser Glu Pro Ser Leu Pro Ala Asp Gly
        115                 120                 125

Ser Ile Asp Gly Val Thr Leu Gly Gln Pro Phe Thr Thr Arg Ala Val
    130                 135                 140

Val His Ile Thr Thr Ser Arg Thr Pro Asp His Ser Ile Met Gln Ala
145                 150                 155                 160

Ala Gln Ser Pro Trp Arg Val Val Ala Leu Pro Trp Asn Glu Lys Thr
                165                 170                 175

Arg Thr Gly Gln Val Lys Asp Ser Gly Val Val Phe Ile Gly Leu Ser
            180                 185                 190

Leu Ser Asp Gln Ile Asp Thr Ala Asn Thr Leu Thr Arg Phe Cys Ala
        195                 200                 205

Met Val Gly Ile Ala Val Leu Ile Gly Ala Ile Leu Gly Thr Ile
    210                 215                 220

Leu Val Gln Ser Thr Leu Ala Pro Leu Lys Arg Ile Glu Lys Thr Ala
```

```
                    225                 230                 235                 240
              Ala Lys Ile Ala Ala Gly Asp Leu Ser Gln Arg Val Pro Asp Leu Pro
                              245                 250                 255

Glu Ser Thr Glu Val Gly Ser Leu Ser Met Ser Leu Asn Thr Met Leu
                              260                 265                 270

Thr Arg Ile Glu Glu Ser Phe His Ala Gln Glu Thr Thr Glu Lys
                          275                 280                 285

Met Lys Arg Phe Val Ser Asp Ala Ser His Glu Leu Arg Thr Pro Leu
                          290                 295                 300

Ala Ala Ile His Gly Tyr Ala Glu Leu Tyr Lys Met Gln Arg Asp Met
              305                 310                 315                 320

Pro Gly Ala Leu Glu Arg Ala Asp Glu Ser Ile Glu His Ile Glu Ala
                              325                 330                 335

Ser Ser Ala Arg Met Thr Val Leu Val Glu Asp Leu Leu Ser Leu Ala
                              340                 345                 350

Arg Leu Asp Glu Gly Arg Gly Ile Asp Ile Thr Gln Gln Val Lys Leu
                              355                 360                 365

Thr Ser Val Val Arg Asp Ala Ala Asp Leu His Ala Leu Asp Pro
                          370                 375                 380

Asp Arg Gly Ile Ser Cys Gly Gln Val Val Leu Gln Pro Gly Thr Asp
              385                 390                 395                 400

Met Asp His Pro Ala Gln Phe Ala Phe Gln Asn Gly Gln Met Pro Gln
                              405                 410                 415

Ile Glu Leu Lys Gly Asp Ala Ser Arg Leu Arg Gln Val Val Thr Asn
                              420                 425                 430

Ile Val Gly Asn Ile His Arg Tyr Thr Pro Ala Asp Ser Pro Val Glu
                          435                 440                 445

Ile Ser Met Gly Val Leu Pro Ala Ser Ile Ser Pro Glu Ser Leu Ser
                          450                 455                 460

Arg Met Pro Ser Asn Glu Gln Ser Leu Arg His Leu Val Glu Ala Ile
              465                 470                 475                 480

Glu Val Gly Gln Ser Met Gln Val Gly Met Asn Tyr Ala Ile Val Arg
                              485                 490                 495

Phe Ser Asp His Gly Pro Gly Val Pro Pro Glu Ala Arg Ser Lys Ile
                          500                 505                 510

Phe Glu Arg Phe Tyr Thr Ala Asp Pro Ser Arg Ala Arg Gln Lys Gly
                          515                 520                 525

Gly Thr Gly Leu Gly Met Ala Ile Ala Gln Ser Val Val Lys Ala His
                      530                 535                 540

His Gly Phe Ile Cys Ala Ser Gly Ser Glu Gly Thr Gly Leu Ile Leu
              545                 550                 555                 560

Thr Val Val Leu Pro Ile Ala Pro Val Glu Pro Lys Pro Gln Pro Ile
                              565                 570                 575

Thr Ala Ser Glu Asn Arg Lys Asn Glu Lys Lys Asn Arg Lys Ser Lys
                          580                 585                 590

Lys
```